$\qquad$

US011497796B2

(12) United States Patent
Monnier et al.

(10) Patent No.: US 11,497,796 B2
(45) Date of Patent: Nov. 15, 2022

(54) AGENTS DIRECTED AGAINST A CIS RGMA/NEOGENIN INTERACTION OR LIPID RAFTS AND USE OF THE SAME IN METHODS OF TREATMENT

(71) Applicant: UNIVERSITY HEALTH NETWORK, Toronto (CA)

(72) Inventors: Philippe P. Monnier, Toronto (CA); Nardos G. Tassew, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 0 days.

(21) Appl. No.: 16/277,529

(22) Filed: Feb. 15, 2019

(65) Prior Publication Data

US 2019/0275118 A1    Sep. 12, 2019

Related U.S. Application Data

(62) Division of application No. 14/915,492, filed as application No. PCT/CA2014/000614 on Aug. 6, 2014, now abandoned.

(Continued)

(51) Int. Cl.
*A61K 38/17* (2006.01)
*A61K 49/00* (2006.01)
(Continued)

(52) U.S. Cl.
CPC .......... *A61K 38/443* (2013.01); *A61K 31/137* (2013.01); *A61K 31/365* (2013.01); *A61K 31/495* (2013.01); *A61K 31/7048* (2013.01); *A61K 31/724* (2013.01); *A61K 38/177* (2013.01); *A61K 38/482* (2013.01);
(Continued)

(58) Field of Classification Search
None
See application file for complete search history.

(56) References Cited

U.S. PATENT DOCUMENTS

2011/0112280 A1* 5/2011 Mueller ............... A61P 25/02
530/387.9
2011/0135664 A1   6/2011 Mueller

FOREIGN PATENT DOCUMENTS

WO      02072794       9/2002
WO    2004003150       1/2004
(Continued)

OTHER PUBLICATIONS

Dobson et al., Multiple Sclerosis—a review. European Journal of Neurology 2019, 26: 27-40 (Year: 2019).*
(Continued)

*Primary Examiner* — Aurora M Fontainhas
(74) *Attorney, Agent, or Firm* — Casimir Jones SC; Lisa Mueller

(57) ABSTRACT

Disclosed herein is an agent that modulates a cis interaction between Repulsive Guidance Molecule A (RGMa) and Neogenin or lipid rafts. Modulation by the agent may include blocking the cis interaction between RGMa and Neogenin and/or disrupting lipid rafts. In turn, this promotes neuronal cell survival and axon growth and/or regeneration. Also disclosed herein is a method of treating a disease in a subject in need thereof. The method may include administering the agent to the subject. Further disclosed herein is a method of identifying an agent that modulates the cis interaction between RGMa and Neogenin.

6 Claims, 29 Drawing Sheets

Specification includes a Sequence Listing.

Related U.S. Application Data

(60) Provisional application No. 61/878,827, filed on Sep. 17, 2013.

(51) Int. Cl.
| | | |
|---|---|---|
| *C07K 14/47* | (2006.01) | |
| *A61K 39/395* | (2006.01) | |
| *A61P 25/14* | (2006.01) | |
| *A61P 21/00* | (2006.01) | |
| *A61P 25/28* | (2006.01) | |
| *A61K 38/44* | (2006.01) | |
| *A61K 31/137* | (2006.01) | |
| *C07K 16/28* | (2006.01) | |
| *A61K 31/724* | (2006.01) | |
| *A61K 31/365* | (2006.01) | |
| *A61K 31/7048* | (2006.01) | |
| *A61K 38/48* | (2006.01) | |
| *C07K 14/435* | (2006.01) | |
| *C07K 14/705* | (2006.01) | |
| *G01N 33/53* | (2006.01) | |
| *A61K 31/495* | (2006.01) | |
| *G01N 33/50* | (2006.01) | |
| *A61K 39/00* | (2006.01) | |

(52) U.S. Cl.
CPC .......... *C07K 14/435* (2013.01); *C07K 14/705* (2013.01); *C07K 16/28* (2013.01); *C12Y 101/03006* (2013.01); *G01N 33/5058* (2013.01); *G01N 33/53* (2013.01); *A61K 2039/505* (2013.01); *C07K 2317/30* (2013.01); *C07K 2317/76* (2013.01); *G01N 2333/4703* (2013.01)

(56) References Cited

FOREIGN PATENT DOCUMENTS

| WO | 2007039256 | 4/2007 |
|---|---|---|
| WO | 2009106356 | 9/2009 |
| WO | 2011070045 | 6/2011 |

OTHER PUBLICATIONS

Tassew et al., SKI-1 and Furin Generate Multiple RGMa Fragments that Regulate Axonal Growth, Developmental Cell, vol. 22, Issue 2, 2012 (Year: 2012).*
Rajagopalan, S., Deitinghoff, L., Davis, D. et al. Neogenin mediates the action of repulsive guidance molecule. Nat Cell Biol 6, 756-762 (2004). https://doi.org/10.1038/ncb1156 (Year: 2004).*
International Preliminary Report on Patentability for Application No. PCT/CA2014/000614 dated Mar. 22, 2016 (10 pages).
Itokazu et al., "Identification of the Neogenin-Binding Site on the Repulsive Guidance Molecule A." PLoS ONE, Mar. 2012, vol. 7(3) p. e3279.
European Search Report for Application No. 14846230.2 dated Jul. 3, 2017 (13 pages).
Hata et al., "RGMa inhibition promotes axonal growth and recovery after spinal cord injury." J Cell Biol. Apr. 10, 2006;173(1):47-58.
Ponce et al., "Simvastatin reduces the association of NMDA receptors to lipid rafts: a cholesterol-mediated effect in neuroprotection." Stroke. Apr. 2008;39(4):1269-75.
Anonymous: "UPI000012FF2F", Jan. 1, 2003, XP055347427, Retrieved from the Internet <URL:http://www.uniprot.org/uniparc/UPI000012FF2F> retrieved on Feb. 17, 2017.
GenBank Accession No. AAA83259.1, 1995.
GenBank Accession No. AAC59662.1, 1995.
GenBank Accession No. AAI43272.1, 2009.
GenBank Accession No. NP_989868.1, 2014.

* cited by examiner

Figure 3
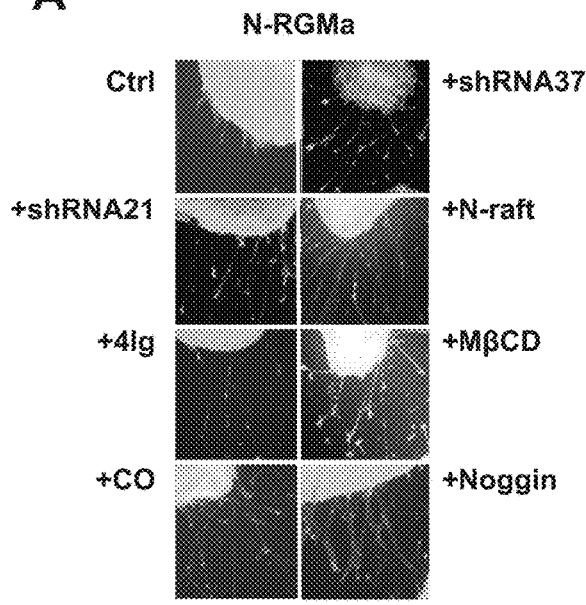
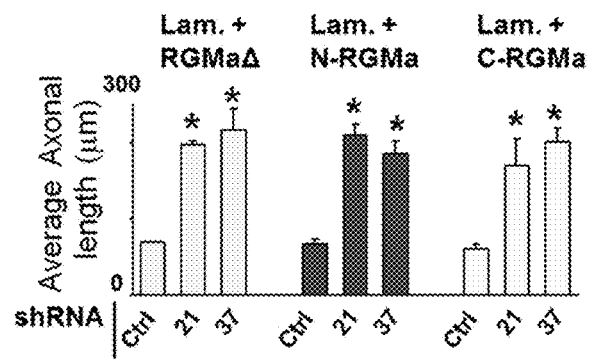
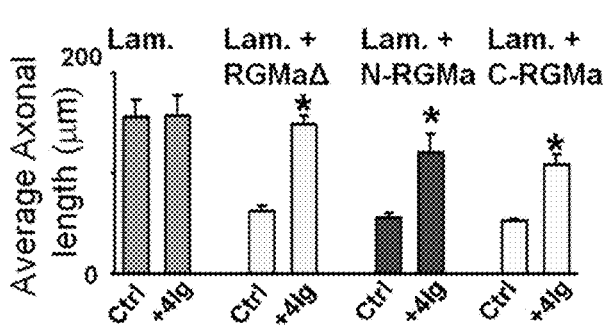
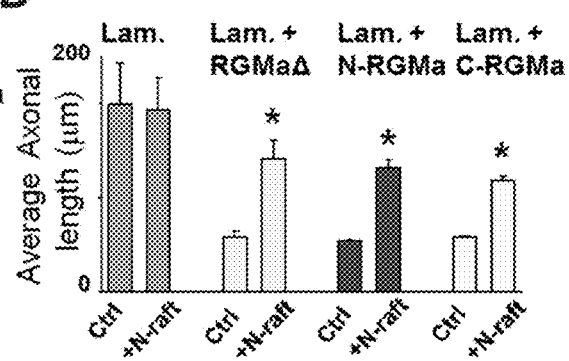
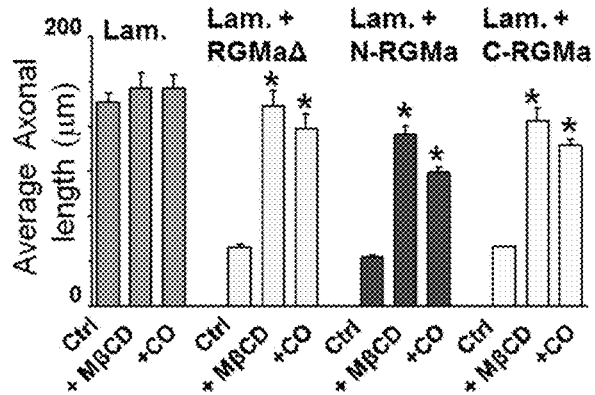
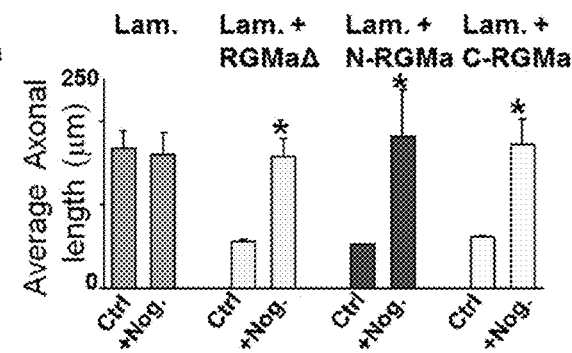

Figure 5 (CONTINUED)
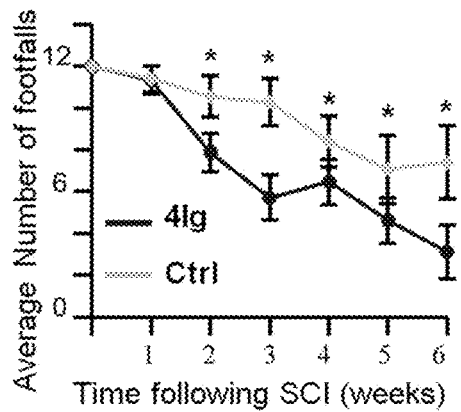
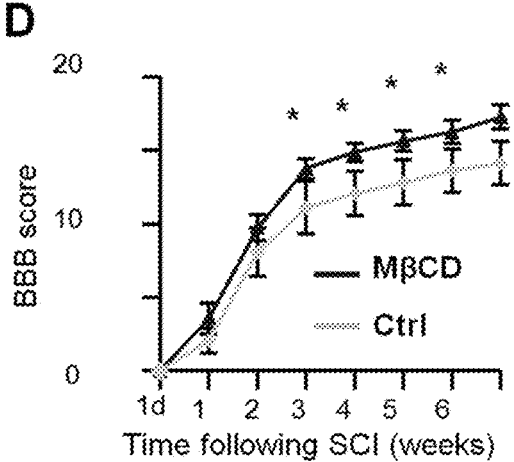
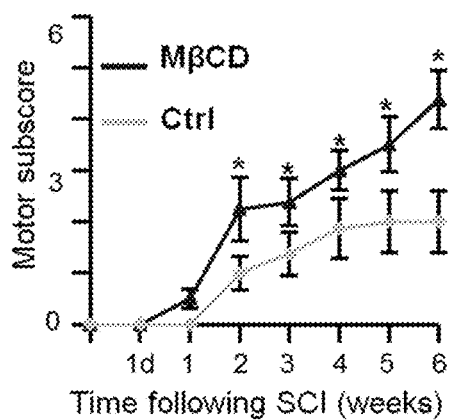
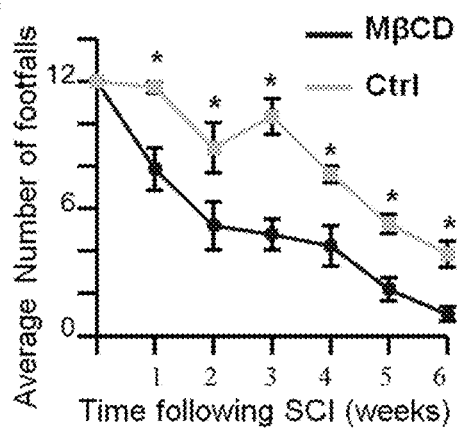
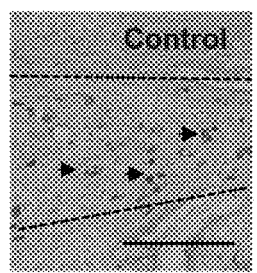
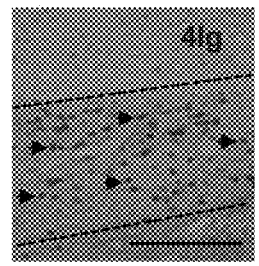
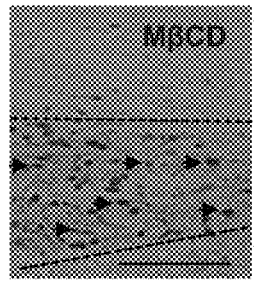
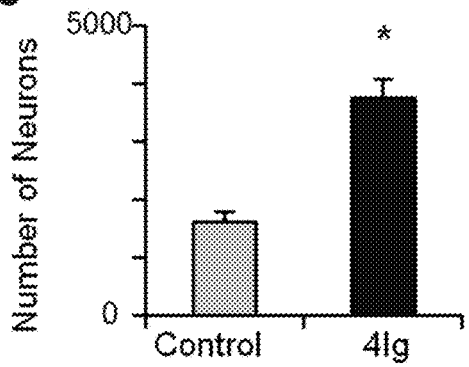

Figure 5 (CONTINUED)
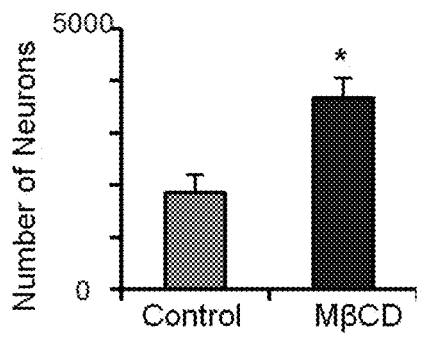
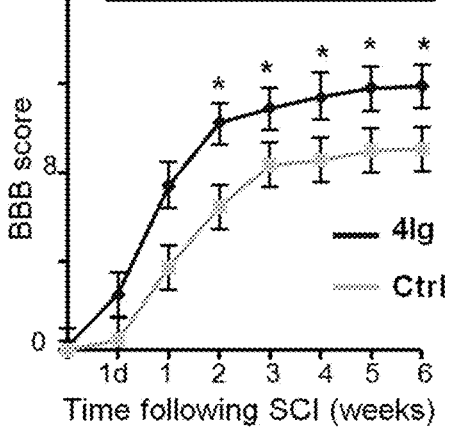
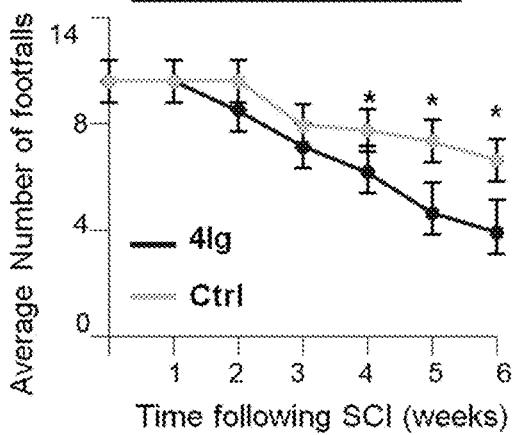
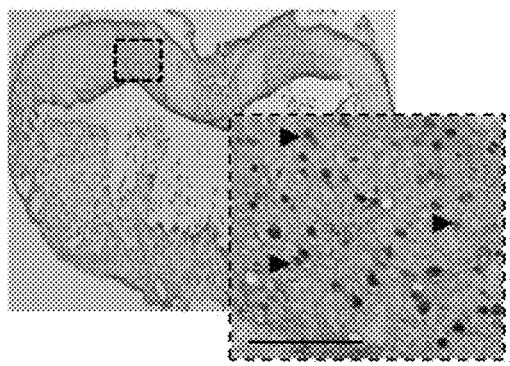
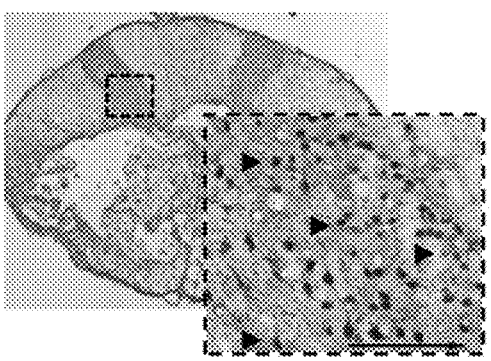
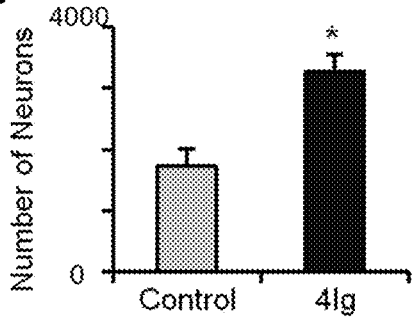

Figure 6
A Control
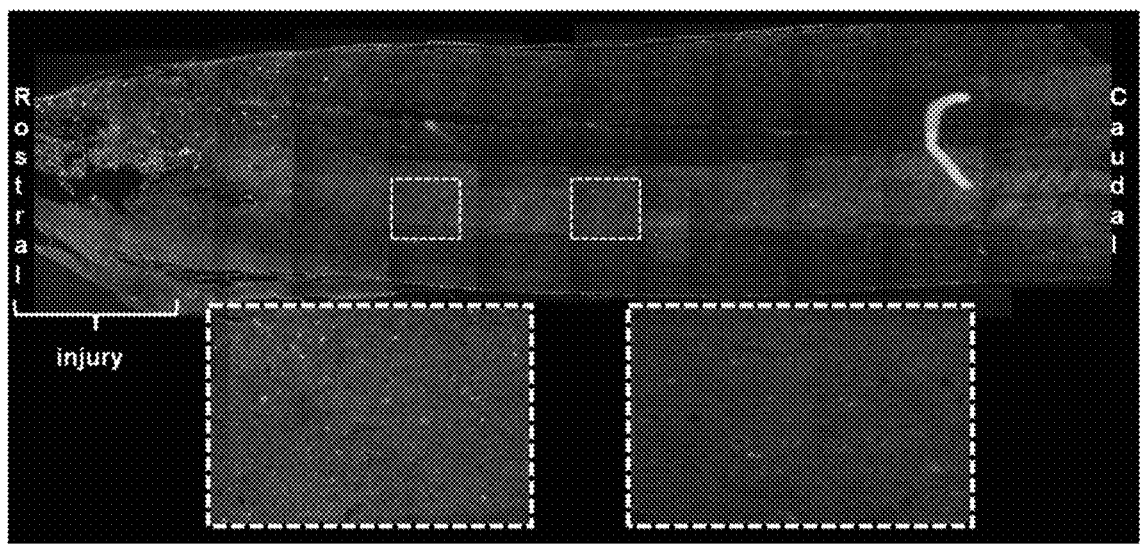
B 4Ig
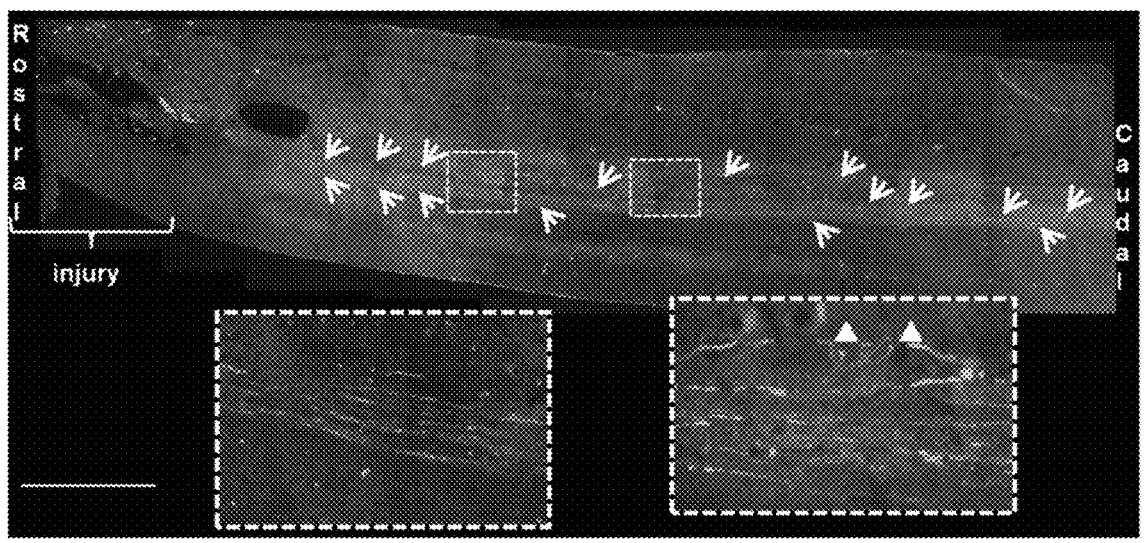
C
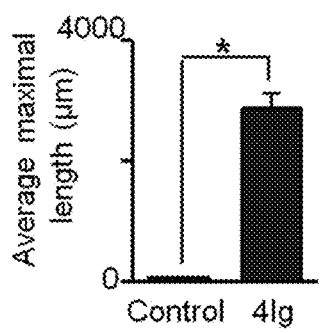
D
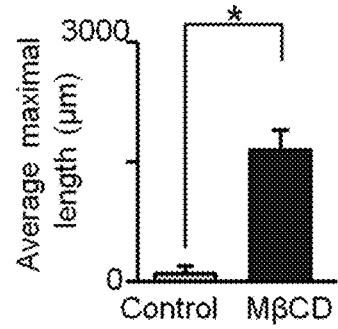

Figure 8
A
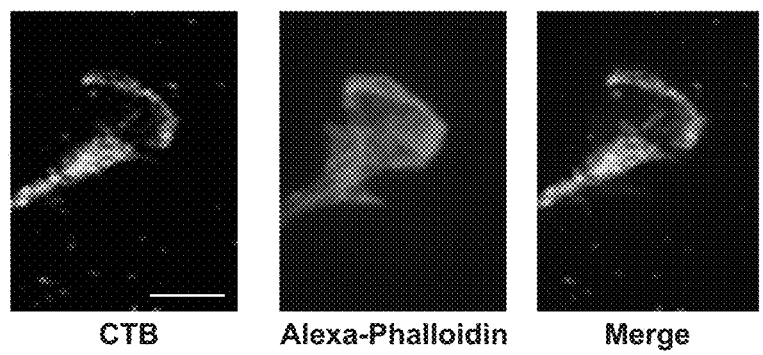
CTB | Alexa-Phalloidin | Merge
B
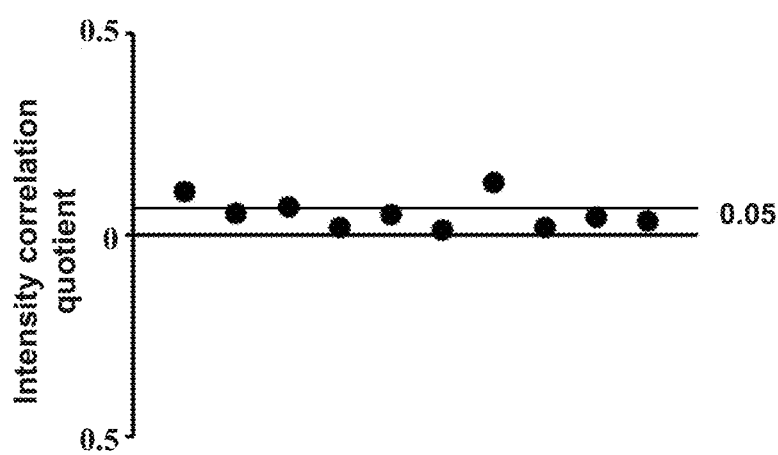
C
Brain fractionation after treatment with MβCD
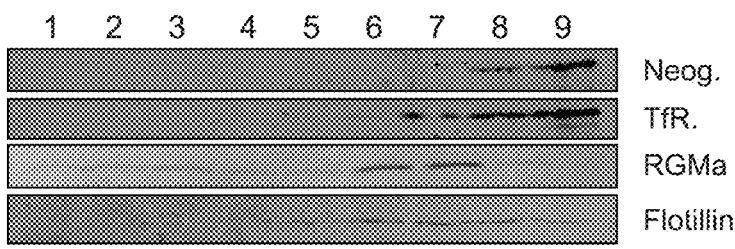

Figure 10
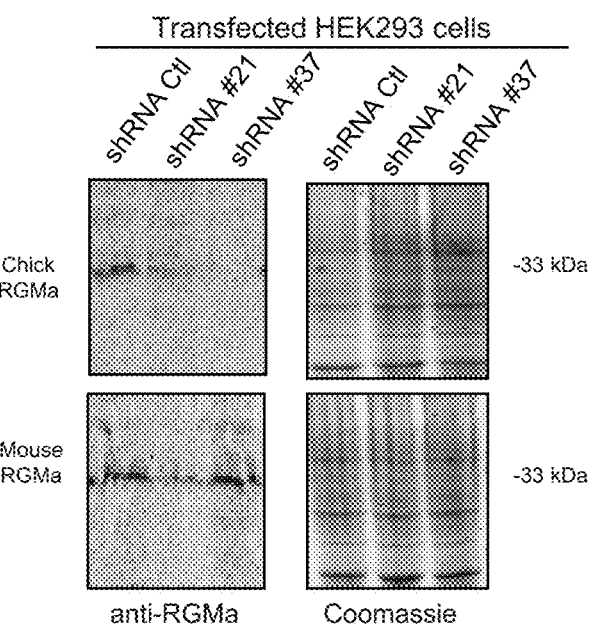
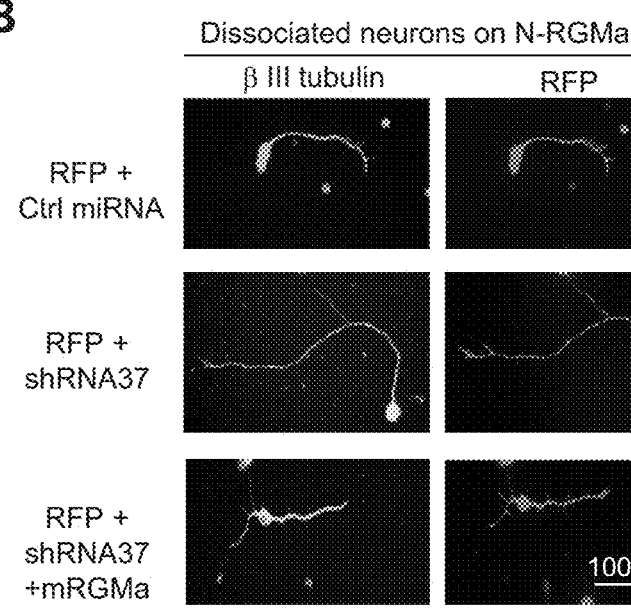

Figure 10 (CONTINUED)
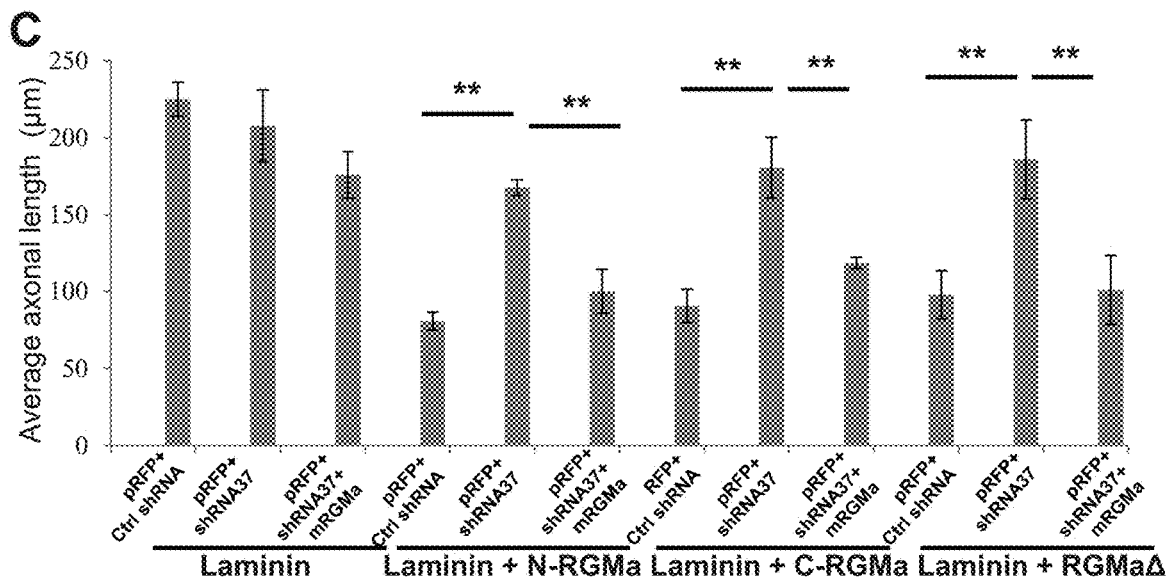
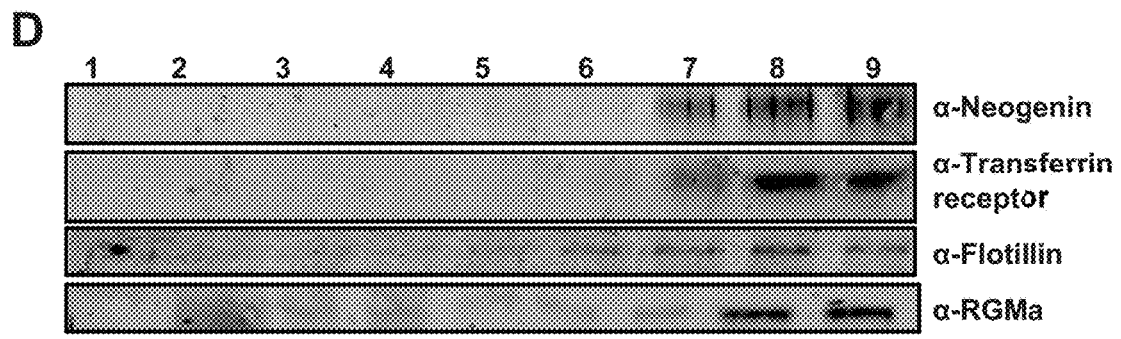
Figure 11
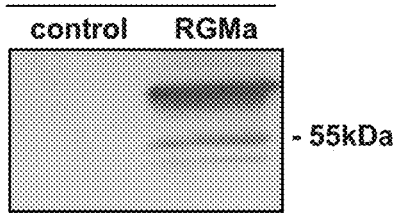
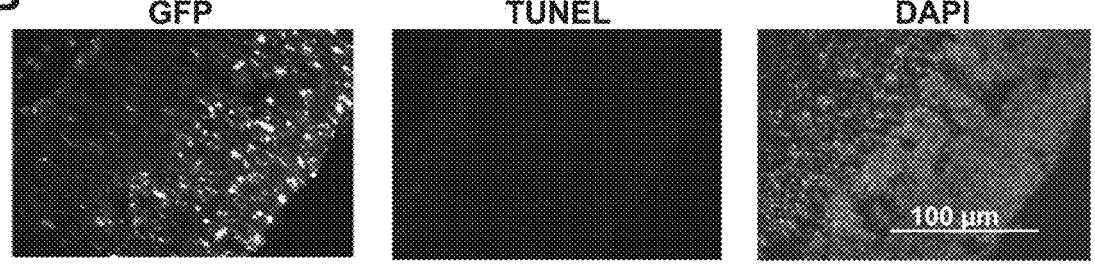

Figure 12
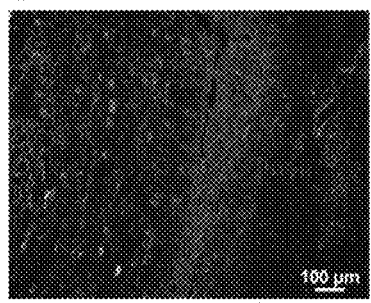
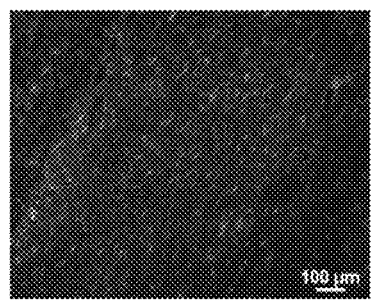
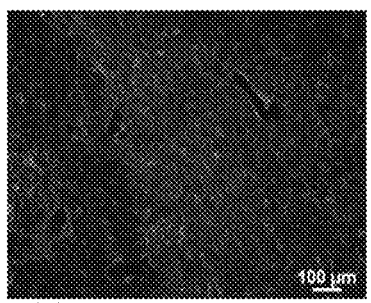
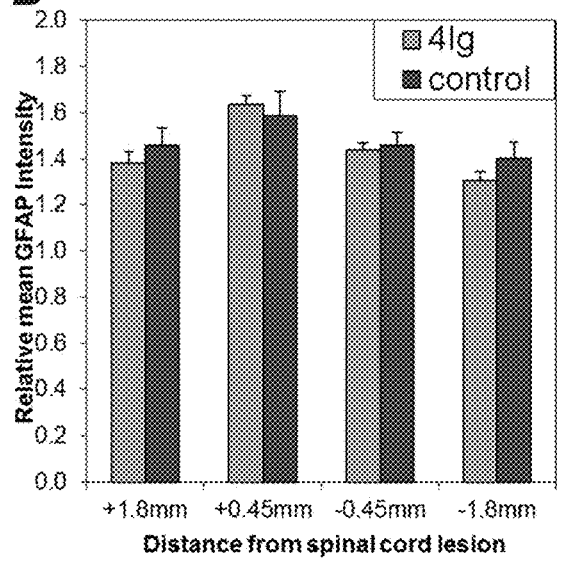
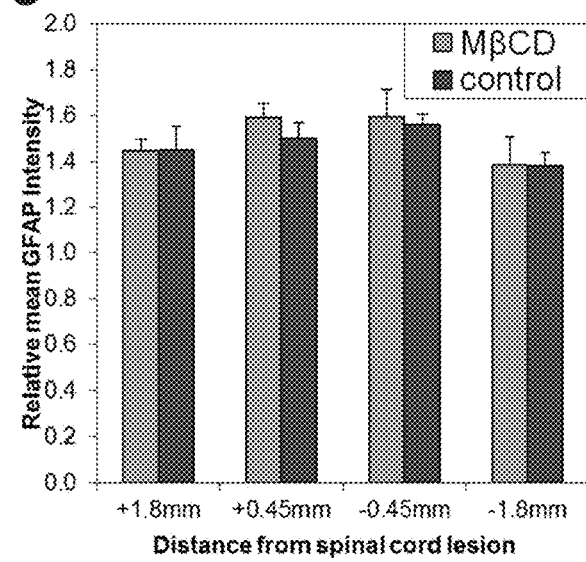
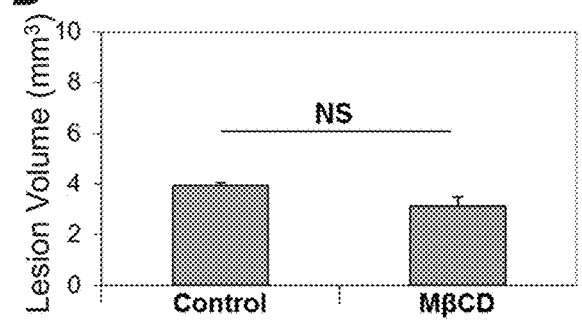
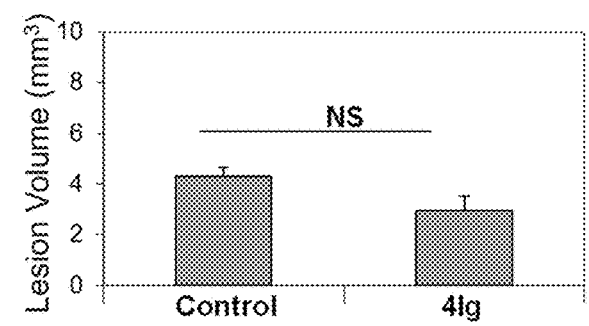
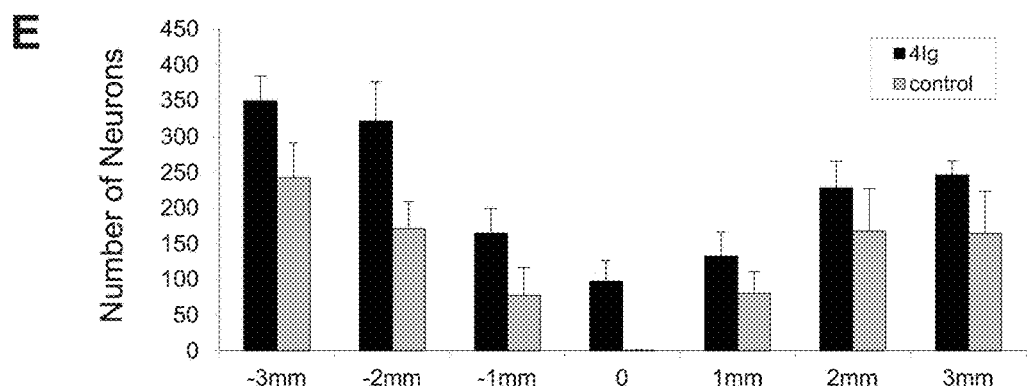

Figure 14
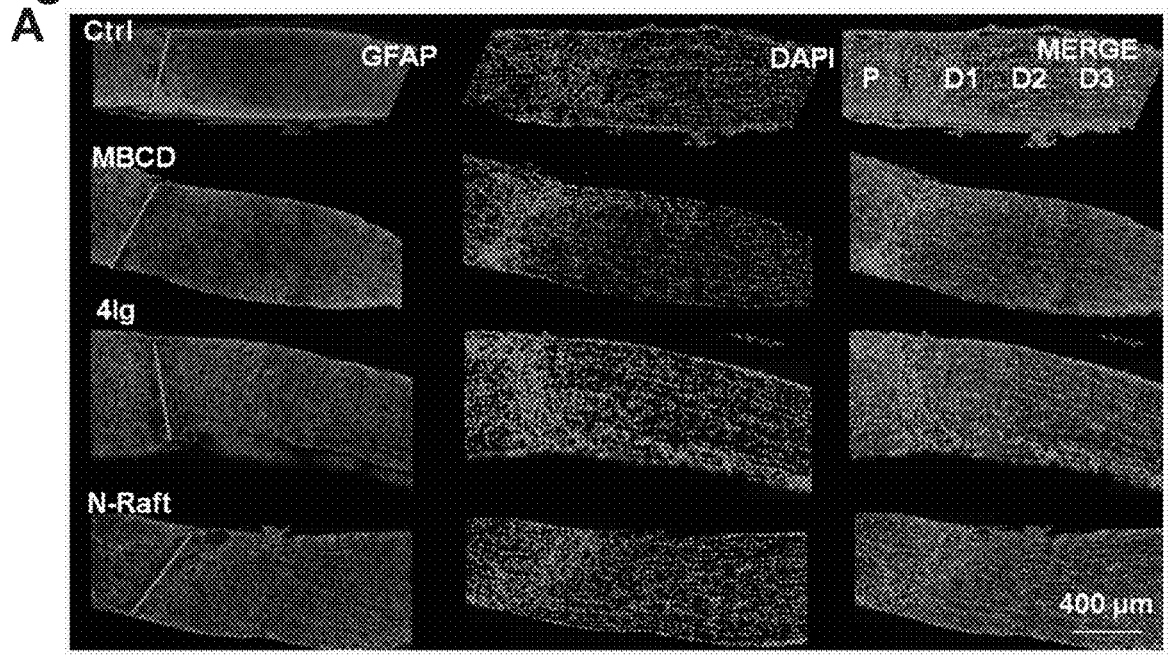
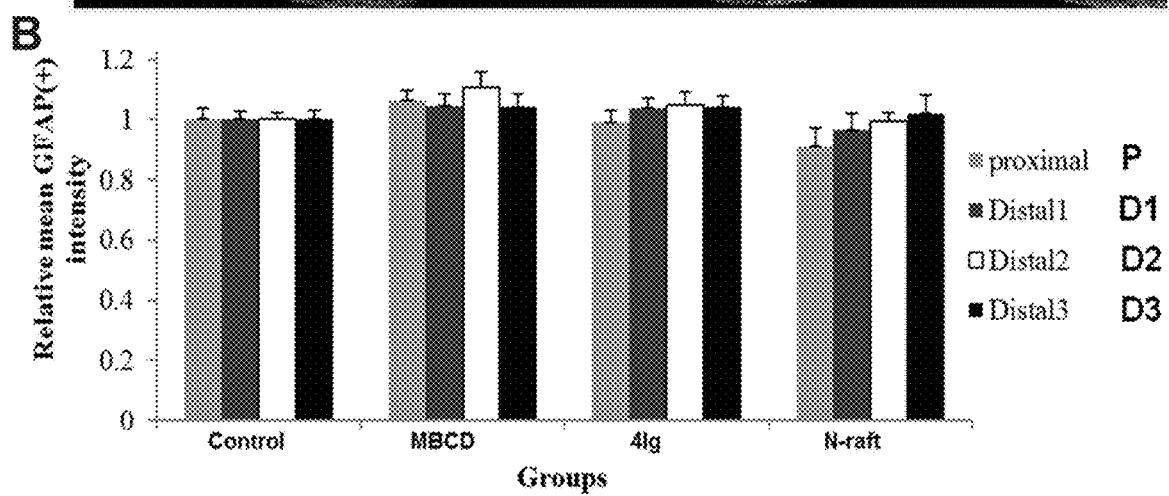
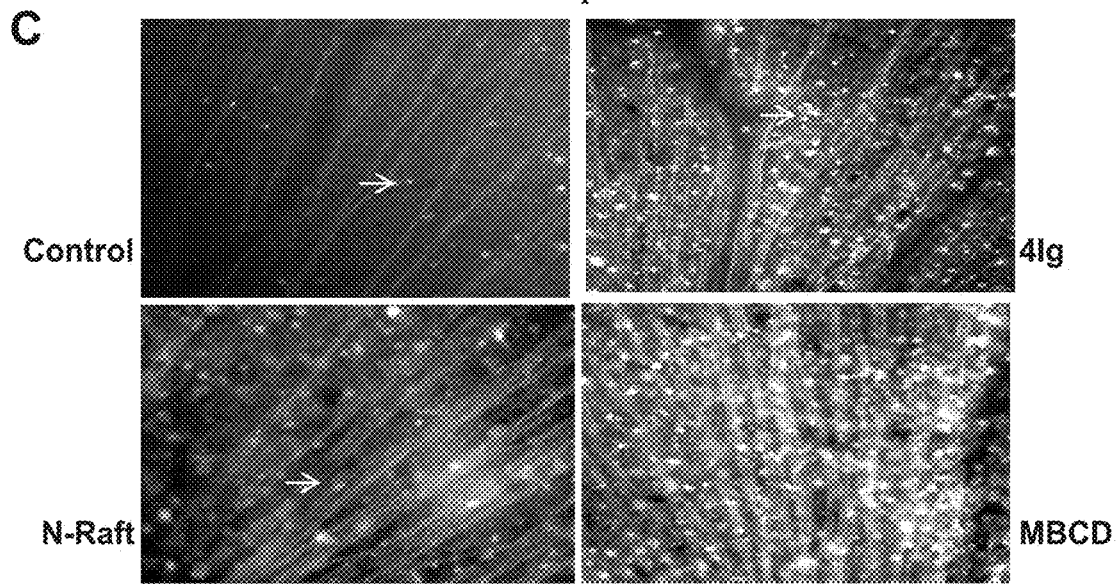

Chicken RGMa (28-73) peptides

Figure 17
A
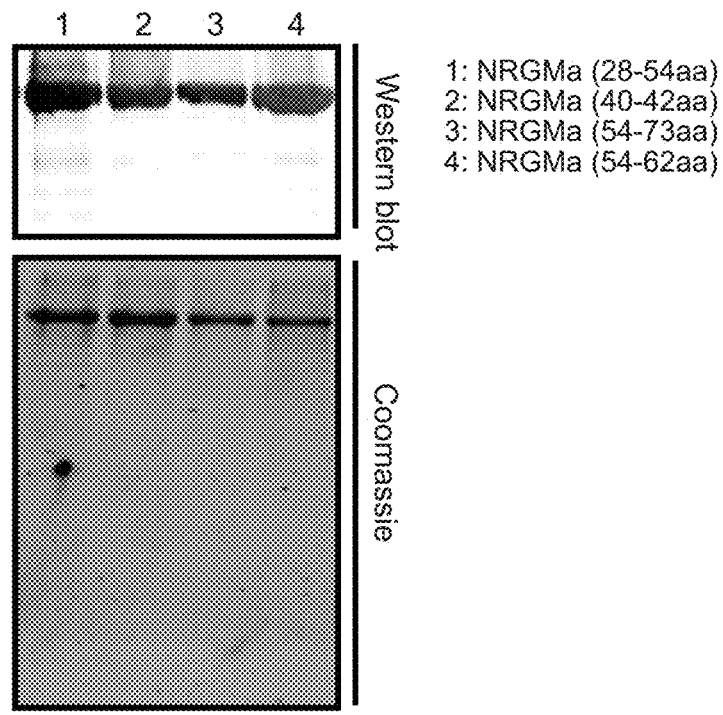
1: NRGMa (28-54aa)
2: NRGMa (40-42aa)
3: NRGMa (54-73aa)
4: NRGMa (54-62aa)
B
C
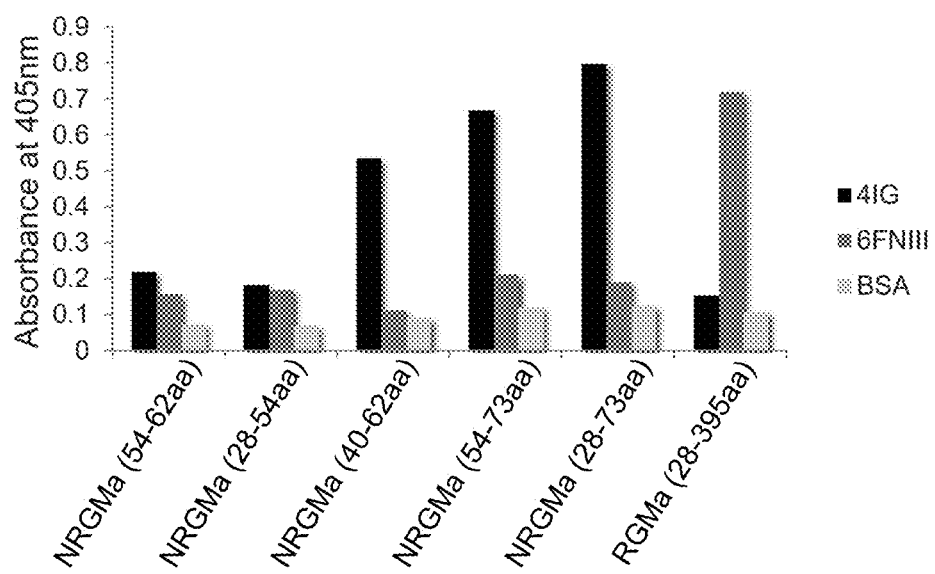

Figure 18
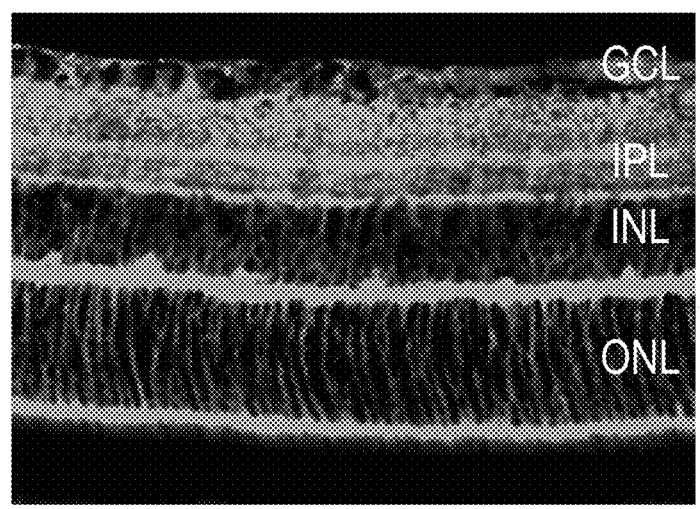
Figure 19
A
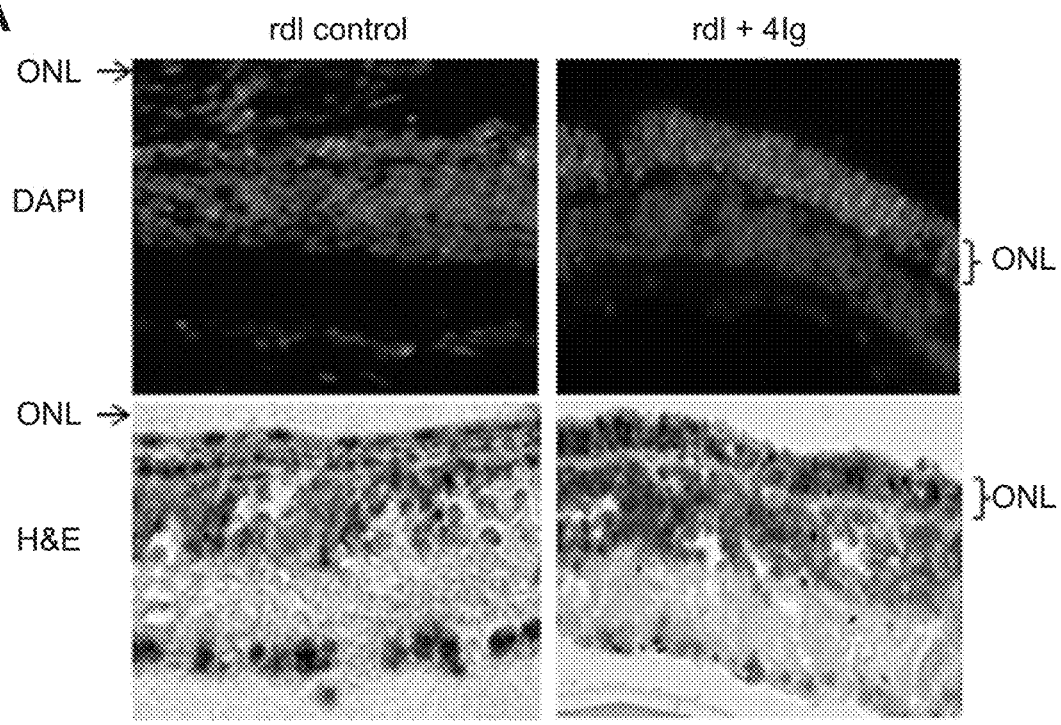
B
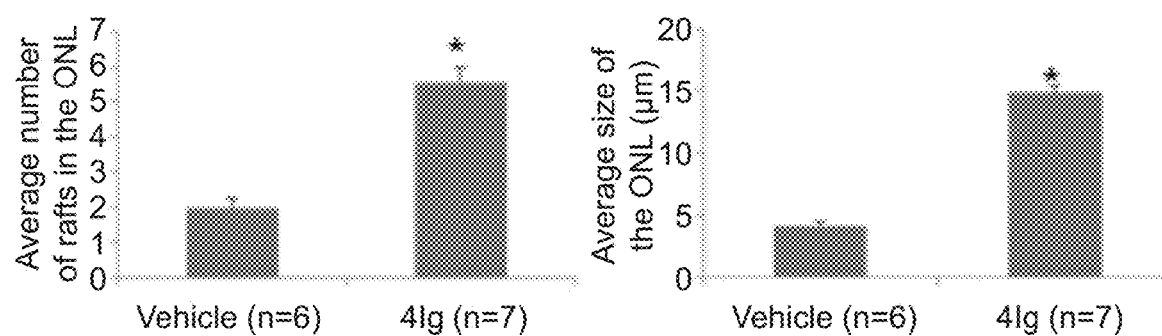

Figure 22
A
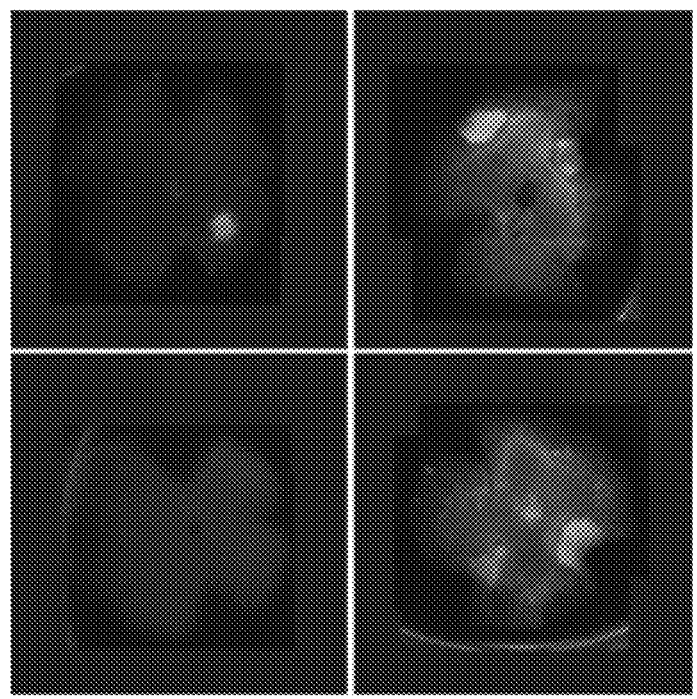
B
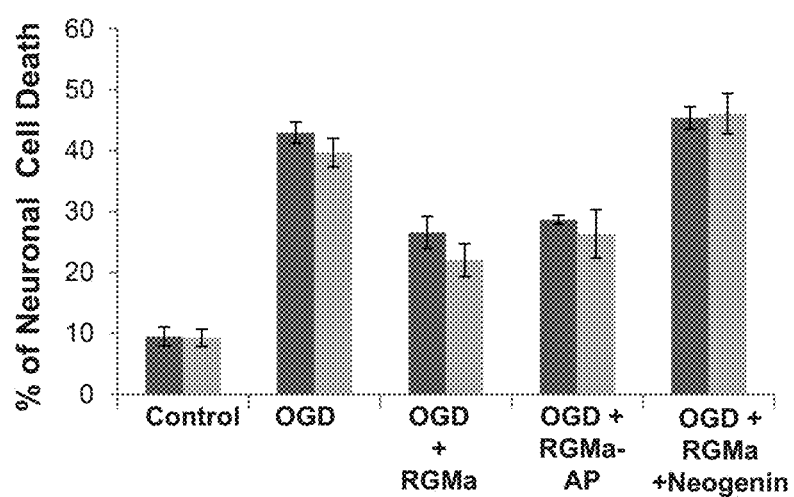

Figure 26
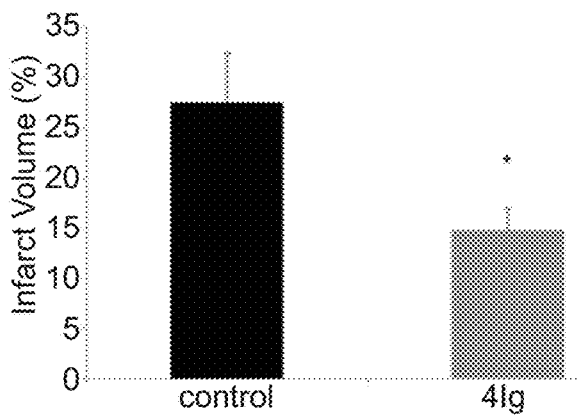
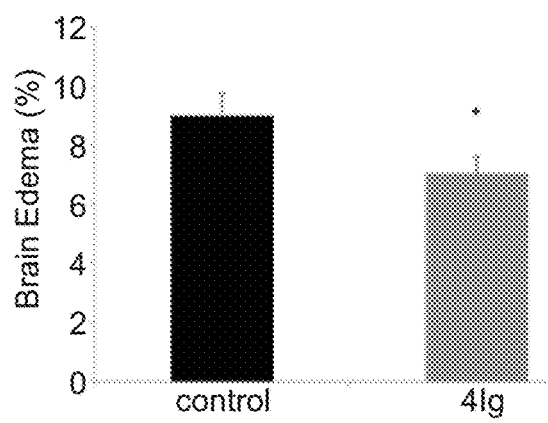
Figure 27
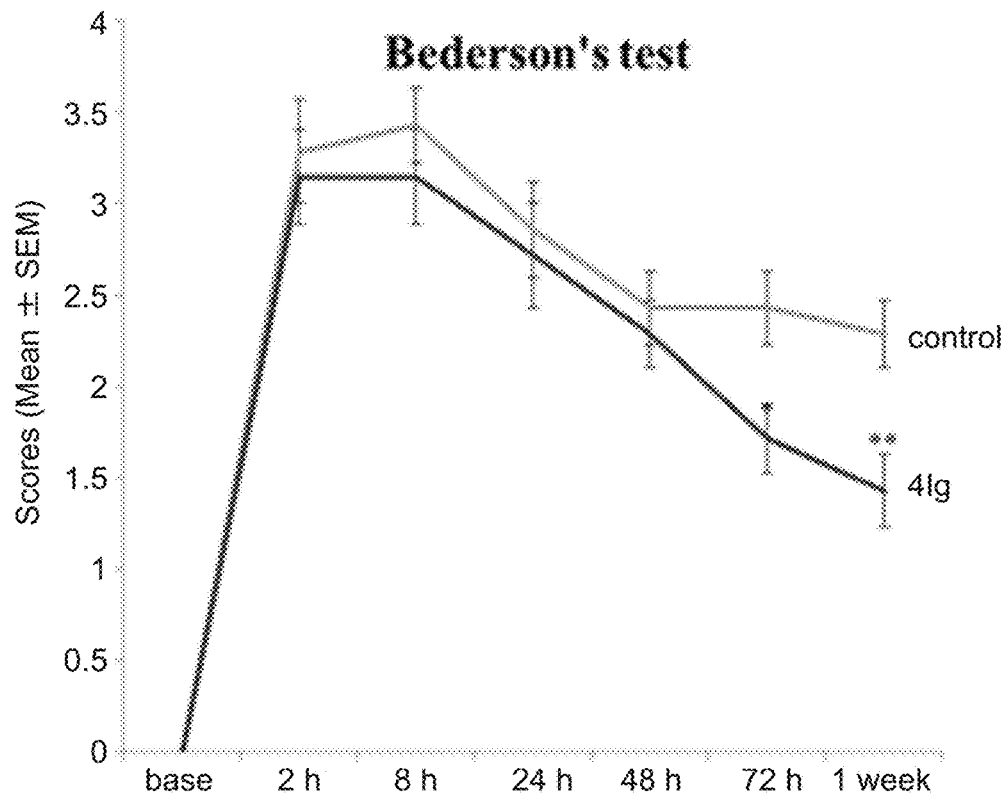

Figure 30
A
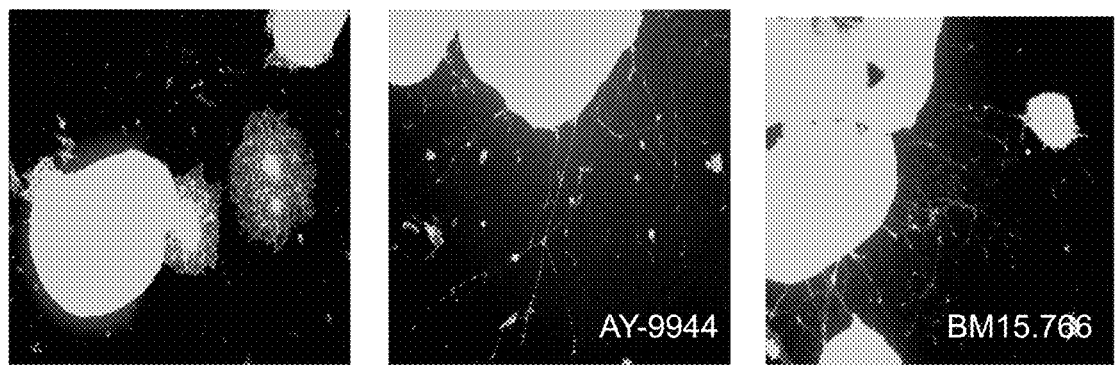
B
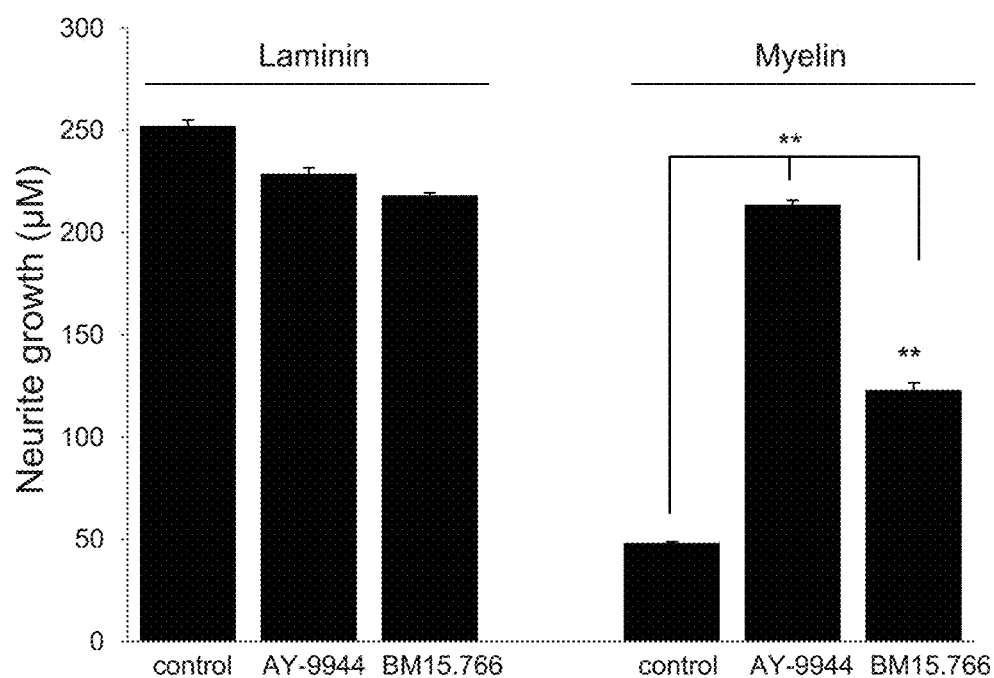

AGENTS DIRECTED AGAINST A CIS RGMA/NEOGENIN INTERACTION OR LIPID RAFTS AND USE OF THE SAME IN METHODS OF TREATMENT

CROSS REFERENCE To RELATED APPLICATION

This application claims priority to U.S. Provisional Patent Application No. 61/878,827, filed Sep. 17, 2013, which is hereby incorporated by reference.

TECHNICAL FIELD

The present invention relates to agents that block a cis interaction between Repulsive Guidance Molecule A (RGMa) and Neogenin or disrupt lipid rafts, methods for modulating this cis interaction or lipid rafts to promote cell survival and axon growth and/or regeneration, and methods of treating a disease in which the cis interaction or lipid rafts are detrimental to a subject, for example, retinitis pigmentosa, multiple sclerosis, ischemia (e.g., stroke), optic nerve injury, and spinal cord injury.

BACKGROUND

Injury to the central nervous system (CNS) may result in permanent loss of function given the poor capacity of adult neurons to regenerate axons. Additionally, adult neurons are susceptible to apoptosis upon injury. In response to injury, the level of Repulsive Guidance Molecule A (RGMa) increases in the CNS. This increased level of RGMa inhibits axonal growth and/or regeneration and promotes neuronal cell survival. As such, RGMa exerts positive and negative effects on the injured CNS. These effects also occur during CNS development.

RGMa mediates this inhibition of axon growth and/or regeneration and promotion of cell survival via a trans interaction with Neogenin. This trans interaction occurs between extracellular RGMa and Neogenin located at the surface of neurons.

Accordingly, a need exists for the identification and development of therapies that both promote neuronal cell survival and axon growth and/or regeneration in the presence of injury to or disease of the CNS.

SUMMARY

The present invention is directed to an agent that promotes both (i) neuronal cell survival and (ii) axon growth and/or axon regeneration.

The present invention is also directed to an agent that promotes both (i) neuronal cell survival and (ii) axon growth and/or axon regeneration, wherein the agent may disrupt lipid rafts.

The present invention is also directed to an agent that promotes both (i) neuronal cell survival and (ii) axon growth and/or axon regeneration, wherein the agent may disrupt a cis interaction between Repulsive Guidance Molecule A (RGMa) and Neogenin.

The present invention is also directed to an agent that promotes both (i) neuronal cell survival and (ii) axon growth and/or axon regeneration, wherein the agent may be a peptide agent, an antibody, a cholesterol-lowering agent, or any combination thereof.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, and wherein the agent may be the peptide agent.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the peptide agent, and wherein the peptide agent may comprise an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, an amino acid sequence as set forth in SEQ ID NO:10, and any combination thereof.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the peptide agent, wherein the peptide agent may comprise an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, an amino acid sequence as set forth in SEQ ID NO:10, and any combination thereof, and wherein the peptide agent may comprise the amino acid sequence comprising amino acids 1 to 383 of SEQ ID NO:1.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the peptide agent, wherein the peptide agent may comprise an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, an amino acid sequence as set forth in SEQ ID NO:10, and any combination thereof, and wherein the peptide agent may comprise the amino acid sequence as set forth in SEQ ID NO:2.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the peptide agent, wherein the peptide agent may comprise an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, an amino acid sequence as set forth in SEQ ID NO:10, and any combination thereof, and wherein the peptide agent may comprise the amino acid sequence as set forth in SEQ ID NO:3.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the peptide agent, wherein the peptide agent may comprise an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, an amino acid sequence as set forth in SEQ ID NO:10, and any combination thereof, and wherein the peptide agent may comprise the amino acid sequence as set forth in SEQ ID NO:4.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the peptide agent, wherein the peptide agent may comprise an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, an amino acid sequence as set forth in SEQ ID NO:10, and any combination thereof, and wherein the peptide agent may comprise the amino acid sequence as set forth in SEQ ID NO:7.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the peptide agent, wherein the peptide agent may comprise an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, an amino acid sequence as set forth in SEQ ID NO:10, and any combination thereof, and wherein the peptide agent may comprise the amino acid sequence as set forth in SEQ ID NO:8.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the peptide agent, wherein the peptide agent may comprise an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, an amino acid sequence as set forth in SEQ ID NO:10, and any combination thereof, and wherein the peptide agent may comprise the amino acid sequence as set forth in SEQ ID NO:9.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the peptide agent, wherein the peptide agent may comprise an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, an amino acid sequence as set forth in SEQ ID NO:10, and any combination thereof, and wherein the peptide agent may comprise the amino acid sequence as set forth in SEQ ID NO:10.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the peptide agent, wherein the peptide agent may comprise an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, an amino acid sequence as set forth in SEQ ID NO:10, and any combination thereof, and wherein the peptide agent may disrupt a cis interaction between Repulsive Guidance Molecule A (RGMa) and Neogenin, thereby blocking recruitment of Neogenin to lipid rafts.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, and wherein the agent may be the antibody.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the antibody, and wherein antibody may specifically bind an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, and an amino acid sequence as set forth in SEQ ID NO:10.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the antibody, wherein antibody may specifically bind an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, and an amino acid sequence as set forth in SEQ ID NO:10, and wherein the antibody may specifically bind the amino acid sequence comprising amino acids 1 to 383 of SEQ ID NO:1.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the antibody, wherein antibody may specifically bind an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, and an amino acid sequence as set forth in SEQ ID NO:10, and wherein the antibody may specifically bind the amino acid sequence as set forth in SEQ ID NO:2.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the antibody, wherein antibody may specifically bind an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, and an amino acid sequence as set forth in SEQ ID NO:10, and wherein the antibody may specifically bind the amino acid sequence as set forth in SEQ ID NO:3.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the antibody, wherein antibody may specifically bind an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, and an amino acid sequence as set forth in SEQ ID NO:10, and wherein the antibody may specifically bind the amino acid sequence as set forth in SEQ ID NO:4.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the antibody, wherein antibody may specifically bind an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, and an amino acid sequence as set forth in SEQ ID NO:10, and wherein the antibody may specifically bind the amino acid sequence as set forth in SEQ ID NO:7.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the antibody, wherein antibody may specifically bind an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, and an amino acid sequence as set forth in SEQ ID NO:10, and wherein the antibody may specifically bind the amino acid sequence as set forth in SEQ ID NO:8.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the antibody, wherein antibody may specifically bind an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, and an amino acid sequence as set forth in SEQ ID NO:10, and wherein the antibody may specifically bind the amino acid sequence as set forth in SEQ ID NO:9.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the antibody, wherein antibody may specifically bind an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, and an amino acid sequence as set forth in SEQ ID NO:10, and wherein the antibody may specifically bind the amino acid sequence as set forth in SEQ ID NO:10.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the antibody, wherein antibody may specifically bind an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, and an amino acid sequence as set forth in SEQ ID NO:10, and wherein the antibody may disrupt a cis interaction between Repulsive Guidance Molecule A (RGMa) and Neogenin, thereby blocking recruitment of Neogenin to lipid rafts.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, and wherein the agent may be the cholesterol-lowering agent.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the cholesterol-lowering agent, and wherein the cholesterol-lowering agent may be selected from the group consisting of: methyl-β-cyclodextrin (MβCD), cholesterol oxidase (CO), AY-9944, a statin, a subtisilin/kexin type 9 (PCK9) inhibitor, nystatin, filipin, proprotein convertase, BM15.766, an alkylphospholipid analog, and any combination thereof.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the cholesterol-lowering agent, wherein the cholesterol-lowering agent may be selected from the group consisting of: methyl-β-cyclodextrin (MβCD), cholesterol oxidase (CO), AY-9944, a statin, a subtisilin/kexin type 9 (PCK9) inhibitor, nystatin, filipin, proprotein convertase, BM15.766, an alkylphospholipid analog, and any combination thereof, and wherein the cholesterol-lowering agent may disrupt lipid rafts, thereby disrupting recruitment of Neogenin to lipid rafts.

The present invention is also directed to a method of treating a disease in a subject in need thereof, the method comprising administering an agent that promotes both (i) neuronal cell survival and (ii) axon growth and/or axon regeneration to the subject.

The present invention is also directed to a method of treating a disease in a subject in need thereof, the method comprising administering an agent that promotes both (i) neuronal cell survival and (ii) axon growth and/or axon regeneration to the subject, wherein the disease may be selected from the group consisting of: retinitis pigmentosa, ischemia, multiple sclerosis, spinal cord injury, and optic nerve injury.

The present invention is also directed to a method of treating a disease in a subject in need thereof, the method comprising administering an agent that promotes both (i) neuronal cell survival and (ii) axon growth and/or axon regeneration to the subject, wherein the disease may be selected from the group consisting of: retinitis pigmentosa, ischemia, multiple sclerosis, spinal cord injury, and optic nerve injury, and wherein the ischemia may be stroke.

The present invention is also directed to a method of treating a disease in a subject in need thereof, the method comprising administering an agent that promotes both (i) neuronal cell survival and (ii) axon growth and/or axon regeneration to the subject, wherein the agent may be a peptide agent, an antibody, a cholesterol-lowering agent, or any combination thereof.

The present invention is also directed to a method of treating a disease in a subject in need thereof, the method comprising administering an agent that promotes both (i) neuronal cell survival and (ii) axon growth and/or axon regeneration to the subject, wherein the agent may be a peptide agent, an antibody, a cholesterol-lowering agent, or any combination thereof, wherein the agent may be the peptide agent, and wherein the peptide agent may comprise an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, an amino acid sequence as set forth in SEQ ID NO:10, and any combination thereof.

The present invention is also directed to a method of treating a disease in a subject in need thereof, the method comprising administering an agent that promotes both (i) neuronal cell survival and (ii) axon growth and/or axon regeneration to the subject, wherein the agent may be a peptide agent, an antibody, a cholesterol-lowering agent, or any combination thereof, wherein the agent may be the cholesterol-lowering agent, and wherein the cholesterol-lowering agent may be selected from the group consisting of: methyl-β-cyclodextrin (MβCD), cholesterol oxidase (CO), AY-9944, a statin, a subtisilin/kexin type 9 (PCK9) inhibitor, nystatin, filipin, proprotein convertase, BM15.766, an alkylphospholipid analog, and any combination thereof.

The present invention is also directed to a method of treating a disease in a subject in need thereof, the method comprising administering an agent that promotes both (i) neuronal cell survival and (ii) axon growth and/or axon regeneration to the subject, wherein the agent may be a peptide agent, an antibody, a cholesterol-lowering agent, or any combination thereof, wherein the agent may be the antibody, and wherein the antibody may specifically bind an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, and an amino acid sequence as set forth in SEQ ID NO:7.

The present invention is also directed to a method of treating a disease in a subject in need thereof, the method comprising administering an agent that promotes both (i) neuronal cell survival and (ii) axon growth and/or axon regeneration to the subject, and further comprising disrupting the cis interaction between RGMa and Neogenin.

The present invention is also directed to a method of treating a disease in a subject in need thereof, the method comprising administering an agent that promotes both (i) neuronal cell survival and (ii) axon growth and/or axon regeneration to the subject, and further comprising disrupting lipid rafts.

The present invention is also directed to a method of treating a disease in a subject in need thereof, the method comprising administering an agent that promotes both (i) neuronal cell survival and (ii) axon growth and/or axon regeneration to the subject, wherein the disease may be selected from the group consisting of: retinitis pigmentosa, ischemia, multiple sclerosis, spinal cord injury, and optic nerve injury, wherein the disease may be spinal cord injury, and wherein the method may further comprise restoring locomoter function in the subject.

The present invention is also directed to a method of treating a disease in a subject in need thereof, the method comprising administering an agent that promotes both (i) neuronal cell survival and (ii) axon growth and/or axon regeneration to the subject, wherein the disease may be selected from the group consisting of: retinitis pigmentosa, ischemia, multiple sclerosis, spinal cord injury, and optic nerve injury, wherein the disease may be retinitis pigmentosa, and wherein the method may further comprise promoting survival of photoreceptor cells in the subject.

The present invention is also directed to a method of treating a disease in a subject in need thereof, the method comprising administering an agent that promotes both (i) neuronal cell survival and (ii) axon growth and/or axon regeneration to the subject, wherein the disease may be selected from the group consisting of: retinitis pigmentosa, ischemia, multiple sclerosis, spinal cord injury, and optic nerve injury, wherein the ischemia may be stroke, and wherein the method may further comprise reducing at least one of infarct volume, brain edema, or a combination thereof in the subject.

The present invention is also directed to a method of identifying an agent that modulates a cis interaction between Repulsive Guidance Molecule A (RGMa) and Neogenin, the method comprising: (a) forming a mixture comprising a RGM peptide and a Neogenin peptide, wherein the RGM peptide comprises an amino acid sequence selected from the group consisting of: an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:9, and an amino acid sequence as set forth in SEQ ID NO:10, and wherein the Neogenin peptide comprises an amino acid sequence selected from the group consisting of: an amino acid sequence comprising amino acids 1 to 383 of SEQ ID NO:1, an amino acid sequence comprising amino acids 1 to 417 of SEQ ID NO:11, and an amino acid sequence as set forth in SEQ ID NO:8; (b) incubating the mixture in the presence of the agent; and (c) detecting in the incubated mixture of step (b) a level of specific binding between the RGM peptide and the Neogenin peptide, wherein a difference in the detected level of specific binding of the RGM peptide to the Neogenin peptide in the presence of the agent relative to a level of specific binding of the RGM peptide to the Neogenin peptide in the absence of the agent indicates that agent modulates the cis interaction.

The present invention is also directed to a method of identifying an agent that modulates a cis interaction between Repulsive Guidance Molecule A (RGMa) and Neogenin, the method comprising: (a) forming a mixture comprising a RGM peptide and a Neogenin peptide, wherein the RGM peptide comprises an amino acid sequence selected from the group consisting of: an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:9, and an amino acid sequence as set forth in SEQ ID NO:10, and wherein the Neogenin peptide comprises an amino acid sequence selected from the group consisting of: an amino acid sequence comprising amino acids 1 to 383 of SEQ ID NO:1, an amino acid sequence comprising amino acids 1 to 417 of SEQ ID NO:11, and an amino acid sequence as set forth in SEQ ID NO:8; (b) incubating the mixture in the presence of the agent; and (c) detecting in the incubated mixture of step (b) a level of specific binding between the RGM peptide and the Neogenin peptide, wherein a difference in the detected level of specific binding of the RGM peptide to the Neogenin peptide in the presence of the agent relative to a level of specific binding of the RGM peptide to the Neogenin peptide in the absence of the agent indicates that agent modulates the cis interaction, wherein the agent may be an antibody or an antibody fragment.

The present invention is also directed to a method of identifying an agent that modulates a cis interaction between Repulsive Guidance Molecule A (RGMa) and Neogenin, the method comprising: (a) forming a mixture comprising a RGM peptide and a Neogenin peptide, wherein the RGM peptide comprises an amino acid sequence selected from the group consisting of: an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:9, and an amino acid sequence as set forth in SEQ ID NO:10, and wherein the Neogenin peptide comprises an amino acid sequence selected from the group consisting of: an amino acid sequence comprising amino acids 1 to 383 of SEQ ID NO:1, an amino acid sequence comprising amino acids 1 to 417 of SEQ ID NO:11, and an amino acid sequence as set forth in SEQ ID NO:8; (b) incubating the mixture in the presence of the agent; and (c) detecting in the incubated mixture of step (b) a level of specific binding between the RGM peptide and the Neogenin peptide, wherein a difference in the detected level of specific binding of the RGM peptide to the Neogenin peptide in the presence of the agent relative to a level of specific binding of the RGM peptide to the Neogenin peptide in the absence of the agent indicates that agent modulates the cis interaction, wherein the RGM peptide may be a RGMa peptide and may be the amino acid sequence as set forth in SEQ ID NO:2.

The present invention is also directed to a method of identifying an agent that modulates a cis interaction between Repulsive Guidance Molecule A (RGMa) and Neogenin, the method comprising: (a) forming a mixture comprising a RGM peptide and a Neogenin peptide, wherein the RGM peptide comprises an amino acid sequence selected from the group consisting of: an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:9, and an amino acid sequence as set forth in SEQ ID NO:10, and wherein the Neogenin peptide comprises an amino acid sequence selected from the group consisting of: an amino acid sequence comprising amino acids 1 to 383 of SEQ ID NO:1, an amino acid sequence comprising amino acids 1 to 417 of SEQ ID NO:11, and an amino acid sequence as set forth in SEQ ID NO:8; (b) incubating the mixture in the presence of the agent; and (c) detecting in the incubated mixture of step (b) a level of specific binding between the RGM peptide and the Neogenin peptide, wherein a difference in the detected level of specific binding of the RGM peptide to the Neogenin peptide in the presence of the agent relative to a level of specific binding of the RGM peptide to the Neogenin peptide in the absence of the agent indicates that agent modulates the cis interaction, wherein the RGM peptide may be a RGMa peptide and may be the amino acid sequence as set forth in SEQ ID NO:3.

The present invention is also directed to a method of identifying an agent that modulates a cis interaction between Repulsive Guidance Molecule A (RGMa) and Neogenin, the method comprising: (a) forming a mixture comprising a RGM peptide and a Neogenin peptide, wherein the RGM peptide comprises an amino acid sequence selected from the group consisting of: an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:9, and an amino acid sequence as set forth in SEQ ID NO:10, and wherein the Neogenin peptide comprises an amino acid sequence selected from the group consisting of: an amino acid sequence comprising amino acids 1 to 383 of SEQ ID NO:1, an amino acid sequence comprising amino acids 1 to 417 of SEQ ID NO:11, and an amino acid sequence as set forth in SEQ ID NO:8; (b) incubating the mixture in the presence of the agent; and (c) detecting in the incubated mixture of step (b) a level of specific binding between the RGM peptide and the Neogenin peptide, wherein a difference in the detected level of specific binding of the RGM peptide to the Neogenin peptide in the presence of the agent relative to a level of specific binding of the RGM peptide to the Neogenin peptide in the absence of the agent indicates that agent modulates the cis interaction, wherein the RGM peptide may be a RGMa peptide and may be the amino acid sequence as set forth in SEQ ID NO:4.

The present invention is also directed to a method of identifying an agent that modulates a cis interaction between Repulsive Guidance Molecule A (RGMa) and Neogenin, the method comprising: (a) forming a mixture comprising a RGM peptide and a Neogenin peptide, wherein the RGM peptide comprises an amino acid sequence selected from the group consisting of: an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:9, and an amino acid sequence as set forth in SEQ ID NO:10, and wherein the Neogenin peptide comprises an amino acid sequence selected from the group consisting of: an amino acid sequence comprising amino acids 1 to 383 of SEQ ID NO:1, an amino acid sequence comprising amino acids 1 to 417 of SEQ ID NO:11, and an amino acid sequence as set forth in SEQ ID NO:8; (b) incubating the mixture in the presence of the agent; and (c) detecting in the incubated mixture of step (b) a level of specific binding between the RGM peptide and the Neogenin peptide, wherein a difference in the detected level of specific binding of the RGM peptide to the Neogenin peptide in the presence of the agent relative to a level of specific binding of the RGM peptide to the Neogenin peptide in the absence of the agent indicates that agent modulates the cis interaction, wherein the RGM peptide may be a RGMa peptide and maybe the amino acid sequence as set forth in SEQ ID NO:7.

The present invention is also directed to a method of identifying an agent that modulates a cis interaction between Repulsive Guidance Molecule A (RGMa) and Neogenin, the method comprising: (a) forming a mixture comprising a RGM peptide and a Neogenin peptide, wherein the RGM peptide comprises an amino acid sequence selected from the group consisting of: an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:9, and an amino acid sequence as set forth in SEQ ID NO:10, and wherein the Neogenin peptide comprises an amino acid sequence selected from the group consisting of: an amino acid sequence comprising amino acids 1 to 383 of SEQ ID NO:1, an amino acid sequence comprising amino acids 1 to 417 of SEQ ID NO:11, and an amino acid sequence as set forth in SEQ ID NO:8; (b) incubating the mixture in the presence of the agent; and (c) detecting in the incubated mixture of step (b) a level of specific binding between the RGM peptide and the Neogenin peptide, wherein a difference in the detected level of specific binding of the RGM peptide to the Neogenin peptide in the presence of the agent relative to a level of specific binding of the RGM peptide to the Neogenin peptide in the absence of the agent indicates that agent modulates the cis interaction, wherein the RGM peptide may be a RGMc peptide and may be the amino acid sequence as set forth in SEQ ID NO:9.

The present invention is also directed to a method of identifying an agent that modulates a cis interaction between Repulsive Guidance Molecule A (RGMa) and Neogenin, the method comprising: (a) forming a mixture comprising a RGM peptide and a Neogenin peptide, wherein the RGM peptide comprises an amino acid sequence selected from the group consisting of: an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:9, and an amino acid sequence as set forth in SEQ ID NO:10, and wherein the Neogenin peptide comprises an amino acid sequence selected from the group consisting of: an amino acid sequence comprising amino acids 1 to 383 of SEQ ID NO:1, an amino acid sequence comprising amino acids 1 to 417 of SEQ ID NO:11, and an amino acid sequence as set forth in SEQ ID NO:8; (b) incubating the mixture in the presence of the agent; and (c) detecting in the incubated mixture of step (b) a level of specific binding between the RGM peptide and the Neogenin peptide, wherein a difference in the detected level of specific binding of the RGM peptide to the Neogenin peptide in the presence of the agent relative to a level of specific binding of the RGM peptide to the Neogenin peptide in the absence of the agent indicates that agent modulates the cis interaction, wherein the RGM peptide may be a RGMa peptide and may be the amino acid sequence as set forth in SEQ ID NO:10.

The present invention is also directed to a method of identifying an agent that modulates a cis interaction between Repulsive Guidance Molecule A (RGMa) and Neogenin, the method comprising: (a) forming a mixture comprising a RGM peptide and a Neogenin peptide, wherein the RGM peptide comprises an amino acid sequence selected from the group consisting of: an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:9, and an amino acid sequence as set forth in SEQ ID NO:10, and wherein the Neogenin peptide comprises an amino acid sequence selected from the group consisting of: an amino acid sequence comprising amino acids 1 to 383 of SEQ ID NO:1, an amino acid sequence comprising amino acids 1 to 417 of SEQ ID NO:11, and an amino acid sequence as set forth in SEQ ID NO:8; (b) incubating the mixture in the presence of the agent; and (c) detecting in the incubated mixture of step (b) a level of specific binding between the RGM peptide and the Neogenin peptide, wherein a difference in the detected level of specific binding of the RGM peptide to the Neogenin peptide in the presence of the agent relative to a level of specific binding of the RGM peptide to the Neogenin peptide in the absence of the agent indicates that agent modulates the cis interaction, wherein the Neogenin peptide may be amino acids 1 to 383 of SEQ ID NO:1.

The present invention is also directed to a method of identifying an agent that modulates a cis interaction between Repulsive Guidance Molecule A (RGMa) and Neogenin, the method comprising: (a) forming a mixture comprising a RGM peptide and a Neogenin peptide, wherein the RGM peptide comprises an amino acid sequence selected from the group consisting of: an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:9, and an amino acid sequence as set forth in SEQ ID NO:10, and wherein the Neogenin peptide comprises an amino acid sequence selected from the group consisting of: an amino acid sequence comprising amino acids 1 to 383 of SEQ ID NO:1, an amino acid sequence comprising amino acids 1 to 417 of SEQ ID NO:11, and an amino acid sequence as set forth in SEQ ID NO:8; (b) incubating the mixture in the presence of the agent; and (c) detecting in the incubated mixture of step (b) a level of specific binding between the RGM peptide and the Neogenin peptide, wherein a difference in the detected level of specific binding of the RGM peptide to the Neogenin peptide in the presence of the agent relative to a level of specific binding of the RGM peptide to the Neogenin peptide in the absence of the agent indicates that agent modulates the cis interaction, wherein the Neogenin peptide may be the amino acid sequence as set forth in SEQ ID NO:8.

The present invention is also directed to a method of identifying an agent that modulates a cis interaction between Repulsive Guidance Molecule A (RGMa) and Neogenin, the method comprising: (a) forming a mixture comprising a RGM peptide and a Neogenin peptide, wherein the RGM peptide comprises an amino acid sequence selected from the group consisting of: an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:9, and an amino acid sequence as set forth in SEQ ID NO:10, and wherein the Neogenin peptide comprises an amino acid sequence selected from the group consisting of: an amino acid sequence comprising amino acids 1 to 383 of SEQ ID NO:1, an amino acid sequence comprising amino acids 1 to 417 of SEQ ID NO:11, and an amino acid sequence as set forth in SEQ ID NO:8; (b) incubating the mixture in the presence of the agent; and (c) detecting in the incubated mixture of step (b) a level of specific binding between the RGM peptide and the Neogenin peptide, wherein a difference in the detected level of specific binding of the RGM peptide to the Neogenin peptide in the presence of the agent relative to a level of specific binding of the RGM peptide to the Neogenin peptide in the absence of the agent indicates that agent modulates the cis interaction, wherein modulation may include disrupting the cis interaction between RGMa and Neogenin.

The present invention is also directed to a method of identifying an agent that modulates a cis interaction between Repulsive Guidance Molecule A (RGMa) and Neogenin, the method comprising: (a) forming a mixture comprising a RGM peptide and a Neogenin peptide, wherein the RGM peptide comprises an amino acid sequence selected from the group consisting of: an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:9, and an amino acid sequence as set forth in SEQ ID NO:10, and wherein the Neogenin peptide comprises an amino acid sequence selected from the group consisting of: an amino acid sequence comprising amino acids 1 to 383 of SEQ ID NO:1, an amino acid sequence comprising amino acids 1 to 417 of SEQ ID NO:11, and an amino acid sequence as set forth in SEQ ID NO:8; (b) incubating the mixture in the presence of the agent; and (c) detecting in the incubated mixture of step (b) a level of specific binding between the RGM peptide and the Neogenin peptide, wherein a difference in the detected level of specific binding of the RGM peptide to the Neogenin peptide in the presence of the agent relative to a level of specific binding of the RGM peptide to the Neogenin peptide in the absence of the agent indicates that agent modulates the cis interaction, wherein modulation may include disrupting the cis interaction between RGMa and Neogenin, and wherein if the detected level of specific binding of the RGM peptide to the Neogenin peptide in the presence of the agent is lower than the level of specific binding of the RGM peptide to the Neogenin peptide in the absence of the agent, then the agent disrupts the cis interaction.

The present invention is also directed to a peptide comprising an amino acid sequence having at least about 95% identity to an amino acid sequence comprising amino acids 1 to 383 of SEQ ID NO:1, wherein the peptide disrupts a cis interaction between Repulsive Guidance Molecule A (RGMa) and Neogenin.

The present invention is also directed to a peptide comprising an amino acid sequence having at least about 95% identity to an amino acid sequence as set forth in SEQ ID NO:2, wherein the peptide disrupts a cis interaction between Repulsive Guidance Molecule A (RGMa) and Neogenin.

The present invention is also directed to a peptide comprising an amino acid sequence having at least about 95% identity to an amino acid sequence as set forth in SEQ ID NO:3, wherein the peptide disrupts a cis interaction between Repulsive Guidance Molecule A (RGMa) and Neogenin.

The present invention is also directed to a peptide comprising an amino acid sequence having at least about 95% identity to an amino acid sequence as set forth in SEQ ID NO:4, wherein the peptide disrupts a cis interaction between Repulsive Guidance Molecule A (RGMa) and Neogenin.

The present invention is also directed to a peptide comprising an amino acid sequence having at least about 95% identity to an amino acid sequence as set forth in SEQ ID NO:7, wherein the peptide disrupts a cis interaction between Repulsive Guidance Molecule A (RGMa) and Neogenin.

The present invention is also directed to a peptide comprising an amino acid sequence having at least about 95% identity to an amino acid sequence as set forth in SEQ ID NO:8, wherein the peptide disrupts a cis interaction between Repulsive Guidance Molecule A (RGMa) and Neogenin.

The present invention is also directed a peptide comprising an amino acid sequence having at least about 95% identity to an amino acid sequence as set forth in SEQ ID NO:9, wherein the peptide disrupts a cis interaction between Repulsive Guidance Molecule A (RGMa) and Neogenin.

The present invention is also directed to a peptide comprising an amino acid sequence having at least about 95% identity to an amino acid sequence as set forth in SEQ ID NO:10, wherein the peptide disrupts a cis interaction between Repulsive Guidance Molecule A (RGMa) and Neogenin.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the peptide agent, wherein the peptide agent may comprise an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, an amino acid sequence as set forth in SEQ ID NO:10, and any combination thereof, and wherein the peptide agent may comprise the amino acid sequence comprising amino acids 1 to 417 of SEQ ID NO:11.

The present invention is also directed to an agent that promotes both (i) neuronal cell survival and (ii) axon growth and/or axon regeneration, wherein the agent may be a peptide agent, an antibody, a cholesterol-lowering agent, or any combination thereof, wherein the agent may be the antibody, wherein antibody may specifically bind an amino acid sequence selected from the group consisting of: an amino acid sequence comprising amino acids 1 to 383 of SEQ ID NO:1, an amino acid sequence comprising amino acids 1 to 417 of SEQ ID NO:11, an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:8, an amino acid sequence as set forth in SEQ ID NO:9, and an amino acid sequence as set forth in SEQ ID NO:10, and wherein the antibody may specifically bind the amino acid sequence comprising amino acids 1 to 417 of SEQ ID NO:11.

The present invention is also directed to a method of identifying an agent that modulates a cis interaction between Repulsive Guidance Molecule A (RGMa) and Neogenin, the method comprising: (a) forming a mixture comprising a RGM peptide and a Neogenin peptide, wherein the RGM peptide comprises an amino acid sequence selected from the group consisting of: an amino acid sequence as set forth in SEQ ID NO:2, an amino acid sequence as set forth in SEQ ID NO:3, an amino acid sequence as set forth in SEQ ID NO:4, an amino acid sequence as set forth in SEQ ID NO:7, an amino acid sequence as set forth in SEQ ID NO:9, and an amino acid sequence as set forth in SEQ ID NO:10, and wherein the Neogenin peptide comprises an amino acid sequence selected from the group consisting of: an amino acid sequence comprising amino acids 1 to 383 of SEQ ID NO:1, an amino acid sequence comprising amino acids 1 to 417 of SEQ ID NO:11, and an amino acid sequence as set forth in SEQ ID NO:8; (b) incubating the mixture in the presence of the agent; and (c) detecting in the incubated mixture of step (b) a level of specific binding between the RGM peptide and the Neogenin peptide, wherein a difference in the detected level of specific binding of the RGM peptide to the Neogenin peptide in the presence of the agent relative to a level of specific binding of the RGM peptide to the Neogenin peptide in the absence of the agent indicates that agent modulates the cis interaction, wherein the Neogenin peptide may be amino acids 1 to 417 of SEQ ID NO:11.

The present invention is also directed to a peptide comprising an amino acid sequence having at least about 95% identity to an amino acid sequence comprising amino acids 1 to 417 of SEQ ID NO:11, wherein the peptide disrupts a cis interaction between Repulsive Guidance Molecule A (RGMa) and Neogenin.

BRIEF DESCRIPTION OF THE DRAWINGS

FIG. 8 shows controls for co-localization experiments. (A) CTB and F-actin staining of retinal growth cones. Composite images of the raft marker cholera toxin subunit B (CTB), the F-actin marker Alexa-Phalloidin and merged image, which shows the colocalization overlap of CTB and F-actin (color not shown) in the stem and circumference of the diagram; Bar, 30 µm. (B) CTB and F-actin showed random staining in retinal growth cones. Intensity correlation quotient (ICQ) to quantify co-localization between CTB and Alexa-Phalloidin was calculated as described in 10 growth cones. ICQ reflects the ratio of the number of positive or negative (Ai−a)(Bi−b) values to the total pixel number minus 0.5 to derive a −0.5 to +0.5 range. Here, an average ICQ of 0.05 was computed, which indicates random localization between CTB and F-actin. (C) MβCD treatment of chick brains shifts Neogenin colocalization to heavier fractions. Chick brains were injected with MβCD (10 mM) to deplete cholesterol one day before preparing membrane fractionations. In these experiments, Neogenin co-localized with the transferrin receptor (TfR). Thus, pre-treatment with MβCD altered Neogenin localization, indicating that it was no longer in the lipid raft fraction.

FIG. 10 shows assessment of RGMa silencing using shRNAs. (A) Western Blot analysis of chick and mouse RGMa silencing using RGMa-shRNAs (shRNA #21 and shRNA #37). HEK-293 cells were co-transfected with chick or mouse RGMa and an shRNA. Two days after transfection, membrane preparations were done and RGMa expression analyzed in Western Blots using an anti RGMa antibody. When HEK-293 cells were transfected with chick RGMa, Western Blots analysis revealed that RGMa-shRNAs (shRNA #21 and shRNA #37) but not the Control ShRNA (ShRNA-Crl) silenced RGMa expression. When HEK-293 cells were transfected with mouse RGMa, Western Blots analysis revealed that RGMa-shRNA #21 silenced its expression. However, shRNA #37 did not silence mouse RGMa expression. Therefore, mouse RGMa can be used in rescue experiments in which chick RGMa has been silenced with RGMa shRNA #37. Coomassie staining shows equivalent amount of protein loading. (B) Dissociated retinal ganglion cells were transfected with various constructs and cultured on N-RGMa. Co-transfection with red fluorescent protein was performed to identify transfected cells. Staining for βIII tubulin was done to identify neuronal cells. Representative pictures of RGCs transfected with control shRNA shows inhibition of axonal outgrowth on coverslips coated with N-RGMa. In presence of shRNA37, which silenced chick RGMa, this inhibition was suppressed. When shRNA37 was co-transfected with mouse RGMa, N-RGMa inhibition of axonal growth was restored. (C) Quantification of experiments in which retinal ganglion cells were transfected with various plasmids and grown on laminin and laminin plus N-RGMa, C-RGMa and RGMaΔ. On RGMa proteins, retinal axons were shorter when compared to laminin. These inhibitions were suppressed by shRNA37 transfection and restored when mouse RGMa was co-trancfected with shRNA37. Thus, the effect of shRNA37 results from a specific silencing of RGMa. All data were the mean axonal length±SEM (n=6 independent experiments). Data were average±SEM (n=6 independent experiments), *p<0.01. (D) MβCD treatment of retinal explants changes Neogenin colocalization to heavier fractions. Chick explants were treated MβCD (10 mM) to deplete cholesterol for 1 hour before preparing membrane fractionations. In these experiments, Neogenin co-localized with the transferrin receptor (TfR). Thus, pre-treatment with MβCD altered Neogenin localization, indicating that it was no longer in the lipid raft fraction.

FIG. 11 shows control experiments for the assessment of cell death. (A) RGMa expression in stable HEK-293. A cell line that stably expresses RGMa was generated in HEK-293 cells. Membranes from control and RGMa-expressing stable line were prepared for analysis. Western Blot analysis was performed on samples that were loaded in the absence of DTT (to preserve disulfide bridges). An anti-RGMa antibody reveals the presence of the expected 55 kDa band in the stable cell line. This band was absent in the control. (B) Green fluorescent protein (GFP) electroporation does not cause apoptosis in the chick tectum. E5 tecta were electroporated with a GFP-expressing plasmid and one day later, tecta were removed and apoptotic cell death was determined using TUNEL analysis on sections. The GFP staining indicated that tecta were electroporated successfully. TUNEL staining revealed that GFP electroporation did not induce apoptosis. Thus, electroporation of GFP did not induce apoptotic death.

FIG. 12 shows effect of treatments with MβCD and 4Ig on GFAP and NeuN staining: (A) Representative images showing regions of spinal cord caudal to the lesion site stained with the astrocyte marker, GFAP, from rats treated with MβCD, 4Ig, and control PBS. Insets show high magnification image of GFAP positive astrocytes. (B, C) For each animal, the sum immunofluorescence intensity values of 3 regions ($1.1 \times 10^6$ um$^2$ area) were determined at 0.45 mm and 1.8 mm from the edge of the lesion both rostrally and caudally in 3 sections with equivalent anterior-posterior distance through the thickness of each cord. Mean values from each region per animal were normalized to the mean intensity values of uninjured control and averaged. There is no significant difference between groups. Data were average±SEM (n=5 animals/condition). (D) MBCD or 4Ig treatment did not affect lesion volume. Parasagittal sections were stained with LFB/H&E and the volume of the lesion was calculated in each cord and averaged. There was no significant difference in the volume of the lesion between groups. (E) Host neuronal counts: Intrathecal application of 4Ig was performed over a period of 6 weeks following injury and cross sections of the cord were stained with NeuN. NeuN+ cells were counted in cross-sections separated by a distance of 320 um throughout a 5 mm rostro-caudal segment of spinal cord encompassing the lesion site; top graph shows total of all neurons counted and averaged per group; bottom graph shows average # of neurons counted in rostro-caudal intervals encompassing the lesion site: −3 mm rostral to 0 (epicentre) to 3 mm caudal; 1 way ANOVA, post-hoc Bonferonni.

FIG. 14 shows treatment with 4Ig, N-Raft and MβCD in the injured optic nerve. Optic nerve were submitted to crush injury and treated with DMSO (Control), 4Ig, N-Raft, and MβCD until sacrifice 21 days after injury. Optic nerves were then fixed, sectioned and analyzed with an anti-GFAP antibody to label astroglia cells. (A) Representative pictures of optic nerves treated with DMSO (Control), 4Ig, N-Raft, and MβCD. Panels display GFAP, DAPI and merge staining. The top right panel indicates the areas that have been used for quantification of GFAP staining. (B) For each animal, the immunofluorescence intensity was determined using Image J program (NIH) in the 4 areas presented in (A). The relative mean intensity for each area is presented. There is no significant difference between groups. Data are average±SEM (n=8 animals/condition). (C) Epifluorescence micrographs showing Cholera Toxin B (FITC conjugated) anterograde labeling in flat-mounted retinas at 21 days after optic nerve crush. Each picture is from the mid-periphery after a specific treatment. The cell bodies (arrow) and axons of RGCs that are actively anterogradely transporting CTB-FITC along their axons are visible. MBCD, 4Ig or N-Raft treatments i) preserved the integrity of RGC axonsoma in the nerve fiber layer after optic nerve crush compared to controls. These effects were seen across the entire surface of the retina, from mid-periphery to the outer retina.

FIG. 17 shows (A) a western blot and its corresponding Coomassie stained gel; (B) a schematic of the RGMa peptides; and (C) peptide plotted against absorbance at 450 nm. All constructs used in this study were generated from the Gallus gallus species. To identify the binding site of N-RGMa to the 4Ig domain of Neogenin, N-RGMa (28-73aa) was divided into four overlapping fragments: 1) N-RGMa (28-54aa); 2) N-RGMa (40-62aa); 3) N-RGMa (55-73aa), and 4) N-RGMa (54-62aa). The sequences were cloned in the Psectag2B-AP plasmid, which allows for secretion of the peptides, as soluble proteins, fused with an alkaline phosphatase tag. Using a 96-well microtiter plate (Corning Incorporated), wells were coated with 100 µl (10 µg/mL) of Poly-L-Lysine at 4° C. overnight. Wells were then washed three times with 100 µl of PBST (+0.02% Tween). 50 µl (2.5 µg/mL) of His-tagged: Full-length Neogenin; 4 Ig Neogenin; and FNIII Neogenin were coated onto each well for 1 hour at 37° C. Following three washes of 100 µl PBST, each well was then blocked with 300 µl of 3% BSA in PB ST for 1 hour at 37° C. 50 µl (1.0 µg/mL) AP-tagged: N-RGMa (28-73); N-RGMa (28-54); N-RGMa (40-62); N-RGMa (54-73); N-RGMa (54-62) in 1% BSA+PB ST was then added to each well and incubated at 37° C. for 1 hour. Each well was washed thoroughly three times with 100 µl PBST followed by subsequent equilibration of each well with Alkaline Phosphatase (AP) developing buffer (100 mM NaHCO$_3$, 1 mM MgCl$_2$). The reaction was developed using AP developing buffer supplemented with, p-nitrophenyl phosphate (pNPP) (Sigma-Aldrich) and allowed to develop until color development. The reaction was stopped with the addition of 50 µl (0.1M) NaOH. The absorbance of each reaction was measured using a microplate autoreader (BIO-TEK Instruments Inc.) at 450 nanometers (nm) wavelength. To further identify the binding site within N-Raft for the 4Ig-domain of Neogenin, N-Raft was divided into four overlapping fragments: N-RGMa (28-54aa); N-RGMa (40-62aa); N-RGMa (55-73aa); and N-RGMa (54-62aa). These four fragments were purified and tested for binding to full-length Neogenin, the 4Ig-domain of Neogenin, and the 6FNIII-domain of Neogenin (FIGS. 17A-17C). These studies demonstrated that N-RGMa (40-62aa) and N-RGMa (54-73aa) bound specifically to the 4Ig-domain of Neogenin (FIG. 17C).

FIG. 18 shows Neogenin is expressed on adult murine photoreceptors: The adult retina was stained with an anti-Neogenin antibody which reveals that this protein is expressed in the Outer Nuclear Layer (ONL) which contains photoreceptors.

FIG. 19 shows the Neogenin 4Ig domain prevents photoreceptor death in rd1 mice: A) Rd1 mice were injected at P9 with PBS (control) or with the 4Ig fragment of Neogenin. At P21 animals were sacrificed and DAPI or H&E staining was performed to visualize photoreceptors. In 4Ig injected animals, the Outer Nuclear Layer (ONL) appeared thicker in when compared to controls. B) Quantification for experiments presented in (A). The number of cells as well as the average thickness of the ONL was significantly increased in 4Ig treated animals vs. controls.

FIG. 22 shows RGMa promotes cell survival through Neogenin in a stroke model: (A) Retinal whole mounts were submitted to oxygen glucose deprivation (OGD) as a model for stroke and propidium iodide staining (red color, color not shown) was performed to assess cell death. In control (no OGD), most of the cells survive. After OGD the increased staining reveals a higher number of dead cells. The addition of RGMa to the medium (OGD+RGMa) reduces cell death. Presence of a Neogenin blocking antibody abolishes the pro-survival effect of RGMa, indicating that RGMa's effect on cell survival is Neogenin-mediated (OGD+RGMa+Neogenin antibody). (B) Quantifications of 4 independent experiments are presented in A.

FIG. 26 shows altering Neogenin association with lipid rafts (4Ig) prevents brain damage after stroke: A blood clot was injected into the middle Cerebral Artery to create a stoke and animals were treated with tail vein injection of 4Ig (daily) and animals or control peptide. Animals were kept for a week and the brain was stained (2% 2,3,5-triphenyltetrazolium chloride solution) to visualize damages. A) The infarct volume was measured in 4Ig and control animals. This shows a significant reduction of infarct size in 4Ig treated animal. B) The size of the brain edema was measured in 4Ig and control animals. This shows a significant decrease of edema size in 4Ig treated animals. (*$p<0.05$)

FIG. 27 shows altering Neogenin association with lipid rafts (4Ig) helps restoring brain functions after stroke: A blood clot was injected into the middle Cerebral Artery to create a stoke and animals were treated with tail vein injection of 4Ig (daily) or control peptide. Animals were kept for a week and functional behavior was assessed using the Bederson test. 4Ig treated animals, showed a significant improvement ($p<0.05$) of brain functions when compared to controls.

FIG. 30 shows inhibiting cholesterol biosynthesis using AY-9944 and BM 15.766 promoted growth of retinal ganglion cell neuritis on myelin. Retinal explants were prepared from E7 chick embryos and cultured on coverslips coated with on Laminin or myelin, and treated with control (DMSO) or AY-9944 (1 μM) or BM15.766 (4 μM). After 18 hrs in culture, explants were fixed with 4% PFA and stained with Alexa488-Phalloidin. Neurites were measured using Cellsens software. Retinal explants were cultured on laminin (control) or myelin (the inhibitory compound of the CNS). On laminin, axon growth was normal compared to myelin because myelin inhibited outgrowth. When cholesterol inhibitors were added to the medium, they did not influence outgrowth on laminin. However, they restored outgrowth on myelin, which indicated that they suppressed the inhibitory activity of myelin.

DETAILED DESCRIPTION

Figure 1:
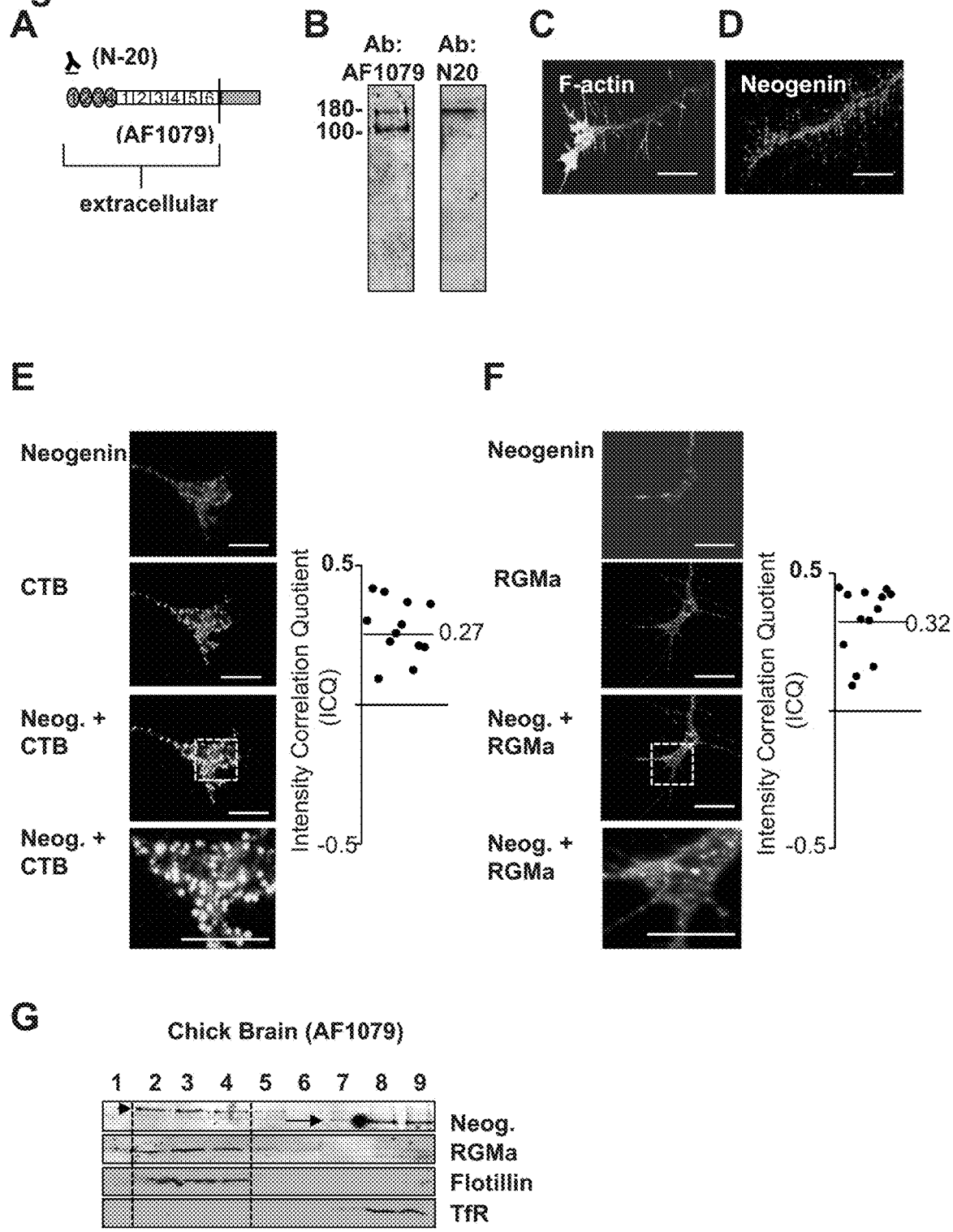
FIG. 1 shows Neogenin was present in lipid rafts. (A) A schematic representation of the sequences used to generate the N-20 and AF1079 antibodies against Neogenin. (B) Western blot analysis of brain lysates showing N-20 detected one 180 kDa band whereas AF1079 recognized the 180 kDa band and a N-terminal deletion of Neogenin at about 150 kDa. Immunofluorescence images of retinal growth cone of (C) F-actin (Alexa Phalloidin) and (D) Neogenin. Bar, 30 µm. (E) Composite images of Neogenin staining, the raft marker cholera toxin subunit B (CTB) and merged image where the indicated region as shown in dashed outline (and amplified) indicated an alteration in color (color not shown), which indicated colocalization of Neogenin and CTB. Intensity correlation quotient (ICQ) to quantify colocalization between Neogenin and CTB was calculated in 12 growth cones. ICQ reflected the ratio of the number of positive or negative $(A_i-a)(B_i-b)$ values to the total pixel number minus 0.5 to derive a −0.5 to +0.5 range. Here, an average ICQ of 0.27 was computed, which indicated strong colocalization between Neogenin and CTB. Bar, 30 μm. (F) Composite images of Neogenin (AF1079), the RGMa and merged image where the indicated region as shown in color (color not shown), which indicated colocalization of Neogenin and RGMa. An average ICQ of 0.32 was computed, which indicated strong co-localization between Neogenin and RGMa. Bar, 30 μm. (G) Chick brain gradient fractionation showing that Neogenin (arrowhead) localized with RGMa and raft marker, Flotillin. Transferrin receptor (TfR) was used as a heavy fraction marker.

The present invention is directed to a method of modulating a cis interaction between Repulsive Guidance Molecule A (RGMa) and Neogenin in a subject in need thereof, and a method of modulating the recruitment of (i. e., disrupting the recruitment to and/or maintenance of) Neogenin within lipid rafts. The trans interaction occurs between extracellular RGMa and Neogenin at the surface of the neuronal cells while the cis interaction unexpectedly occurs between RGMa and Neogenin located within the same plasma membrane of a neuronal cell.

Both blocking of the cis interaction and disrupting the lipid rafts, the discovery of which is described herein, has the ability to counteract the two negative effects in response to injury or disease of the CNS (a) cell death and (b) axon inhibition. Upon recruitment to the lipid rafts, Neogenin, in the absence of a trans interaction with RGMa, signals to induce neuronal cell death (e.g., apoptosis). Inhibiting the recruitment of Neogenin to the lipid rafts, by either disruption of the lipid rafts themselves, or by preventing the cis interaction between RGMa and Neogenin, results in both an increase in neuronal cell survival and an increase in axon growth and/or regeneration.

This cis interaction is mediated by the four immunoglobulin-like domains (4Ig domains) of Neogenin and an N-terminal portion of RGMa (i.e., described herein as N-Raft or amino acids 28 to 73 of RGMa). Mapping experiments within N-Raft, which are described below in more detail and shown in FIGS. 2A, 9, and 17, indicated that amino acids 40 to 73 of RGMa contain amino acids and/or secondary structure necessary for binding the 4Ig domain of Neogenin. Additionally, full-length RGMa was unable to bind the 4Ig domain, indicating that these required amino acids and/or secondary structure may needed to be exposed (e.g., upon a conformational change) in RGMa for the cis interaction to occur with Neogenin.

As described below in more detail, the method of modulating includes blocking or disrupting the cis interaction between RGMa and Neogenin and/or disrupting the lipid rafts. Such methods alter Neogenin's recruitment to the lipid rafts thereby preventing Neogenin from signaling to induce cell death and inhibit axon growth and/or regeneration.

The method of modulating also includes administering an agent that blocks or disrupts the cis interaction between RGMa and Neogenin, and/or disrupts the lipid rafts. This agent may be a peptide agent, a cholesterol-lowering agent, or an antibody as described below in more detail.

The present invention is also directed to a method of identifying an agent that modulates the cis interaction between RGMa and Neogenin. The agent may be an antibody or an antibody fragment. The antibody or antibody fragment may specifically recognize and selectively bind the amino acids and/or secondary structure required for the cis interaction to occur between RGMa and Neogenin. As such, the antibody or antibody fragment may inhibit the cis interaction, modulate Neogenin recruitment to lipid rafts, and promote neuronal cell survival and axon growth and/or regeneration.

The present invention is also directed to a method of treating a disease in a subject in need thereof. The method of treating may apply the method of modulating to promote neuronal cell survival and axon growth and/or regeneration in the subject. The disease may be retinitis pigmentosa, ischemia, multiple sclerosis, spinal cord injury, or optic nerve injury.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Acceptor" and "acceptor antibody" are used herein to refer to the antibody or nucleic acid sequence providing or encoding at least 80%, at least 85%, at least 90%, at least 91%, at least 92%, at least 93%, at least 94%, at least 95%, at least 96%, at least 97%, at least 98%, at least 99% or 100% of the amino acid sequences of one or more framework regions. The term "acceptor" encompasses an antibody amino acid or nucleic acid sequence providing or encoding the constant region(s). The term also encompasses the antibody amino acid or nucleic acid sequence providing or encoding one or more of the framework regions and the constant region(s). For example, the term "acceptor" may refer to a human antibody amino acid or nucleic acid sequence that provides or encodes at least 80%, at least 85%, at least 90%, at least 91%, at least 92%, at least 93%, at least 94%, at least 95%, at least 96%, at least 97%, at least 98%, at least 99% or 100% of the amino acid sequences of one or more of the framework regions. Such an acceptor may contain at least 1, at least 2, at least 3, at least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, or a functional antibody (e.g., antibodies well-known in the art, antibodies in development, or antibodies commercially available).

"Affinity Matured Antibody" is used herein to refer to an antibody with one or more alterations in one or more CDRs, which result in an improvement in the affinity (i.e. KD, kd or ka) of the antibody for a target antigen compared to a parent antibody, which does not possess the alteration(s). Exemplary affinity matured antibodies will have nanomolar or even picomolar affinities for the target antigen. A variety of procedures for producing affinity matured antibodies is known in the art, including the screening of a combinatory antibody library that has been prepared using bio-display. For example, Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); and Hawkins et al, J. Mol. Biol., 226: 889-896 (1992). Selective mutation at selective mutagenesis positions and at contact or hypermutation positions with an activity-enhancing amino acid residue is described in U.S. Pat. No. 6,914,128 B1.

"Antibody" and "antibodies" as used herein refers to monoclonal antibodies, multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')$_2$ fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., Nature Biotechnology, 25(11):1290-1297 (2007) and PCT International Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. For simplicity sake, an antibody against an analyte is frequently referred to herein as being either an "anti-analyte antibody" or merely an "analyte antibody."

"Antibody fragment" as used herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')$_2$ fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Bispecific antibody" is used herein to refer to a full-length antibody that is generated by quadroma technology (see Milstein et al., Nature, 305(5934): 537-540 (1983)), by chemical conjugation of two different monoclonal antibodies (see, Staerz et al., Nature, 314(6012): 628-631 (1985)), or by knob-into-hole or similar approaches, which introduce mutations in the Fc region (see Holliger et al., Proc. Natl. Acad. Sci. USA, 90(14): 6444-6448 (1993)), resulting in multiple different immunoglobulin species of which only one is the functional bispecific antibody. A bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences), and is monovalent for each antigen to which it binds to.

"CDR" is used herein to refer to the "complementarity determining region" within an antibody variable sequence. There are three CDRs in each of the variable regions of the heavy chain and the light chain, which are designated "CDR1", "CDR2", and "CDR3", for each of the variable regions. The term "CDR set" as used herein refers to a group of three CDRs that occur in a single variable region that binds the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, J. Mol. Biol., 196: 901-917 (1987); and Chothia et al., Nature, 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, FASEB J., 9: 133-139 (1995), and MacCallum, J. Mol. Biol., 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat- or Chothia-defined CDRs.

"CDR-grafted antibody" is used herein to refer to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

"Chimeric antibody" is used herein to refer to antibodies which comprise heavy and light chain variable region sequences from one species and constant region sequences from another species, such as antibodies having murine heavy and light chain variable regions linked to human, canine, equine, or feline constant regions. Chimeric antibodies comprise a portion of the heavy and/or light chain that is identical to or homologous with corresponding sequences from antibodies derived from a particular species or belonging to a particular antibody class or subclass, while the remainder of the chain(s) is identical to or homologous with corresponding sequences in antibodies from another species or belonging to another antibody class or subclass, as well as fragments of such antibodies, exhibiting the desired biological activity (see e.g., U.S. Pat. No. 4,816,567 and Morrison et al., Proc. Natl. Acad. Sci. USA 81:6851-6855 (1984)).

"Diabodies" is used herein to refer to small antibody fragments with two antigen-binding sites, which fragments comprise a heavy chain variable domain (VH) connected to a light chain variable domain (VL) in the same polypeptide chain (VH-VL). By using a linker that is short to allow pairing between the two domains on the same chain, the domains are forced to pair with the complementary domains of another chain and create two antigen-binding sites.

"Donor" and "donor antibody" are used herein to refer to an antibody providing one or more CDRs. A donor antibody may be an antibody from a species different from the antibody from which the framework regions are obtained or derived. In the context of a humanized antibody, the term "donor antibody" refers to a non-human antibody providing one or more CDRs. In the context of a bovinized antibody, the term "donor antibody" refers to a non-bovine antibody providing one or more CDRs. In the context of a porcinized antibody, the term "donor antibody" refers to a non-porcine antibody providing one or more CDRs. In the context of a caninized antibody, the term "donor antibody" refers to a non-canine antibody providing one or more CDRs. In the context of a felinized antibody, the term "donor antibody" refers to a non-feline antibody providing one or more CDRs. In the context of an equinized antibody, the term "donor antibody" refers to a non-equine antibody providing one or more CDRs.

"Dual-specific antibody" is used herein to refer to a full-length antibody that can bind two different antigens (or epitopes) in each of its two binding arms (a pair of HC/LC) (see PCT publication WO 02/02773). Accordingly, a dual-specific binding protein has two identical antigen binding arms, with identical specificity and identical CDR sequences, and is bivalent for each antigen to which it binds.

"Dual variable domain" is used herein to refer to two or more antigen binding sites on a binding protein, which may be divalent (two antigen binding sites), tetravalent (four antigen binding sites), or multivalent binding proteins. DVDs may be monospecific, i.e., capable of binding one antigen (or one specific epitope), or multispecific, i.e., capable of binding two or more antigens (i.e., two or more epitopes of the same target antigen molecule or two or more epitopes of different target antigens). A preferred DVD binding protein comprises two heavy chain DVD polypeptides and two light chain DVD polypeptides and is referred to as a "DVD immunoglobulin" or "DVD-Ig". Such a DVD-Ig binding protein is thus tetrameric and reminiscent of an IgG molecule, but provides more antigen binding sites than an IgG molecule. Thus, each half of a tetrameric DVD-Ig molecule is reminiscent of one half of an IgG molecule and comprises a heavy chain DVD polypeptide and a light chain DVD polypeptide, but unlike a pair of heavy and light chains of an IgG molecule that provides a single antigen binding domain, a pair of heavy and light chains of a DVD-Ig provide two or more antigen binding sites.

Each antigen binding site of a DVD-Ig binding protein may be derived from a donor ("parental") monoclonal antibody and thus comprises a heavy chain variable domain (VH) and a light chain variable domain (VL) with a total of six CDRs involved in antigen binding per antigen binding site. Accordingly, a DVD-Ig binding protein that binds two different epitopes (i.e., two different epitopes of two different antigen molecules or two different epitopes of the same antigen molecule) comprises an antigen binding site derived from a first parental monoclonal antibody and an antigen binding site of a second parental monoclonal antibody.

A description of the design, expression, and characterization of DVD-Ig binding molecules is provided in PCT Publication No. WO 2007/024715, U.S. Pat. No. 7,612,181, and Wu et al., Nature Biotech., 25: 1290-1297 (2007). A preferred example of such DVD-Ig molecules comprises a heavy chain that comprises the structural formula VD1-(X1)n-VD2-C-(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, but preferably 1; and a light chain that comprises the structural formula VD1-(X1)n-VD2-C-(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, but preferably 1. Such a DVD-Ig may comprise two such heavy chains and two such light chains, wherein each chain comprises variable domains linked in tandem without an intervening constant region between variable regions, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

In a preferred embodiment, a DVD-Ig binding protein according to the invention not only binds the same target molecules bound by its parental monoclonal antibodies, but also possesses one or more desirable properties of one or more of its parental monoclonal antibodies. Preferably, such an additional property is an antibody parameter of one or more of the parental monoclonal antibodies. Antibody parameters that may be contributed to a DVD-Ig binding protein from one or more of its parental monoclonal antibodies include, but are not limited to, antigen specificity, antigen affinity, potency, biological function, epitope recognition, protein stability, protein solubility, production efficiency, immunogenicity, pharmacokinetics, bioavailability, tissue cross reactivity, and orthologous antigen binding.

A DVD-Ig binding protein binds at least one epitope of the RGMa peptide or Neogenin peptide. Non-limiting examples of a DVD-Ig binding protein include a DVD-Ig binding protein that binds one or more epitopes of the RGMa peptide or Neogenin peptide, a DVD-Ig binding protein that binds an epitope of a human RGMa peptide or Neogenin peptide and an epitope of a RGMa peptide or Neogenin peptide of another species (for example, mouse), and a DVD-Ig binding protein that binds an epitope of the RGMa peptide or Neogenin peptide and an epitope of another target molecule.

"Epitope," or "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

"Fab" is used herein to refer to antibody fragments. Papain digestion of antibodies produces two identical antigen-binding fragments called "Fab" fragments, each with a single antigen-binding site, and a residual "Fc" fragment, whose name reflects its ability to readily crystallize. Pepsin treatment yields a binding cross-linking antigen. The Fab fragment also contains the constant domain of the light chain and the first domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine(s) of the constant domains bear a free thiol group. $F(ab')_2$ antibody fragments originally were produced as pairs of Fab' fragments which have hinge cysteines between them. Other chemical couplings of antibody fragments are also known.

"$F(ab')_2$ fragment" as used herein refers to antibodies generated by pepsin digestion of whole IgG antibodies to remove most of the Fc region while leaving intact some of the hinge region. $F(ab')_2$ fragments have two antigen-binding F(ab) portions linked together by disulfide bonds, and therefore are divalent with a molecular weight of about 110 kDa. Divalent antibody fragments ($F(ab')_2$ fragments) are smaller than whole IgG molecules and enable a better penetration into tissue thus facilitating better antigen recognition in immunohistochemistry. The use of $F(ab')_2$ fragments also avoids unspecific binding to Fc receptor on live cells or to Protein A/G. $F(ab')_2$ fragments can both bind and precipitate antigens.

"Framework" (FR) or "Framework sequence" as used herein may mean the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

Human heavy chain and light chain FR sequences are known in the art that can be used as heavy chain and light chain "acceptor" framework sequences (or simply, "acceptor" sequences) to humanize a non-human antibody using techniques known in the art. In one embodiment, human heavy chain and light chain acceptor sequences are selected from the framework sequences listed in publicly available databases such as V-base (hypertext transfer protocol://vbase.mrc-cpe.cam.ac.uk/) or in the international ImMunoGeneTics® (IMGT®) information system (hypertext transfer protocol://imgt.cines.fr/texts/IMGTrepertoire/Locus Genes/).

"Fv" is used herein to refer to the minimum antibody fragment that contains a complete antigen-recognition and binding site. This region consists of a dimer of one heavy chain and one light chain variable domain.

"Human antibody" is used herein to refer to antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example, in the CDRs. However, the term "human antibody" is not intended to include antibodies in which CDR sequences derived from the germline of another mammalian species, such as a mouse, have been grafted onto human framework sequences.

"Humanized antibody" is used herein to describe an antibody that comprises heavy and light chain variable region sequences from a non-human species (e.g. a mouse) but in which at least a portion of the VH and/or VL sequence has been altered to be more "human-like," i.e., more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98%, or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well-known in the art.

The framework regions and CDRs of a humanized antibody need not correspond precisely to the parental sequences, e.g., the donor antibody CDR or the consensus framework may be mutagenized by substitution, insertion, and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, From Genes to Clones (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence.

"Hypervariable region" is used herein to refer to the amino acid residues of an antibody which are responsible for antigen-binding. The hypervariable region comprises amino acid residues from a "complementarity determining region" or "CDR" in the light chain variable domain and in the heavy chain variable domain as defined by Kabat et al., 5th Ed. Public Health Service, National Institutes of Health, Bethesda, Md. (1991) and/or defined by Chothia and Lesk, Mol. Biol. 196:901-917 (1987) and/or as defined as "AbM loops" by Martin et al., Proc. Natl. Acad. Sci. USA, 86:9268-9272 (1989) and/or as defined by Lefranc et al., Nucleic Acids Res., 27:209-212 (1999) in the international ImMunoGeneTics information systems database. "Framework" or "FR" residues are those variable domain residues other than the hypervariable region residues as herein defined.

"Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Kabat numbering," "Kabat definitions," and "Kabat labeling" as used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al., Ann. NY Acad. Sci., 190:382-391 (1971) and Kabat et al., Sequences of Proteins of Immunological Interest, Fifth Edition, U.S. Department of Health and Human Services, NIH Publication No. 91-3242 (1991)). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

"Lipid raft" as used herein refers to a microdomain of membrane of a cell that contains an enriched amount of cholesterol (e.g. as compared to other regions of the membrane). In some embodiments, the enrichment is greater than 2-fold. In other embodiments, the enrichment is greater than 3-fold. In still other embodiments, the enrichment is greater than 4 fold. In yet other embodiments, the enrichment is greater than 5-fold more cholesterol as compared to the other regions of the membrane.

"Monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological.

"Pharmaceutically acceptable carrier" as used herein includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol, and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

"Polynucleotide" as used herein refers to a polymeric form of two or more nucleotides, either ribonucleotides or deoxyribonucleotides or a modified form of either type of nucleotide. The term includes single and double stranded forms of DNA. The term "isolated polynucleotide" shall mean a polynucleotide (e.g., of genomic, cDNA, or synthetic origin, or some combination thereof) that, by virtue of its origin, the "isolated polynucleotide" is not associated with all or a portion of a polynucleotide with which the "isolated polynucleotide" is found in nature; is operably linked to a polynucleotide that it is not linked to in nature; or does not occur in nature as part of a larger sequence.

"Polypeptide" as used herein refers to any polymeric chain of amino acids. The terms "peptide" and "protein" are used interchangeably with the term polypeptide and also refer to a polymeric chain of amino acids. The term "polypeptide" encompasses native or artificial proteins, protein fragments, and polypeptide analogs of a protein sequence. A polypeptide may be monomeric or polymeric.

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., Nature Biotechnology, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

"Single-chain Fv or "scFv" as used herein refers to antibody fragments comprising the VH and VL domains of an antibody, wherein these domains are present in a single polypeptide chain. Generally, the Fv polypeptide further comprises a polypeptide linker between the VH and VL domains which enables the scFv to form the desired structure for antigen binding. For a review of scFv, see Pluckthun in the The Pharmacology of Monoclonal Antibodies, vol. 113, Rosenburg and Moore eds. Springer-Verlag, New York, pp. 269-315 (1994).

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Therapeutically effective amount" as used herein refers to an amount effective, at dosages and for periods of time necessary, to achieve the desired therapeutic result. A therapeutically effective amount may be the amount and/or duration of a therapy which is sufficient to reduce or ameliorate the severity and/or duration of a disorder or one or more symptoms thereof, prevent the advancement of a disorder, cause regression of a disorder, prevent the recurrence, development, onset, or progression of one or more symptoms associated with a disorder, detect a disorder, or enhance or improve the prophylactic or therapeutic effect(s) of another therapy (e.g., prophylactic or therapeutic agent). A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects.

"Treat", "treating" or "treatment" are each used interchangeably herein to describe reversing, alleviating, or inhibiting the onset or progress of a disease, or reversing, alleviating, or inhibiting one or more symptoms of such disease, to which such term applies. Depending on the condition of the subject, the term also refers to preventing a disease, and includes preventing the onset of a disease, or preventing one or more symptoms associated with a disease. A treatment may be either performed in an acute or chronic way. The term also refers to reducing the severity of a disease or symptoms associated with such disease prior to affliction with the disease or the symptoms thereof. Such prevention or reduction of the severity of a disease or symptoms thereof prior to affliction refers to administration of an agent or pharmaceutical composition of the present invention to a subject that is not at the time of administration afflicted with the disease or symptoms thereof. "Preventing" also refers to preventing the recurrence of a disease or of one or more symptoms associated with such disease. "Treatment" and "therapeutically," refer to the act of treating, as "treating" is defined above.

"Variant" is used herein to describe a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to describe a polypeptide or a fragment thereof that has been differentially processed, such as by proteolysis, phosphorylation, or other post-translational modification, yet retains its antigen reactivity.

"Vernier zone" as used herein refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact the structure of CDRs and the affinity of the antibody.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Method of Modulating Neuronal Cell Survival and Axon Growth and/or Regeneration Provided herein is a method of modulating both neuronal cell survival and axon growth and/or regeneration. Modulating may include altering (e.g., blocking or disrupting) the cis interaction between Repulsive Guidance Molecule A (RGMa) and Neogenin, and/or disrupting the integrity of lipid rafts.

In one embodiment, what is modulated is a cis interaction between RGMa and Neogenin in a subject in need thereof. The cis interaction between RGMa and Neogenin is described below in more detail. The method of modulating may disrupt this cis interaction. The method of modulating may block this cis interaction.

Disrupting or blocking the cis interaction may promote neuronal cell survival and axon growth and/or regeneration. Disrupting or blocking the cis interaction may promote neuronal cell survival and axon growth and/or regeneration through modulating recruitment of the Neogenin receptor. The neuronal cell may be, but is not limited to, retinal ganglion cells (RGCs), motor neurons, hippocampal cells, cortical cells, photoreceptor cells, and spinal neurons.

The method of modulating may include administering an agent to the subject. This agent may disrupt the cis interaction. This agent may block the cis interaction. Accordingly, by disrupting or blocking the cis interaction, the agent may promote neuronal cell survival and axon growth and/or regeneration.

In another embodiment, what is modulated is the integrity of lipid rafts. The method of modulating may disrupt lipid rafts. The method of modulating may reduce the level of cholesterol within lipid rafts which may disrupt lipid rafts. Disrupting lipid rafts or reducing the level of cholesterol within lipid rafts may impact recruitment which in turn may promote neuronal cell survival and axon growth and/or regeneration.

The method of modulating the integrity of lipid rafts may include administering an agent to the subject. This agent may disrupt lipid rafts and/or diminish the level of cholesterol within lipid rafts. Accordingly, disrupting lipid rafts and/or reducing the level of cholesterol within lipid rafts may impact the ability of the cis interaction between RGMa and Neogenin. In addition disrupting lipid rafts and/or reducing the level of cholesterol within lipid rafts may also impact the ability of the trans interaction between RGMa and Neogenin and/or impact the ability of the trans interaction between RGMa and Neogenin to inhibit axon growth. Disrupting lipid rafts and/or reducing the level of cholesterol within lipid rafts by such agents may promote neuronal cell survival and axon growth and/or regeneration.

These methods of modulating may be used in a method of treating a subject in need thereof as described below in more detail.

a. Cis Interaction Between RGMa and Neogenin and Lipid Raft Disruption

The method may modulate the cis interaction between RGMa and Neogenin, and/or lipid rafts.

RGMa is a 33 kDa glycosylphosphatidylinositol (GPI)-linked membrane glycoprotein. The full-length RGMa protein contains an N-terminal signal peptide, an RGD motif, a partial von Willebrand factor (vWF) type D domain, a hydrophobic region, and a C-terminal GPI-anchor. RGMa is cleaved to generate various RGMa peptides, some of which are membrane associated, some of which are soluble, and some of which are linked by a disulfide bond. For example, cleavage may include autoproteolysis, in which the resulting N-terminal (N-RGMa) and C-terminal (C-RGMa) domains may be linked by a disulfide bridge. Cleavage may also include the enzyme Furin-1, which releases a soluble N-terminal peptide from RGMa, and shedding cleavage sites.

RGMa was initially identified as a chemorepulsive molecule for retinal axons that bound Neogenin. Neogenin is a member of the immunoglobulin superfamily of transmembrane receptors and includes four N-terminal immunoglobulin-like domains, six fibronection domains, a transmembrane domain, and a C-terminal domain.

Together, RGMa and Neogenin mediate axon guidance in the developing visual system and axon tract guidance in the developing brain. In particular, a trans interaction between RGMa and Neogenin inhibits axon growth and/or regeneration in the developing central nervous system (CNS) and the injured CNS. In this trans interaction, RGMa peptides are secreted by cells surrounding the neurons and the secreted RGMa peptides interact with Neogenin located at the surface neurons. This trans interaction between RGMa and Neogenin also promotes cell survival. In the absence of this trans interaction, Neogenin induces cell death, namely apoptosis. Accordingly, Neogenin is a dependence-receptor that signals to promote cell survival in the presence of the trans interaction, but signals to induce cell death in the absence of the trans interaction.

As demonstrated herein, Neogenin signaling to induce cell death is mediated by a cis interaction that occurs between RGMa and Neogenin. This cis interaction occurs between RGMa and Neogenin associated with the same plasma membrane of a neuronal cell. In particular, this cis interaction facilitates recruitment of Neogenin to lipid rafts in the membranes of the neuronal cells. Lipid rafts are microdomains within membranes that are enriched in cholesterol. Disrupting lipid rafts and/or blocking or disrupting the cis interaction modulates Neogenin recruitment to lipid rafts, thereby preventing or reducing cell death attributable to Neogenin signaling.

As also demonstrated herein, this cis interaction between RGMa and Neogenin is required in addition to the trans interaction between RGMa and Neogenin to inhibit axon growth and/or regeneration. Accordingly, blocking or disrupting the cis interaction, even if the trans interaction occurs, prevents Neogenin recruitment to lipid rafts and/or removes Neogenin from lipid rafts, thereby preventing or reducing inhibition of axonal growth and/or regeneration attributable to Neogenin signaling.

As further demonstrated herein, disruption of lipid rafts by depleting cholesterol with a cholesterol-lowering agent, which is described below in more detail, prevents or reduces (1) cell death and (2) inhibition of axon growth and/or regeneration that is attributable to Neogenin signaling. It is hypothesized that this prevention or reduction occurs because Neogenin needs to be present in lipid rafts to signal.

As such, it is demonstrated herein that Neogenin signaling may be inhibited or blocked by (1) disruption of lipid rafts with the cholesterol-lowering agent and/or (2) blocking or disrupting the cis interaction between RGMa and Neogenin.

As also demonstrated herein, the trans and cis interactions are mediated by different portions of RGMa and Neogenin. The trans interaction between RGMa and Neogenin is mediated through the six fibronection domains of Neogenin (also known herein as "the 6FNIII domain of Neogenin" or "6FNIII domain"). The cis interaction between RGMa and Neogenin is mediated by amino acids 28 to 73 of RGMa (also known herein as "N-Raft") and the four immunoglobulin-like domains of Neogenin (also known herein as "the 4Ig domain of Neogenin" or "4Ig"). The cis interaction between RGMa and Neogenin is also facilitated by Bone Morphogenetic Protein (BMP), and thus, BMP is also required for Neogenin recruitment to lipid rafts.

As also demonstrated herein, portions of N-Raft are sufficient for the cis interaction. These portions are amino acids 54 to 73 and 40 to 62 of RGMa, but not amino acids 28 to 54 or 54 to 62 of RGMa. This mapping indicated that amino acids 40 to 73 of RGMa may be sufficient for the cis interaction. In contrast, full-length RGMa is unable to interact with the 6FNIII domain of Neogenin. Together, this indicated that the cis interaction may be dependent upon the structure or folding of RGMa. Full-length RGMa may require additional factors such as BMP to expose the 4Ig binding site (i.e., encompassed by amino acids 28 to 73, 54 to 73, 40 to 62, and 40 to 73 of RGMa) on RGMa for the cis interaction to occur between RGMa and Neogenin.

b. Agent

As described above, the method may modulate the cis interaction between RGMa and Neogenin, and/or disrupt lipid rafts, by administering the agent to the subject. The agent may disrupt or blocks the cis interaction and thus, promotes neuronal cell survival and axon growth and/or regeneration. The agent may also disrupt lipid rafts, including reducing the level of cholesterol from within the lipid rafts which in turn promotes neuronal cell survival and axon growth and/or regeneration. The agent may be an antibody, a peptide agent, a cholesterol-lowering agent, or any combination thereof. The antibody, peptide agent, and cholesterol-lowering agent are described below in more detail.

(1) Peptide Agent

The method may modulate the cis interaction between RGMa and Neogenin by administering the peptide agent to the subject. The peptide agent may disrupt or block the cis interaction and thus, promote neuronal cell survival and axon growth and/or regeneration. The peptide agent may be an RGMa peptide, a Neogenin peptide, a Noggin peptide, fragment thereof, variant thereof, or any combination thereof. The RGMa peptide, Neogenin peptide, and Noggin peptide are described below in more detail.

(a) Neogenin Peptide

The method may modulate the cis interaction between RGMa and Neogenin by administering the Neogenin peptide to the subject. The Neogenin peptide may disrupt or block the cis interaction and thus, promote neuronal cell survival and axon growth and/or regeneration.

The Neogenin peptide may include fragments of Neogenin, variants of Neogenin, or any combination thereof. The Neogenin peptide may include two immunoglobulin-like domains of Neogenin, fragments thereof, variants thereof, or any combination thereof. The Neogenin peptide may include three immunoglobulin-like domains of Neogenin, fragments thereof, variants thereof, or any combination thereof. The Neogenin peptide may include four immunoglobulin-like domains of Neogenin, fragments thereof, variants thereof, or any combination thereof. Four immunoglobulin-like domains of Neogenin may also be referred to herein as the 4Ig domain of Neogenin. Accordingly, the Neogenin peptide may include the 4Ig domain, fragment thereof, variant thereof, or any combination thereof.

The Neogenin peptide may include an amino acid sequence comprising amino acids 1 to 383 of Accession No. AAC59662 (SEQ ID NO:1). The Neogenin peptide may include an amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% to the amino acid sequence comprising amino acids 1 to 383 of Accession No. AAC59662 (SEQ ID NO:1). The Neogenin peptide may be amino acids 1 to 383 of Accession No. AAC59662 (SEQ ID NO:1), a fragment thereof, a variant thereof, or any combination thereof.

The Neogenin peptide may include an amino acid sequence comprising amino acids 1 to 417 of Accession No. AAI43272 (SEQ ID NO:11). The Neogenin peptide may include an amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% to the amino acid sequence comprising amino acids 1 to 417 of Accession No. AAI43272 (SEQ ID NO:11). The Neogenin peptide may be amino acids 1 to 417 of Accession No. AAI43272 (SEQ ID NO:11), a fragment thereof, a variant thereof, or any combination thereof.

The Neogenin peptide may include the amino acid sequence set forth in SEQ ID NO:8, a fragment thereof, a variant thereof, or any combination thereof. The Neogenin peptide may include an amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to the amino acid sequence set forth in SEQ ID NO:8. The Neogenin peptide may be the amino acid sequence set forth in SEQ ID NO:8.

(b) RGMa Peptide

The method may modulate the cis interaction between RGMa and Neogenin by administering the RGMa peptide to the subject. The RGMa peptide may disrupt or block the cis interaction and thus, promote neuronal cell survival and axon growth and/or regeneration.

The RGMa peptide may include fragments of RGMa, variants of RGMa, or any combination thereof. The RGMa peptide may be any fragment of RGMa that interacts with the 4Ig domain of Neogenin. The RGMa peptide may contain any secondary structure that may be required for the cis interaction to occur between RGMa and Neogenin.

Figure 16:
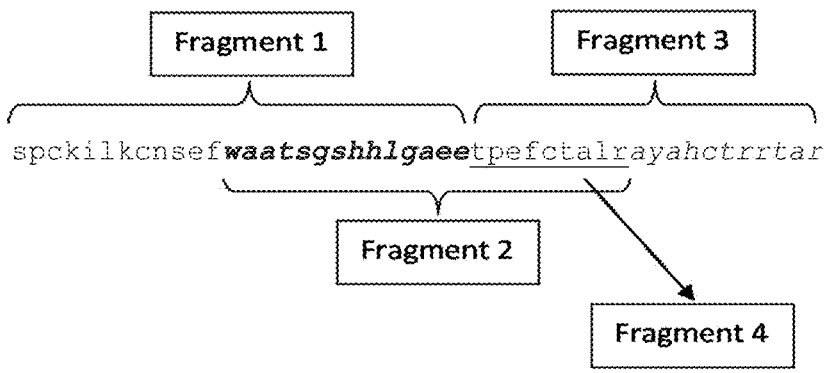
FIG. 16 shows the sequence of amino acids 28-73 of chicken RGMa. The chicken RGMa sequence was Accession No. NP_989868.1 (SEQ ID NO:6).

The RGMa peptide may include the amino acid sequence set forth in SEQ ID NO:2, a fragment thereof, a variant thereof, or any combination thereof. The RGMa peptide may include an amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to the amino acid sequence set forth in SEQ ID NO:2. The RGMa peptide may be the amino acid sequence set forth in SEQ ID NO:2. The amino acid sequence set forth in SEQ ID NO:2 may also be referred to herein as "N-Raft." The amino acid sequence set forth in SEQ ID NO:2 is shown in FIG. 16 and is amino acids 28 to 73 of RGMa.

The RGMa peptide may include the amino acid sequence set forth in SEQ ID NO:3, a fragment thereof, a variant thereof, or any combination thereof. The RGMa peptide may include an amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to the amino acid sequence set forth in SEQ ID NO:3. The RGMa peptide may be the amino acid sequence set forth in SEQ ID NO:3. The amino acid sequence set forth in SEQ ID NO:3 may be amino acids 54 to 73 of RGMa.

The RGMa peptide may include the amino acid sequence set forth in SEQ ID NO:4, a fragment thereof, a variant thereof, or any combination thereof. The RGMa peptide may include an amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to the amino acid sequence set forth in SEQ ID NO:4. The RGMa peptide may be the amino acid sequence set forth in SEQ ID NO:4. The amino acid sequence set forth in SEQ ID NO:4 may be amino acids 40 to 62 of RGMa.

The RGMa peptide may include the amino acid sequence set forth in SEQ ID NO:7, a fragment thereof, a variant thereof, or any combination thereof. The RGMa peptide may include an amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to the amino acid sequence set forth in SEQ ID NO:7. The RGMa peptide may be the amino acid sequence set forth in SEQ ID NO:4. The amino acid sequence set forth in SEQ ID NO:7 may be amino acids 40 to 73 of RGMa.

The RGMa peptide may include the amino acid sequence set forth in SEQ ID NO:10, a fragment thereof, a variant thereof, or any combination thereof. The RGMa peptide may include an amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to the amino acid sequence set forth in SEQ ID NO:10. The RGMa peptide may be the amino acid sequence set forth in SEQ ID NO:10.

Peptides that act similar to the RGMa peptide, i.e., blocking or disrupting the cis interaction between RGMa and Neogenin, may include a peptide from RGMc. This RGMc peptide may include the amino acid sequence set forth in SEQ ID NO:9, a fragment thereof, a variant thereof, or any combination thereof. The RGMc peptide may include an amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to the amino acid sequence set forth in SEQ ID NO:9. The RGMc peptide may be the amino acid sequence set forth in SEQ ID NO:9.

(c) Noggin

The method may modulate the cis interaction between RGMa and Neogenin by administering the Noggin peptide to the subject. The Noggin peptide may disrupt or block the cis interaction and thus, promote neuronal cell survival and axon growth and/or regeneration.

The Noggin peptide may include fragments of Noggin, variants of Noggin, or any combination thereof. The Noggin peptide may include the amino acid sequence of Accession No. AAA83259 (SEQ ID NO:5). The Noggin peptide may include an amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99° A identity to the amino acid sequence of Accession No. AAA83259 (SEQ ID NO:5). The Noggin peptide may be the amino acid sequence of Accession No. AAA83259 (SEQ ID NO:5).

(2) Cholesterol-Lowering Agent

The method may modulate the cis interaction between RGMa and Neogenin by administering the cholesterol-lower agent to the subject. The cholesterol-lowering agent may disrupt lipid rafts and/or prevent or block the cis interaction and thus, promote neuronal cell survival and axon growth and/or regeneration.

The cholesterol-lowering agent may be, but is not limited to, methyl-β-cyclodextrin (MβCD), cholesterol oxidase (CO), AY-9944, a statin, a subtisilin/kexin type 9 (PCK9) inhibitor, nystatin, filipin, proprotein convertase, BM15.766, alkylphospholipid analogs (e.g., miltefosine, edelfosine, and perifosine), or any combination thereof.

(3) Antibody

The method may modulate the cis interaction between RGMa and Neogenin by administering the antibody to the subject. The antibody may disrupt or block the cis interaction and thus, promote neuronal cell survival and axon growth and/or regeneration.

The antibody may be directed against the RGMa peptide described above. This RGMa peptide contains any secondary structure that may be required for the cis interaction to occur between RGMa and Neogenin. Accordingly, the antibody directed against the RGMa peptide may specifically recognize and selectively bind this secondary structure.

In some embodiments, the antibody may specifically recognize and selectively bind the amino acid sequence as set forth in SEQ ID NO:2, the amino acid sequence as set forth in SEQ ID NO:3, the amino acid sequence as set forth in SEQ ID NO:4, the amino acid sequence as set forth in SEQ ID NO:7, the amino acid sequence as set forth in SEQ ID NO:9, and/or the amino acid sequence as set forth in SEQ ID NO:10. The antibody may specifically recognize and selectively bind to amino acids 28 to 73, 40 to 62, 54 to 73, and/or 40 to 73 of RGMa.

In other embodiments, the antibody may be directed against the Neogenin peptide described above, for example, the 4Ig domain of Neogenin or an extracellular portion of Neogenin. The antibody may specifically recognize and selectively bind the 4Ig domain of Neogenin. The antibody may specifically recognize and selectively bind amino acids 1 to 383 of Accession No. AAC59662 (SEQ ID NO:1), amino acids 1 to 417 of Accession No. AAI43272 (SEQ ID NO:11), and/or the amino acid sequence as set forth in SEQ ID NO:8.

(a) Antibody Preparation/Production

Antibodies may be prepared by any of a variety of techniques. In general, antibodies can be produced by cell culture techniques, including the generation of monoclonal antibodies via conventional techniques, or via transfection of antibody genes, heavy chains, and/or light chains into suitable bacterial or mammalian cell hosts, in order to allow for the production of antibodies, wherein the antibodies may be recombinant. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the invention include Chinese Hamster Ovary (CHO cells) (including dhfr-CHO cells, described in Urlaub and Chasin, Proc. Natl. Acad. Sci. USA, 77: 4216-4220 (1980)), used with a DHFR selectable marker, e.g., as described in Kaufman and Sharp, J. Mol. Biol., 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention (i.e., binds RGMa peptide or Neogenin peptide) and the other heavy and light chain are specific for an antigen other than the RGMa peptide or the Neogenin peptide by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

Methods of preparing monoclonal antibodies involve the preparation of immortal cell lines capable of producing antibodies having the desired specificity. Such cell lines may be produced from spleen cells obtained from an immunized animal. The animal may be immunized with the RGMa peptide or the Neogenin peptide or a fragment and/or variant thereof. The peptide used to immunize the animal may comprise amino acids encoding human Fc, for example the fragment crystallizable region or tail region of human antibody. The spleen cells may then be immortalized by, for example, fusion with a myeloma cell fusion partner. A variety of fusion techniques may be employed. For example, the spleen cells and myeloma cells may be combined with a nonionic detergent for a few minutes and then plated at low density on a selective medium that supports that growth of hybrid cells, but not myeloma cells. One such technique uses hypoxanthine, aminopterin, thymidine (HAT) selection. Another technique includes eletrofusion. After a sufficient time, usually about 1 to 2 weeks, colonies of hybrids are observed. Single colonies are selected and their culture supernatants tested for binding activity against the polypeptide. Hybridomas having high reactivity and specificity may be used.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Affinity chromatography is an example of a method that can be used in a process to purify the antibodies.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites.

The Fv fragment can be produced by preferential proteolytic cleavage of an IgM, and on rare occasions IgG or IgA immunoglobulin molecules. The Fv fragment may be derived using recombinant techniques. The Fv fragment includes a non-covalent VH::VL heterodimer including an antigen-binding site that retains much of the antigen recognition and binding capabilities of the native antibody molecule.

The antibody, antibody fragment, or derivative may comprise a heavy chain and a light chain complementarity determining region ("CDR") set, respectively interposed between a heavy chain and a light chain framework ("FR") set which provide support to the CDRs and define the spatial relationship of the CDRs relative to each other. The DR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region. A polypeptide comprising a single CDR, (e.g., a CDR1, CDR2, or CDR3) may be referred to as a "molecular recognition unit." Crystallographic analyses of antigen-antibody complexes have demonstrated that the amino acid residues of CDRs form extensive contact with bound antigen, wherein the most extensive antigen contact is with the heavy chain CDR3. Thus, the molecular recognition units may be primarily responsible for the specificity of an antigen-binding site. In general, the CDR residues are directly and most substantially involved in influencing antigen binding.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, yeast or the like, display library); e.g., as available from various commercial vendors such as Cambridge Antibody Technologies (Cambridgeshire, UK), MorphoSys (Martinsreid/Planegg, Del.), Biovation (Aberdeen, Scotland, UK) Biolnvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1997) Microbiol. Immunol. 41:901-907; Sandhu et al. (1996) Crit. Rev. Biotechnol. 16:95-118; Eren et al. (1998) Immunol. 93:154-161) that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al. (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; Kenny et al. (1995) Bio/Technol. 13:787-790); B-cell selection (Steenbakkers et al. (1994) Molec. Biol. Reports 19:125-134 (1994)).

An affinity matured antibody may be produced by any one of a number of procedures that are known in the art. For example, see Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); Hawkins et al, J. Mol. Biol., 226: 889-896 (1992). Selective mutation at selective mutagenesis positions and at contact or hypermutation positions with an activity enhancing amino acid residue is described in U.S. Pat. No. 6,914,128 B1.

Antibody variants of the present invention can also be prepared using delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody variants also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., Adv. Exp. Med. Biol. (1999) 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to known methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally, part or all of the non-human or human CDR sequences are maintained while the non-human sequences of the variable and constant regions are replaced with human or other amino acids.

Small antibody fragments may be diabodies having two antigen-binding sites, wherein fragments comprise a heavy chain variable domain (VH) connected to a light chain variable domain (VL) in the same polypeptide chain (VH VL). See for example, EP 404,097; WO 93/11161; and Hollinger et al., (1993) Proc. Natl. Acad. Sci. USA 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which is hereby incorporated by reference in its entirety and discloses antibody variants that have one or more amino acids inserted into a hypervariable region of the parent antibody and a binding affinity for a target antigen which is at least about two fold stronger than the binding affinity of the parent antibody for the antigen.

The antibody may be a linear antibody. The procedure for making a linear antibody is known in the art and described in Zapata et al. (1995) Protein Eng. 8(10):1057-1062. Briefly, these antibodies comprise a pair of tandem Fd segments (VH-CH1-VH-CH1) which form a pair of antigen binding regions. Linear antibodies can be bispecific or monospecific.

The antibodies may be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

It may be useful to detectably or therapeutically label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample. Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 (131I), yttrium-90 (90Y), bismuth-212 (212Bi), bismuth-213 (213Bi), technetium-99m (99mTc), rhenium-186 (186Re), and rhenium-188 (188Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from chinese cobra (naj a naj a atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

The antibodies can be sequenced and replicated by recombinant or synthetic means. They also can be further sequenced down to the linear sequence of nucleotides that encode them. Accordingly, this invention provides these polynucleotides, alone or in combination with a carrier, vector or host cell as described above, that encode a sequence of an antibody of this invention.

Antibody production via the use of hybridoma technology, the selected lymphocyte antibody method (SLAM), transgenic animals, and recombinant antibody libraries is described in more detail below.

(a) Anti-RGMa Peptide or Neogenin Peptide Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, second edition, (Cold Spring Harbor Laboratory Press, Cold Spring Harbor, 1988); Hammerling, et al., In Monoclonal Antibodies and T-Cell Hybridomas, (Elsevier, N.Y., 1981). It is also noted that the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

In an embodiment, the present invention provides methods of generating monoclonal antibodies as well as antibodies produced by the method. The method may comprise culturing a hybridoma cell secreting an antibody of the invention wherein, preferably, the hybridoma is generated by fusing splenocytes isolated from an animal, e.g., a rat or a mouse, immunized with the RGMa peptide or Neogenin peptide with myeloma cells and then screening the hybridomas resulting from the fusion for hybridoma clones that secrete an antibody able to bind a polypeptide of the invention. Briefly, rats can be immunized with the RGMa peptide or Neogenin peptide. In a preferred embodiment, the RGMa peptide or Neogenin peptide is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks; however, a single administration of the polypeptide may also be used.

After immunization of an animal with the RGMa peptide or Neogenin peptide, antibodies and/or antibody-producing cells may be obtained from the animal. An anti-RGMa peptide or anti-Neogenin peptide antibody-containing serum is obtained from the animal by bleeding or sacrificing the animal. The serum may be used as it is obtained from the animal, an immunoglobulin fraction may be obtained from the serum, or the anti-RGMa peptide or anti-Neogenin peptide antibodies may be purified from the serum. Serum or immunoglobulins obtained in this manner are polyclonal, thus having a heterogeneous array of properties.

Once an immune response is detected, e.g., antibodies specific for the RGMa peptide or Neogenin peptide are detected in the rat serum, the rat spleen is harvested and splenocytes isolated. The splenocytes are then fused by well-known techniques to any suitable myeloma cells, for example, cells from cell line SP20 available from the American Type Culture Collection (ATCC, Manassas, Va., US). Hybridomas are selected and cloned by limited dilution. The hybridoma clones are then assayed by methods known in the art for cells that secrete antibodies capable of binding the RGMa peptide or Neogenin peptide. Ascites fluid, which generally contains high levels of antibodies, can be generated by immunizing rats with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using the RGMa peptide or Neogenin peptide, or a portion thereof, or a cell expressing the RGMa peptide or Neogenin peptide. In a preferred embodiment, the initial screening is performed using an enzyme-linked immunosorbent assay (ELISA) or a radioimmunoassay (MA), preferably an ELISA. An example of ELISA screening is provided in PCT Publication No. WO 00/37504.

Anti-RGMa peptide or anti-Neogenin peptide antibody-producing hybridomas are selected, cloned, and further screened for desirable characteristics, including robust hybridoma growth, high antibody production, and desirable antibody characteristics. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, hybridomas are rat hybridomas. In another embodiment, hybridomas are produced in a non-human, non-rat species such as mice, sheep, pigs, goats, cattle, or horses. In yet another preferred embodiment, the hybridomas are human hybridomas, in which a human non-secretory myeloma is fused with a human cell expressing an anti-RGMa peptide or anti-Neogenin peptide antibody.

Antibody fragments that recognize specific epitopes may be generated by known techniques. For example, Fab and F(ab')$_2$ fragments of the invention may be produced by proteolytic cleavage of immunoglobulin molecules, using enzymes such as papain (to produce two identical Fab fragments) or pepsin (to produce a F(ab')$_2$ fragment). A F(ab')$_2$ fragment of an IgG molecule retains the two antigen-binding sites of the larger ("parent") IgG molecule, including both light chains (containing the variable light chain and constant light chain regions), the CH1 domains of the heavy chains, and a disulfide-forming hinge region of the parent IgG molecule. Accordingly, a F(ab')$_2$ fragment is still capable of crosslinking antigen molecules like the parent IgG molecule.

(b) Anti-RGMa Peptide or Anti-Neogenin Peptide Monoclonal Antibodies Using SLAM

In another aspect of the invention, recombinant antibodies are generated from single, isolated lymphocytes using a procedure referred to in the art as the selected lymphocyte antibody method (SLAM), as described in U.S. Pat. No. 5,627,052; PCT Publication No. WO 92/02551; and Babcook et al., Proc. Natl. Acad. Sci. USA, 93: 7843-7848 (1996). In this method, single cells secreting antibodies of interest, e.g., lymphocytes derived from any one of the immunized animals are screened using an antigen-specific hemolytic plaque assay, wherein the RGMa peptide or Neogenin peptide, or a fragment thereof, is coupled to sheep red blood cells using a linker, such as biotin, and used to identify single cells that secrete antibodies with specificity for the RGMa peptide or the Neogenin peptide. Following identification of antibody-secreting cells of interest, heavy- and light-chain variable region cDNAs are rescued from the cells by reverse transcriptase-PCR (RT-PCR) and these variable regions can then be expressed, in the context of appropriate immunoglobulin constant regions (e.g., human, cow, dog, horse, cat, or pig constant regions), in mammalian host cells, such as COS or CHO cells. The host cells transfected with the amplified immunoglobulin sequences, derived from in vivo selected lymphocytes, can then undergo further analysis and selection in vitro, for example, by panning the transfected cells to isolate cells expressing antibodies to the RGMa peptide or Neogenin peptide. The amplified immunoglobulin sequences further can be manipulated in vitro, such as by in vitro affinity maturation method. See, for example, PCT Publication No. WO 97/29131 and PCT Publication No. WO 00/56772.

(c) Anti-RGMa Peptide or Anti-Neogenin Peptide Monoclonal Antibodies Using Transgenic Animals In another embodiment of the invention, antibodies are produced by immunizing a non-human animal comprising some, or all, of the human immunoglobulin locus with the RGMa peptide or the Neogenin peptide. In an embodiment, the non-human animal is a XENOMOUSE® transgenic mouse, an engineered mouse strain that comprises large fragments of the human immunoglobulin loci and is deficient in mouse antibody production. See, e.g., Green et al., Nature Genetics, 7: 13-21 (1994) and U.S. Pat. Nos. 5,916, 771; 5,939,598; 5,985,615; 5,998,209; 6,075,181; 6,091, 001; 6,114,598; and 6,130,364. See also PCT Publication Nos. WO 91/10741; WO 94/02602; WO 96/34096; WO 96/33735; WO 98/16654; WO 98/24893; WO 98/50433; WO 99/45031; WO 99/53049; WO 00/09560; and WO 00/37504. The XENOMOUSE® transgenic mouse produces an adult-like human repertoire of fully human antibodies, and generates antigen-specific human monoclonal antibodies. The XENOMOUSE® transgenic mouse contains approximately 80% of the human antibody repertoire through introduction of megabase sized, germline configuration YAC fragments of the human heavy chain loci and x light chain loci. See Mendez et al., Nature Genetics, 15: 146-156 (1997), Green and Jakobovits, J. Exp. Med., 188: 483-495 (1998), the disclosures of which are hereby incorporated by reference.

(d) Anti-RGMa Peptide or Anti-Neogenin Peptide Monoclonal Antibodies Using Recombinant Antibody Libraries In vitro methods also can be used to make the antibodies of the invention, wherein an antibody library is screened to identify an antibody having the desired RGMa peptide- or Neogenin peptide-binding specificity. Methods for such screening of recombinant antibody libraries are well known in the art and include methods described in, for example, U.S. Pat. No. 5,223,409 (Ladner et al.); PCT Publication No. WO 92/18619 (Kang et al.); PCT Publication No. WO 91/17271 (Dower et al.); PCT Publication No. WO 92/20791 (Winter et al.); PCT Publication No. WO 92/15679 (Markland et al.); PCT Publication No. WO 93/01288 (Breitling et al.); PCT Publication No. WO 92/01047 (McCafferty et al.); PCT Publication No. WO 92/09690 (Garrard et al.); Fuchs et al., Bio/Technology, 9: 1369-1372 (1991); Hay et al., Hum. Antibod. Hybridomas, 3: 81-85 (1992); Huse et al., Science, 246: 1275-1281 (1989); McCafferty et al., Nature, 348: 552-554 (1990); Griffiths et al., EMBO J., 12: 725-734 (1993); Hawkins et al., J. Mol. Biol., 226: 889-896 (1992); Clackson et al., Nature, 352: 624-628 (1991); Gram et al., Proc. Natl. Acad. Sci. USA, 89: 3576-3580 (1992); Garrard et al., Bio/Technology, 9: 1373-1377 (1991); Hoogenboom et al., Nucl. Acids Res., 19: 4133-4137 (1991); Barbas et al., Proc. Natl. Acad. Sci. USA, 88: 7978-7982 (1991); US Patent Application Publication No. 2003/0186374; and PCT Publication No. WO 97/29131, the contents of each of which are incorporated herein by reference.

The recombinant antibody library may be from a subject immunized with the RGMa peptide or Neogenin peptide, or a portion of the RGMa peptide or Neogenin peptide. Alternatively, the recombinant antibody library may be from a naive subject, i.e., one who has not been immunized with the RGMa peptide or the Neogenin peptide, such as a human antibody library from a human subject who has not been immunized with the RGMa peptide or Neogenin peptide. Antibodies of the invention are selected by screening the recombinant antibody library with the peptide comprising the RGMa peptide or the Neogenin peptide to thereby select those antibodies that recognize the RGMa peptide or the Neogenin peptide. Methods for conducting such screening and selection are well known in the art, such as described in the references in the preceding paragraph. To select antibodies of the invention having particular binding affinities for the RGMa peptide or the Neogenin peptide, such as those that dissociate from the RGMa peptide or the Neogenin peptide with a particular $K_{off}$ rate constant, the art-known method of surface plasmon resonance can be used to select antibodies having the desired $K_{off}$ rate constant. To select antibodies of the invention having a particular neutralizing activity for the RGMa peptide or the Neogenin peptide, such as those with a particular $IC_{50}$, standard methods known in the art for assessing the inhibition of RGMa or Neogenin activity may be used.

In one aspect, the invention pertains to an isolated antibody, or an antigen-binding portion thereof, that binds the RGMa peptide or Neogenin peptide. Preferably, the antibody is a neutralizing antibody. In various embodiments, the antibody is a recombinant antibody or a monoclonal antibody.

For example, antibodies of the present invention can also be generated using various phage display methods known in the art. In phage display methods, functional antibody domains are displayed on the surface of phage particles which carry the polynucleotide sequences encoding them. Such phage can be utilized to display antigen-binding domains expressed from a repertoire or combinatorial antibody library (e.g., human or murine or cow, dog, horse, cat, or pig). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv, or disulfide stabilized Fv antibody domains recombinantly fused to either the phage gene III or gene VIII protein. Examples of phage display methods that can be used to make the antibodies of the present invention include those disclosed in Brinkmann et al., J. Immunol. Methods, 182: 41-50 (1995); Ames et al., J. Immunol. Methods, 184:177-186 (1995); Kettleborough et al., Eur. J. Immunol., 24: 952-958 (1994); Persic et al., Gene, 187: 9-18 (1997); Burton et al., Advances in Immunology, 57: 191-280 (1994); PCT Publication No. WO 92/01047; PCT Publication Nos. WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab', and F(ab')2 fragments can also be employed using methods known in the art such as those disclosed in PCT publication No. WO 92/22324; Mullinax et al., BioTechniques, 12(6): 864-869 (1992); Sawai et al., Am. J. Reprod. Immunol., 34: 26-34 (1995); and Better et al., Science, 240: 1041-1043 (1988). Examples of techniques which can be used to produce single-chain Fvs and antibodies include those described in U.S. Pat. Nos. 4,946,778 and 5,258,498; Huston et al., Methods in Enzymology, 203: 46-88 (1991); Shu et al., Proc. Natl. Acad. Sci. USA, 90: 7995-7999 (1993); and Skerra et al., Science, 240: 1038-1041 (1988).

Alternative to screening of recombinant antibody libraries by phage display, other methodologies known in the art for screening large combinatorial libraries can be applied to the identification of antibodies of the invention. One type of alternative expression system is one in which the recombinant antibody library is expressed as RNA-protein fusions, as described in PCT Publication No. WO 98/31700 (Szostak and Roberts), and in Roberts and Szostak, Proc. Natl. Acad. Sci. USA, 94: 12297-12302 (1997). In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above. A preferred example of this methodology, is PROfusion display technology.

In another approach, the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine or bovine, canine, equine, feline, or porcine). Examples of yeast display methods that can be used to make the antibodies of the present invention include those disclosed in U.S. Pat. No. 6,699,658 (Wittrup et al.) incorporated herein by reference.

(b) Production of Recombinant RGMa Peptide or Neogenin Peptide Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the invention include Chinese Hamster Ovary (CHO cells) (including dhfr-CHO cells, described in Urlaub and Chasin, Proc. Natl. Acad. Sci. USA, 77: 4216-4220 (1980), used with a DHFR selectable marker, e.g., as described in Kaufman and Sharp, J. Mol. Biol., 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention (i.e., binds the RGMa peptide or the Neogenin peptide) and the other heavy and light chain are specific for an antigen other than the RGMa peptide or the Neogenin peptide by crosslinking an antibody of the invention to a second antibody by standard chemical cross-linking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

(a) Humanized Antibody

The humanized antibody may be an antibody or a variant, derivative, analog or portion thereof which immunospecifically binds to an antigen of interest and which comprises a framework (FR) region having substantially the amino acid sequence of a human antibody and a complementary determining region (CDR) having substantially the amino acid sequence of a non-human antibody. The humanized antibody may be from a non-human species antibody that binds the desired antigen having one or more complementarity determining regions (CDRs) from the non-human species and framework regions from a human immunoglobulin molecule.

As used herein, the term "substantially" in the context of a CDR refers to a CDR having an amino acid sequence at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. According to one aspect, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or of a heavy chain.

The humanized antibody can be selected from any class of immunoglobulins, including IgM, IgG, IgD, IgA and IgE, and any isotype, including without limitation IgG 1, IgG2, IgG3, and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The humanized antibody may be designed to minimize unwanted immunological response toward rodent anti-human antibodies, which limits the duration and effectiveness of therapeutic applications of those moieties in human recipients. The humanized antibody may have one or more amino acid residues introduced into it from a source that is non-human. These non-human residues are often referred to as "import" residues, which are typically taken from a variable domain. Humanization may be performed by substituting hypervariable region sequences for the corresponding sequences of a human antibody. Accordingly, such "humanized" antibodies are chimeric antibodies wherein substantially less than an intact human variable domain has been substituted by the corresponding sequence from a non-human species. For example, see U.S. Pat. No. 4,816,567, the contents of which are herein incorporated by reference. The humanized antibody may be a human antibody in which some hypervariable region residues, and possibly some FR residues are substituted by residues from analogous sites in rodent antibodies. Humanization or engineering of antibodies of the present invention can be performed using any known method, such as but not limited to those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

The humanized antibody may retain high affinity for the RGMa peptide or the Neogenin peptide and other favorable biological properties. The humanized antibody may be prepared by a process of analysis of the parental sequences and various conceptual humanized products using three-dimensional models of the parental and humanized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristics, such as increased affinity for the RGMa peptide or Neogenin peptide, is achieved. In general, the hypervariable region residues may be directly and most substantially involved in influencing antigen binding.

As an alternative to humanization, human antibodies (also referred to herein as "fully human antibodies") can be generated. For example, it is possible to isolate human antibodies from libraries via PROfusion and/or yeast related technologies. It is also possible to produce transgenic animals (e.g. mice that are capable, upon immunization, of producing a full repertoire of human antibodies in the absence of endogenous immunoglobulin production. For example, the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. The humanized or fully human antibodies may be prepared according to the methods described in U.S. Pat. Nos. 5,770,429; 5,833,985; 5,837,243; 5,922,845; 6,017,517; 6,096,311; 6,111,166; 6,270,765; 6,303,755; 6,365,116; 6,410,690; 6,682,928; and 6,984,720, the contents each of which are herein incorporated by reference.

c. Neuronal Cell Survival

As described above, the method of modulating may promote neuronal cell survival in the subject. Neuronal cell survival may be promoted by disrupting or blocking the cis interaction between RGMa and Neogenin, and/or disrupting lipid rafts, and/or reducing the level of cholesterol within lipid rafts. The agent described above may disrupt or block the cis interaction between RGMa and Neogenin, and/or disrupt lipid rafts, and/or reduce the level of cholesterol within lipid rafts.

The method of modulating may promote neuronal cell survival after optic nerve injury, spinal cord injury, or a combination thereof. The method of modulating may promote neuronal cell survival in a subject suffering from retinitis pigmentosa, ischemia (e.g., stroke), or multiple sclerosis. Methods of treating optic nerve injury, spinal cord injury, retinitis pigmentosa, ischemia (e.g., stroke), or multiple sclerosis are described below in more detail.

The method of modulating may include promoting neuronal cell survival in the subject by at least about 1.5-fold, 2.0-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, or about 10.0-fold. The method of modulating may include promoting neuronal cell survival in the subject by at least about 2.0-fold or 3.0-fold.

The method of modulating may include increasing neuronal cell survival in the subject as compared neuronal cell survival in a subject not administered the agent. The method of modulating may include increasing neuronal cell survival in the subject by at least about 1.5-fold, 2.0-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, or about 10.0-fold as compared to neuronal cell survival in the subject not administered the agent. The method of modulating may include increasing neuronal cell survival in the subject by at least about 2.0-fold or 3.0-fold as compared to neuronal cell survival in the subject not administered the agent.

d. Promotion of Axon Growth and/or Regeneration

The method of modulating may promote axon growth and/or regeneration in the subject. Axon growth and/or regeneration may be promoted by disrupting or blocking the cis interaction between RGMa and Neogenin, and/or disrupting lipid rafts, and/or reducing the level of cholesterol within lipid rafts. The agent described above may disrupt or block the cis interaction between RGMa and Neogenin, and/or disrupt lipid rafts, and/or reduce the level of cholesterol within lipid rafts.

The method of modulating may promote axon growth and/or regeneration after optic nerve injury, spinal cord injury, or a combination thereof. The method of modulating may promote axon growth and/or regeneration in the subject suffering from retinitis pigmentosa, ischemia (e.g., stroke), or multiple sclerosis. Methods of treating optic nerve injury, spinal cord injury, retinitis pigmentosa, ischemia (e.g., stroke), or multiple sclerosis are described below in more detail.

3. Method of Treatment

Also provided herein is a method of treating a disease in a subject in need thereof. The method of treating may apply the method of modulating the cis interaction between RGMa and Neogenin, and/or disrupting lipid rafts, and/or reducing the level of cholesterol within lipid rafts described above. The method of treating may include administering the agent described above to the subject.

Modulating the cis interaction between RGMa and Neogenin, and/or disrupting lipid rafts, and/or reducing the level of cholesterol within lipid rafts may be beneficial to diseases. The disease may include, but is not limited to, retinitis pigmentosa, ischemia (e.g., stroke), multiple sclerosis, spinal cord injury and optic nerve injury, each of which is described below in more detail.

a. Retinitis Pigmentosa

The method of treatment may include treating retinitis pigmentosa in the subject. The method of treating retinitis pigmentosa may include administering the agent to subject. The agent may modulate the cis interaction between RGMa and Neogenin, and/or disrupt lipid rafts. and/or reduce the level of cholesterol within lipid rafts. Modulation may include disrupting or blocking the cis interaction between RGMa and Neogenin, and/or disrupting lipid rafts, and/or reducing the level of cholesterol within lipid rafts. Disrupting or blocking the cis interaction, and/or disrupting lipid rafts, and/or reducing the level of cholesterol within lipid rafts may promote neuronal cell survival and axon growth and/or regeneration in the subject. Accordingly, the method of treatment may promote neuronal cell survival and axon growth and/or regeneration in the subject suffering from retinitis pigmentosa.

The neuronal cells may be photoreceptor cells. Accordingly, the method of treating retinitis pigmentosa may promote survival of photoreceptor cells in the subject administered the agent.

The method of treatment may increase the outer nuclear layer in the subject by at least about 1.5-fold, 2.0-fold, 2.5-fold, 3.0-fold, 3.5-fold, 4.0-fold, 4.5-fold, 5.0-fold, 5.5-fold, or 6.0-fold as compared to the outer nuclear layer in a subject not administered the agent.

b. Ischemia

The method of treatment may include treating ischemia in the subject. The method of treating ischemia may include administering the agent to the subject. The agent may modulate the cis interaction between RGMa and Neogenin, and/or disrupt lipid rafts, and/or reduce the level of cholesterol within lipid rafts. Modulation may include disrupting or blocking the cis interaction between RGMa and Neogenin, and/or disrupting lipid rafts, and/or reducing the level of cholesterol within lipid rafts. Disrupting or blocking the cis interaction, and/or disrupting lipid rafts, and/or reducing the level of cholesterol within lipid rafts may promote neuronal cell survival and axon growth and/or regeneration in the subject. Accordingly, the method of treatment may promote neuronal cell survival and axon growth and/or regeneration after ischemic injury in the subject.

Ischemia may include, but is not limited to, stroke. The ischemia may be stroke. Accordingly, the method may include treating stroke by administering the agent to the subject.

The method of treating stroke may reduce brain edema in the subject as compared to brain edema of a subject suffering from stroke and not administered the agent. The method of treating stroke may reduce infarct volume in the subject as compared to an infarct volume of the subject suffering from stroke and not administered the agent. The method of treating stroke may reduce behavioral deficits resulting from the stroke in the subject as compared to behavioral deficits in the subject suffering from stroke and not administered the agent.

c. Multiple Sclerosis

The method of treatment may include treating multiple sclerosis in the subject. The method of treating multiple sclerosis may include administering the agent to the subject. The agent may modulate the cis interaction between RGMa and Neogenin, and/or disrupt lipid rafts, and/or reduce the level of cholesterol within lipid rafts. Modulation may include disrupting or blocking, the cis interaction between RGMa and Neogenin, and/or disrupting lipid rafts and/or, reducing the level of cholesterol within lipid rafts. Disrupting or blocking the cis interaction, and/or disrupting lipid rafts, and/or reducing the level of cholesterol within lipid rafts may promote neuronal cell survival and axon growth and/or regeneration in the subject. Accordingly, the method of treatment may promote neuronal cell survival and axon growth and/or regeneration in the subject suffering from multiple sclerosis.

The method of treatment may reduce neurodegeneration in the subject as compared to neurodegeneration in the subject suffering from multiple sclerosis and not administered the agent.

d. Spinal Cord Injury

The method of treatment may include treating spinal cord injury in the subject. The method of treating spinal cord injury may include administering the agent to the subject. The agent may modulate the cis interaction between RGMa and Neogenin, and/or disrupt lipid rafts, and/or reduce the level of cholesterol within lipid rafts. Modulation may include disrupting or blocking the cis interaction between RGMa and Neogenin, and/or disrupting lipid rafts, and/or reducing the level of cholesterol within lipid rafts. Disrupting or blocking the cis interaction, and/or disrupting lipid rafts, and/or reducing the level of cholesterol within lipid rafts may promote neuronal cell survival and axon growth and/or regeneration in the subject. Accordingly, the method of treatment may promote neuronal cell survival and axon growth and/or regeneration after spinal cord injury in the subject. By promoting axon growth and/or regeneration in the subject, the method of treatment may restore locomoter activity in the subject. The method of treatment may partially or completely restore locomoter activity in the subject after the spinal cord injury.

e. Optic Nerve Injury

The method of treatment may include treating optic nerve injury in the subject. The method of treating optic nerve injury may include administering the agent to the subject. The agent may modulate the cis interaction between RGMa and Neogenin, and/or disrupt lipid rafts, and/or reduce the level of cholesterol within lipid rafts. Modulation may include disrupting or blocking the cis interaction between RGMa and Neogenin, and/or disrupting lipid rafts, and/or reducing the level of cholesterol within lipid rafts. Disrupting or blocking the cis interaction, and/or disrupting lipid rafts, and/or reducing the level of cholesterol within lipid rafts may promote neuronal cell survival and axon growth and/or regeneration in the subject. Accordingly, the method of treatment may promote neuronal cell survival and axon growth and/or regeneration after optic nerve injury in the subject.

The present invention has multiple aspects, illustrated by the following non-limiting examples.

4. Pharmaceutical Compositions

The above-described agent may be a component in a pharmaceutical composition. The pharmaceutical composition may also contain a pharmaceutically acceptable carrier. The pharmaceutical compositions comprising the agent of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more agents of the invention. In another embodiment, the pharmaceutical composition comprises one or more agents of the invention and one or more prophylactic or therapeutic agents other than agent of the invention for treating a disorder in which modulating the cis interaction between RGMa and Neogenin, and/or disrupting lipid rafts, and/or reducing the level of cholesterol in lipid rafts may be beneficial. In a further embodiment, the prophylactic or therapeutic agents are known to be useful for, or have been, or are currently being used in the prevention, treatment, management, or amelioration of a disorder, or one or more symptoms thereof. In accordance with these embodiments, the composition may further comprise of a carrier, diluent, or excipient.

The agent of the invention can be incorporated into pharmaceutical compositions suitable for administration to a subject. Typically, the pharmaceutical composition comprises an agents of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives, or buffers, which enhance the shelf life or effectiveness of the agent.

Various delivery systems are known and can be used to administer one or more agents of the invention or the combination of one or more agents of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the agent, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidurala administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO97/32572; WO97/44013; WO98/31346; and WO99/66903, each of which is incorporated herein by reference in their entireties. In one embodiment, an agent of the invention or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the agent of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more agents of the invention is administered locally to the affected area to a subject to prevent, treat, manage, and/or ameliorate a disorder or a symptom thereof.

In another embodiment, the agent can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO99/15154; and PCT Publication No. WO99/20253. Examples of polymers used in sustained release formulations include, but are not limited to, poly(2-hydroxy ethyl methacry-late), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a particular embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more agents of the invention. See, e.g., U. S. Pat. No. 4,526,938, PCT publication WO91/05548, PCT publication WO96/20698, Ning et al., 1996, "Intratumoral Radioimmunotheraphy of a Human Colon Cancer Xenograft Using a Sustained-Release Gel," Radiotherapy &Oncology 39:179-189; Song et al., 1995, "Antibody Mediated Lung Targeting of Long-Circulating Emulsions," PDA Journal of Pharmaceutical Science & Technology 50:372-397; Cleek et al., 1997, "Biodegradable Polymeric Carriers for a bFGF Antibody for Cardiovascular Application," Pro. Int'l. Symp. Control. Rel. Bioact. Mater. 24:853-854; and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entireties.

In a specific embodiment, where the composition of the invention is a nucleic acid encoding the agent described above, the nucleic acid can be administered in vivo to promote expression of its encoded antibody, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. Inhalation may include, in some embodiments, use of a vaporizer to administer the pharmaceutical composition to the subject. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, for example in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference their entireties. In a specific embodiment, an antibody of the invention and/or composition of the invention is administered using Alkermes AIR pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the agents, or pharmaceutical compositions, of the invention is packaged in a hermetically sealed container such as an ampoule or sachette indicating the quantity of the antibody. In one embodiment, one or more of the agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. In one embodiment, one or more of the agents or pharmaceutical compositions of the invention is supplied as a dry sterile lyophilized powder in a hermetically sealed container at a unit dosage of at least 5 mg, for example at least 10 mg, at least 15 mg, at least 25 mg, at least 35 mg, at least 45 mg, at least 50 mg, at least 75 mg, or at least 100 mg. The lyophilized agents or pharmaceutical compositions of the invention should be stored at between 2° C. and 8° C. in its original container and the agents, or pharmaceutical compositions of the invention should be administered within 1 week, for example within 5 days, within 72 hours, within 48 hours, within 24 hours, within 12 hours, within 6 hours, within 5 hours, within 3 hours, or within 1 hour after being reconstituted. In an alternative embodiment, one or more of the agents or pharmaceutical compositions of the invention is supplied in liquid form in a hermetically sealed container indicating the quantity and concentration of the antibody. In a further embodiment, the liquid form of the administered composition is supplied in a hermetically sealed container at least 0.25 mg/ml, for example at least 0.5 mg/ml, at least 1 mg/ml, at least 2.5 mg/ml, at least 5 mg/ml, at least 8 mg/ml, at least 10 mg/ml, at least 15 mg/ml, at least 25 mg/ml, at least 50 mg/ml, at least 75 mg/ml or at least 100 mg/ml. The liquid form should be stored at between 2° C. and 8° C. in its original container.

The agents of the invention can be incorporated into a pharmaceutical composition suitable for parenteral administration. In one aspect, agents will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the tonicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies of the invention prepared as an injectable solution for parenteral administration, can further comprise an agent useful as an adjuvant, such as those used to increase the absorption, or dispersion of the antibody. A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (See International Appln. Publication No. WO 04/078140 and U.S. Patent Appln. Publication No. US2006104968, incorporated herein by reference.)

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Compositions can be in the form of injectable or infusible solutions, such as compositions similar to those used for passive immunization of humans or mammals (e.g., bovine, canine, equine, feline, and porcine) with other antibodies. In one embodiment, the antibody is administered by intravenous infusion or injection. In another embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., a binding protein, e.g. an agent, of the present invention) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, methods of preparation comprise vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The agents of the present invention can be administered by a variety of methods known in the art. For many therapeutic applications, the route/mode of administration may be subcutaneous injection, intravenous injection, inhalation, or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, an agent of the invention may be orally administered, for example, with an inert diluent or an assimilable edible carrier. The agent (and other ingredients, if desired) may also be enclosed in a hard or soft shell gelatin capsule, compressed into tablets, or incorporated directly into the subject's diet. For oral therapeutic administration, the agent may be incorporated with excipients and used in the form of ingestible tablets, buccal tablets, troches, capsules, elixirs, suspensions, syrups, wafers, and the like. To administer an agent of the invention by other than parenteral administration, it may be necessary to coat the agent with, or co-administer the agent with, a material to prevent its inactivation.

In certain embodiments, an agent of the invention is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

In a specific embodiment, nucleic acid sequences comprising nucleotide sequences encoding an agent of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded agent of the invention that mediates a prophylactic or therapeutic effect.

Any of the methods for gene therapy available in the art can be used according to the present invention. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, Science 260:926-932 (1993); and Morgan and Anderson, 1993, Ann. Rev. Biochem. 62:191-217; May, 1993, TIBTECH 11(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990). Detailed description of various methods of gene therapy are disclosed in US20050042664 A1 which is incorporated herein by reference.

Agents of the invention can be used alone or in combination to treat diseases or conditions associated with pain, or any other disease or condition associated with RGMa or Neogenin. It should further be understood that the combinations are those combinations useful for their intended purpose.

The pharmaceutical compositions may include a "therapeutically effective amount" or a "prophylactically effective amount" of an agent of the invention. A "therapeutically effective amount" refers to an amount effective, at dosages and for periods of time necessary, to achieve the desired therapeutic result. A therapeutically effective amount of the agent may be determined by a person skilled in the art and may vary according to factors such as the disease state, age, sex, and weight of the individual, and the ability of the antibody to elicit a desired response in the individual. A therapeutically effective amount is also one in which toxic or detrimental effects, if any, of the agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of the agent is a dose of between 0.1 and 200 mg/kg, for example between 0.1 and 10 mg/kg. The therapeutically or prophylactically effective amount of the agent may be between 1 and 200 mg/kg, 10 and 200 mg/kg, 20 and 200 mg/kg, 50 and 200 mg/kg, 75 and 200 mg/kg, 100 and 200 mg/kg, 150 and 200 mg/kg, 50 and 100 mg/kg, 5 and 10 mg/kg, or 1 and 10 mg/kg. It is to be noted that dosage values may vary with the type and severity of the condition to be alleviated. Further, the agent dose may be determined by a person skilled in the art and may vary according to factors such as the disease state, age, sex, and weight of the individual, and the ability of the agent to elicit a desired response in the individual. The dose is also one in which toxic or detrimental effects, if any, of the agent are outweighed by the therapeutically beneficial effects. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

5. Examples

Example 1

Materials and Methods for Examples 2-11

Provided herein in Example 1 are materials and methods that were used in the experiments described below in Examples 2-11.

Retinal Explants Outgrowth Assay and Immunocolocalization.

Poly-L-Lysine (SIGMA; 10 µg/ml) coated glass coverslips were treated with Laminin (Invitrogen; 10 µg/ml) and RGMa proteins (5 µg/ml) and incubated for 3 hours at room temperature. Temporal retinal explants were cultured on protein-coated surfaces for 18 hours. To disrupt the lipid rafts, explants were pretreated with 10 mM methyl-β-cyclodextrin (MβCD) for 12 minutes or 2 U/ml cholesterol oxidase (CO) for 1 hour at 37° C. Explants were then fixed with 4% paraformaldehyde (PFA) and stained with Alexa488-phalloidin. Fiber length was quantified using Image Pro 5.0. For immunolocalization, explants were treated with Cholera Toxin B-FITC (C1655; Sigma; 10 mg/mL) and patched, fixed and stained with Neogenin antibody. Retinal ganglion cells (RGCs) were electroporated with RGMa-His and cultured for 18 hours. The cells were fixed and stained with Neogenin and His-tag antibodies.

Lipid Raftfractionation of Cells and Tecta.

Injected chick E8 tecta (4Ig, 2 mg/mL; N-raft, 1 mg/mL; methyl-β-cyclodextrin (10 mM)) or transfected cells (Neogenin and RGMa) were collected 24 hours later, lysed and placed at the bottom of a sucrose density gradient (0.9-0.8-0.75-0.7-0.6-0.5-0.4-0.2 M) and centrifuged at 38,000 rpm for 16 hours in SW 60 rotor (Beckman Instruments Inc.).

Spinal cord injury (SCI).

The spinal cord was injured by clip compression at spinal cord level T8 with a 20 g force. The 4Ig or vehicle was injected intraspinally immediately following SCI. 2 injections (250 ng/µL, 3 µL each) were made 1 mm rostral and 1 mm caudal to the lesion site and adjacent to the midline vein. Immediately following SCI, the 4Ig treated rats also received a 1 mg/kg dose of 4Ig intravenously (i.v.) via the intrajugular vein and subsequent i.v. injections weekly for 2 more weeks. Rats in the MβCD group received intraperitoneal (i.p.) injection of MβCD at 1000 mg/kg/week immediately following SCI and then daily i.p. injections until sacrifice. Control rats received equivalent vehicle volumes as described above.

Intrathecal Infusion.

To assess local delivery of 4Ig, 19 adult female Wistar rats were injured and injected rostral and caudal to the lesion site with 4Ig or PBS. Immediately after the intraspinal injections, 4Ig or PBS was delivered intrathecally and then continuously for 14 days (0.5 µL/hour) via the catheter and pump system.

Functional Analysis.

Functional tests were performed before the injury, 1 day, and then weekly for 6 weeks post-SCI. Locomotor function was evaluated using the BBB locomotor rating scale. A score of 0 indicates no hindlimb movement, a score of 21 indicates unimpaired locomotion as observed in Control. Motor subscores were determined to assess toe clearance, predominant paw position and absence of instability. A maximal motor subscore of 7 means normal locomotion.

Ladder-walk analysis was done to assess fine motor functions. At 1 week post-SCI and weekly thereafter, rats with a BBB score greater than 10 were placed on the horizontal ladder-walk apparatus and 3 test runs were recorded. Recordings were analyzed in slow motion; the number of footfalls per hindlimb was recorded and the average was calculated for each rat per week.

Cloning and Purification of Proteins.

The Ig domain of Neogenin (4Ig) as well as the Ig domain of DCC (4Ig) were cloned in pSectag 2B vector (Invitrogen) with a 6-His tag at the N-terminus and in frame with the myc and 6-His tags of the vector at the C-terminus. N-RGMa constructs, N-RGMa$^{28-73}$ (N-Raft), N-RGMa$^{50-99}$, and N-RGMa$^{77-113}$ (N-inh.) were all cloned with a 6-His tag at the N-terminus except N-RGMa$^{77-113}$, which also contained a myc tag and 6-His tags at the C-terminus. Cells were transfected and media collected 48 hrs later and purified on Ni-NTA beads according to manufacturer's protocols (Qiagen). Proteins were dialyzed in PBS before being used in all assays.

Retinal explants outgrowth assay. Poly-L-Lysine (PLL; SIGMA; 10 µg/ml) coated glass coverslips were treated with Laminin (10 µg/ml; Invitrogen) and RGMa proteins (5 µg) and incubated for 3 hrs at room temperature. PLL treated coverslips were coated with myelin overnight (6 µg/cm2), followed by coating with Laminin. Temporal retinal explants were cultured on either myelin or protein-coated surfaces in DMEM F-12 media (2% chick serum, 10% FBS) for 18 h. To disrupt rafts, explants were pre-treated with 10 mM MβCD for 12 min or 2 U/ml CO for 1 h at 37° C., washed, and cultured on protein coated coverslips. Explants were then fixed with 4% PFA and stained with Alexa488-fluorphalloidin (1:50; Molecular Probes). Fiber length was quantified using Image Pro 5.0.

Pull-Down Assay.

Proteins were coupled to activated CNBr Sepharose beads (Pharmacia) according to supplier instructions. Supernatants from transfected cells were added to coupled beads for 2 h at room temperature (RT). Beads were then washed 6× with PBS plus 0.02% Tween 20, and SDS loading buffer was added. Samples were boiled and subjected to Western blotting.

Lipid Raft Fractionation of HEK Cells and Tecta.

Proteins (4Ig, 2 mg/ml; N-Raft, 1 mg/mL; RGMaΔ, 5 mg/ml; methyl-β-cyclodextrin (10 mM)) were injected in chick E8 optic tectum and tecta were collected 24 hrs later. HEK cells were transfected with Neogenin and different RGMa constructs and collected 48 hrs later. For treatment with RGMaΔ, Neogenin transfected cells were treated with RGMaΔ (2 mg/ml) and BMP-2 (100 nM) and further incubated for 1 hr at 37° C. Tecta (3 tecta for each set of experiment) and/or cells were solubilized in chilled buffer (25 mM Tris-HCl, pH 7.4, 150 mM NaCl, 5 mM EDTA and protease inhibitor cocktail) and passed through G25 and G30 needles, respectively, and centrifuged at 800 g for 10 min at 4° C. Cold Triton X-100 was added to the post nuclear supernatant to a final concentration of 1% and incubated on ice for 1 hour. 2× volume of 2M sucrose was added and sample placed at the bottom of a sucrose density gradient (0.9-0.8-0.75-0.7-0.6-0.5-0.4-0.2 M) and centrifuged at 38,000 rpm for 16 hours in SW 60 rotor (Beckman Instruments Inc.). 400 µl fractions were collected from top (top numbered 1 and next eight fractions numbered consequently) and stored at −80° C.

In Ovo Electroporation and DiI Tracing.

Eggs (White Leghorn) were incubated at 38° C. in a high humidity chamber. A small amount of viral solution (viral titers of 1×10$^8$ IU/ml) was mixed with ⅒ volume of 0.25% fast green solution (Molecular Probes) and injected in the tectum at E1.5. Eggs were further incubated until E15, when a small DiI crystal (Molecular Probes) was placed in the temporo-dorsal part of the right eye. At E17, embryos were sacrificed and the tecta fixed in 4% PFA. DiI tracing was viewed under the microscope (Olympus BX61) after cutting the tecta in half. Digital Images of the tecta were taken and processed using Photoshop (Adobe). Alternatively, plasmid constructs were electroporated into the optic vesicle to restrict expression to the eye and tracing performed as above.

Statistical Analysis.

Statistical analysis of retinal outgrowth assays was performed using Student's two-tail t-test using Excel (Microsoft). Results were expressed as the mean±SEM (n=at least 3 independent experiments; 2 duplicates per independent experiment, >10 explants per duplicate).

Immunocolocalization Protocol.

Retinal explants were cultured on Laminin for 18 hours at 37° C., treated with Cholera Toxin B-FITC (C1655; Sigma; 10 mg/mL) followed by patching with anti-Cholera Toxin B antibody (ab35988; abcam; 1:1000), and fixed in 4% PFA. For co-localization staining with Neogenin, explants were blocked with 5% FBS/PBS and incubated with a Neogenin antibody (H-175; Santa Cruz; 1:200), followed by anti-rabbit Alexa 555 secondary antibody (molecular probes; 1:250). For co-localization of Cholera Toxin and F-actin, explants were treated with Cholera Toxin and patched as above and stained with Alexa555-flour-phalloidin. For co-localization of Neogenin and RGMa-His, DRG neurons were prepared from chick E8 embryos, electroporated with RGMa-His using Amaxa Nucleofector Kit (Lonza), plated on Laminin coated coverslips and cultured for 18 hrs. The cells were fixed, washed, blocked in 5% FBS and co-stained with Neogenin (H-175; Santa Cruz; 1:200) and His antibody (abm; 1:1000). DRGs were incubated with anti-rabbit Alexa 555 and anti-mouse Alexa 488 antibodies (molecular probes; 1:250).

Image Analysis.

Growth cones of retinal ganglion cells and DRG neurons were imaged on Olympus BX61 microscope. Z stack images were taken in both the red (Neogenin) and green (Cholera Toxin B or RGMa) channels, and combined into a single layer by using the "maximum projection over z" features of the program. The degree of colocalization of the two colors was quantified using "Image J with intensity correlation analysis plugin". Intensity correlation analysis (ICA) measured whether the intensities of the two channels varied in synchrony (dependent staining) or asynchronously (segregated staining).

Quantitative Co-Localization Analysis.

The quantitative colocalization analysis was done using ImageJ software with Intensity Correlation Analysis (ICA) plugin (WCIF ImageJ). The ICQ values range between −0.5 and +0.5. Random staining: ICQ about 0; Segregated staining: 0>ICQ>−0.5; Dependent staining: 0<ICQ<+0.5. Tests for significance were performed by means of the normal approximation of the sign test (P sign test).

Cell Death Assay.

HEK293 cells that stably expressed RGMa were used in this assay. Transient transfection of a Neogenin expressing plasmid (1 µg/µl) was done using lipofectamin 2000. After transfection, cells were incubated for 24 h in 5% CO2 and trypan blue (SIGMA) staining was performed to assess cellular death.

Dissociated Retinal Ganglion Cells Rescue Assay.

Dissociated retinal ganglion cells were prepared from E7 chick embryos. Retinas were dissected out in HBSS, trypsinized and cultured in DMEM/F12 media with 10% calf serum and N2 supplement. The cells were nucleofected with pRFP control shRNA, shRNA37 against chick RGMa, and both shRNA37 and mouse RGMa using nuclefector kit (Amaxa Chicken Neuron Nucleofector kit, Lonza). The cells were plated (500,000 cells/well) on coverslips coated with either laminin (10 µg/ml) or laminin with N-RGMa (10 µg), C-RGMa (10 µg) or RGMaΔ (20 µg) proteins and grown for 18 hrs. The cells were fixed in 4% paraformaldehyde and stained with β-tubulin antibody (Covance; 1:1000) for 1 hour at RT, followed by Alexa fluor488 goat anti mouse secondary antibody was used (1:500) for 1 hr at RT. The images of transfected cells were taken using Olympus fluorescence microscope (BX61). The length of axons of transfected cells was measured from each condition (at least 40 cells/condition/experiment) using cellSens (Olympus).

Staining of RGMa in Growth Cones of Dissociated Retinal Ganglion Cells.

To view RGMa silencing in growth cones, dissociated retinal ganglion cells were prepared as above and nucleofected with shRNA37 and 21 and control shRNA all expressing RFP. The nucleofected cells were plated on coverslips coated with laminin (10 µg/ml), cultured and fixed after 18 hrs using 4% paraformaldehyde and stained using RGMa antibody (7A2: supernatant from hybridoma cells targeting the C terminal part of RGMa) overnight at 4° C. Cells were further incubated with Alexa-fluor 488 anti-mouse secondary antibody for 1 hr at RT. The growth cones from the nucleofected retinal ganglion cells were imaged using Olympus fluorescence microscope (BX61).

Western Blot Analysis of RGMa Downregulation.

HEK cells were co-transfected with either chick RGMa or mouse RGMa tagged with HIS antibody and control shRNA, shRNA37, shRNA21 using PEI (Polysciences Inc.). The cells were incubated for 72 hours and lysed using RIPA buffer and protease inhibitor cocktail. The cell lysates were run on Western blots and probed with HIS antibody (abm 1:1000) for 1 hr at RT. Odyssey goat anti mouse secondary antibody (1:4000; LI-COR) was used for 1 hr at RT. Coomassie staining was done to ascertain equal total protein loading for each condition.

Optic Nerve Crush.

All animals were female Sprague-Dawley rats weighing 250-300 g, which were kept in a pathogen free environment. Briefly, seven days before the nerve crush, animals received stereotaxic injections of 2% Fluorogold into the superior colliculus target of RGCs. A Foredoom Micro Motor drill attached to a stereotaxic arm was used to drill holes in the skull above the superior colliculus bilaterally. Injections were performed using a 10-µl Hamilton syringe actuated by a computer controlled Picopump (World Precision Instruments). Two injections, each consisting of 3 µl of Fluorogold solution, were delivered at different depths within the superior colliculus at an injection rate of 500 nl/min. The needle was left in place for 10 min after each injection and slowly withdrawn to prevent reflux of the injected solutions up the needle tract.

Additionally, for crushing nerve surgical procedures, animals were placed in a stereotaxic frame and ventilated with isoflurane (2%; 0.8 L/min O2) through a gas anesthesia mask. The nerve was accessed through an incision in the superior rim of the orbit, following retraction of the overlying rectus muscles. The optic nerve was crushed using fine self-closing forceps for 6 seconds. Eventually, the orbital contents were gently returned to their original location and the initial incision was closed. Following surgery, under a heat lamp, animal were maintained at 37° C. in the normothermic condition and they were given Ketoprofen (5 mg/mL, dosage for rats: 0.1 mL/100 g bodyweight) and sterile saline to ease postsurgical recovery.

Injection Protocol and Medications.

In order to evaluate the effects of 4Ig, N-Raft, and MβCD on RGC survival and regeneration after optic nerve crush, 4 µl intraocular injection of 4Ig (250 ng/µl) and N-Raft (150 ng/µl) solutions were delivered at 3 and 10 days after injury. Additionally, these two groups received 4Ig and N-Raft in a dose of 1 mg/kg, via intrajugular vein at 3 and 10 days postcrush. Separately, animals in MβCD group, received intraperitoneal injection of MβCD at 1000 mg/kg/week for 3 weeks after nerve crush on a once-a-day schedule.

Intraocular Injection.

Briefly, the rats were initially anesthetized with 2% isoflurane in a mix of $O_2$ and then the cornea was anesthetized using Alcaine eye drops (Alcon) prior to intraocular injections. A pulled glass micropipet attached to a 10 µl Hamilton syringe via a hydraulic coupling through PEEK tubing was used to deliver 4Ig, and N-Raft solution into the vitreous chamber of the eye, posterior to the limbus. The pipette was held in place for 5 s after injection and slowly withdrawn from the eye to prevent reflux. Following injection, the cornea was covered with ophthalmic ointment to prevent desiccation and animals were returned to their normal housing.

Quantification of RGC Survival after Injury.

Animals were euthanized at 21 days after nerve crush and the eyes were enucleated, the cornea and lens were removed, and the remaining eye cups containing the retinas were fixed in 4% paraformaldehyde for 1 hour. The retinas were then removed, flat-mounted, and coverslipped using 50:50 glycerol/PBS. Fluorogold staining in RGCs was visualized using an Andor iXon 885+ electron-multiplying charge-coupled device cameras attached to a Leica DM LFSA microscope. Moreover, Sutter Lambda XL (Quorum Technologies, Guelph, Canada) with a liquid light guide was used as a source of illumination. The densities of RGC were measured at the inner (⅙ retinal eccentricity), midperiphery (½ retinal eccentricity), or outer retina (⅚ retinal eccentricity) of each quadrant of the flat-mount (defined distances from the center of the retina). This cell count was divided by a factor of 0.08, to yield an extrapolated RGC density per unit area of cells/mm$^2$.

Quantification of RGC Regeneration, intraretinal integrity and GAP-43 Immunohistochemistry.

Firstly, RGC axon regeneration and intraretinal integrity was examined at twenty-one days after optic nerve crush. The anterograde labeling of RGCs occurred two days before removal of the nerve and fixation and the anterograde tracer FITC-conjugated cholera toxin type B (CTB-FITC) was injected into the vitreous chamber of the eye to trace axons actively. CTB-FITC was anterogradly transported within the axon to reach the synaptic membrane.

RGC axon regeneration was examined at twenty-one days after optic nerve crush. Animals were perfused with 4% paraformaldehyde via the ascending aorta, while the descending aorta was clamped off, and the optic nerves were removed. The nerves were post-fixed overnight in the same fixative solution, plus 30% sucrose in PBS for 7 days at 40 C. The fixed nerves were consecutively sectioned at 14 µm in thickness with a Leica CM1950 cryostat microtome. The slides were first incubated overnight at 4° C. in primary antisera directed against growth associated protein-43 (GAP-43), a marker of regenerating retinal ganglion cell axons in both neonatal and adult RGCs. Primary antisera (rabbit polyclonal, 1:250, Cell Signaling Technology/NEB) were diluted in PBS containing 0.3% Triton X-100 and 3% normal goat serum. Following primary antibody incubation, sections were rinsed three times for 15 minutes in PBS and followed by three hours incubation with FITC labeled secondary antibody at room temperature.

The slides were then rinsed three times for 15 minutes in PBS before cover slipping with 50:50 glycerol/PBS. The total number of regenerating axon growth cones within bins of the optic nerve, beginning anterior to the crush site and proceeding distally, were quantified. The bins were as follows: 0-250, 250-500, and >500 µm. A total of four equally spaced sections through the width of each optic nerve were examined and quantified using a Leica DM LFSA microscope (20× objective) with an Andor iXon 885+ camera, with EMgain applied.

Statistical Analysis.

Densities of RGCs and the number of regenerating axons were presented as mean±SEM and analyzed with one-way analysis of variance followed by the Tukey test. Densities of RGCs were grouped by retinal eccentricity (inner, middle, outer). Differences were considered significant when $p<0.05$.

Spinal Cord Injury.

Pre-operatively, 32 adult female Wistar rats (Charles River, St. Constant, QC, 200-300 g) were acclimatized and trained for baseline behavioral assessment. Rats were divided into 4 groups (n=8/group): 1) MBCD (i.p.); 2) vehicle control (i.p); 3) 4Ig (i.v. and intraspinal); 4) vehicle control (i.v. and intraspinal). Rats were anesthetized by inhalation of 2% isofluorane in combination with a mixture of nitrous oxide and oxygen (1:2, v/v). The spinal cord was exposed by laminectomy and a clip compression injury was made at spinal cord level T8 with a 20 g force. This was a clinically relevant model of SCI reflecting human pathology. n the 4Ig and equivalent control group, 4Ig or vehicle was injected intraspinally immediately following SCI. A total of 2 injections (250 ng/µL, 3 µL each) were made 1 mm rostral and 1 mm caudal to the lesion site and adjacent to the midline vein. Injections were made stereotactically with the aid of an operating microscope using a motorized microinjector at a rate of 1.5 µl/min with a 10 µl Hamilton syringe and a customized 32 G needle. The needle was left in place for an additional 2 min after injection to prevent leakage. The overlying muscle and skin were sutured with 3-0 vicryl sutures (Johnson and Johnson, Peterborough ON, Canada).

Immediately following SCI, the 4Ig treated rats also received a 1 mg/kg dose of 4Ig i.v. via the intrajugular vein and subsequent i.v. injections weekly for 2 more weeks. Rats in the MβCD group received intraperitoneal injection of MβCD at 1000 mg/kg/week immediately following SCI and then daily i.p. injections until sacrifice. Control rats received equivalent volumes as described above. Bladders were evacuated manually 3 times daily until spontaneous voiding was established, and hematuria or urinary tract infection was treated with Clavomax (62.5 mg PO BID for 7 days). The rats were housed singly in a temperature-controlled room at 26° C. with a 12 hour light/dark cycle. Water and food were provided ad libitum.

Intrathecal Infusion.

In a separate experiment to assess local delivery of 4Ig, 19 adult female Wistar rats were injured and injected rostral and caudal to the lesion site with 4Ig or phosphate-buffered saline (PBS) as described above. Immediately after the intraspinal injections, 4Ig was delivered intrathecally through a polyurethane catheter (Alzet Model No. 0007741; Alzet Osmotic Pumps, Cupertino, Calif.) attached to a mini-osmotic pump (Alzet Model No. 2002). 233 uL of 4Ig (1 ug/uL) was injected into the mini-osmotic pump. An equal volume of PBS was used as a control in animals not receiving 4Ig. The pump was primed in sterile saline at 37° C. overnight. A small midline durotomy was made at T9 through which the catheter was inserted into the intrathecal space. The tip of the catheter was directed rostrally to the T7 level, which was approximately 1 mm rostral to the site of the rostral injection of 4Ig. The catheter and pump were sutured extensively to the subcutaneous tissues. 4Ig or PBS was then intrathecally delivered continuously for 14 days (0.5 uL/hr) via the catheter and pump system.

Functional Analysis.

Functional tests were performed before the injury, 1 day, and then weekly for 6 weeks post-SCI. Locomotor function was evaluated using the BBB locomotor rating scale. Rats were placed individually in an open field with a non-slippery surface and 2 independent examiners, blinded to treatments, observed and video-recorded hindlimb movements for 4 min and assessed the animal's function including joint movements, stepping ability, coordination, paw placement, and toe clearance. A score of 0 indicates no hindlimb movement, a score of 21 indicates unimpaired locomotion as observed in Control. Motor subscores were determined to assess toe clearance, predominant paw position and absence of instability. A maximal motor subscore of 7 means normal locomotion.

Ladder-walk analysis with apparatus was done to assess fine motor functions. Rats were trained for a week pre-SCI to cross a horizontal ladder. At 1 week post-SCI and weekly thereafter, rats with a BBB score>10 were placed on the horizontal ladder-walk apparatus and 3 test runs were recorded. Recordings were analyzed in slow motion; the number of footfalls per hindlimb was recorded and the average was calculated for each rat per week. Injured rats with dragging hindlimbs were scored the maximum footfalls of 12. Uninjured rats had 0 or occasionally 1 footfall per crossing. The relative success rate on the test was calculated.

Tissue Preparation, Immunostaining, and Quantitative Analysis.

Rats were sacrificed at 6 weeks after SCI following weekly behavioural assessment. Rats were deeply anesthetized with intraperitoneal sodium pentobarbitol and transcardially perfused with 4% paraformaldehyde in 0.1 M phosphate buffered saline (PBS), pH 7.4. A 1.5 cm segment of tissue encompassing the lesion site at T8 was excised and cryoprotected in 30% sucrose in 0.1 M PBS for at least 24 hours. Tissue was embedded in Shandon Cryomatrix (VWR Laboratories, Mississauga, ON, Canada) and cryosectioned parasagittally into 20 μm serial sections.

To quantify spared host neurons, sections were immunoreacted with NeuN. Sections were blocked for 1 hr with 10% (v/v) normal goat serum in 0.1 M PBS, incubated overnight with mouse anti-NeuN (1:500; Chemicon) for neurons, washed in PBS, incubated for 1 hr with biotinylated anti-mouse secondary antibody (Vector Laboratories), washed and incubated with avidin-biotin-peroxidase complex (Vectastain Elite ABC Kit Standard, Vector Laboratories) for 1 hour. Diaminobenzidine (DAB) (Vectastain Elite ABC Kit Standard, Vector Laboratories) was applied as the chromogen. For each cord, 5 sections 280 to 420 um apart at equivalent anterior-posterior distance, through the thickness of the cord was sampled to include equivalent gray matter regions and to avoid double-counting of cells. All NeuN positive neurons were counted 2.7 mm rostral and caudal from the lesion epicentre using Nikon NIS Elements BR v.3.1 software. Data were presented as group means of total counts that have not been normalized for the entire cord thickness.

To quantify host astrocytes and oligodendrocytes, sections were blocked as above and incubated with the following primary antibodies overnight: mouse anti-GFAP (1:200; Chemicon, Temecula, Calif.) for astrocytes and mouse anti-CC1/APC (1:1000; Calbiochem, San Diego, Calif.) for oligodendrocytes. Tissue sections were washed with 0.1M PBS and incubated with fluorescent-conjugated secondary antibodies for 1 hr at room temperature, washed with PBS and then coverslipped with Vectashield mounting medium containing 4',6-diamidino-2-phenyl-indole (DAPI) (Vector Laboratories, Burlington, ON, Canada) nuclear counterstain. Species-specific non-immune IgG and omission of primary antibody was used as negative controls. To quantify survival of host oligodendrocytes adjacent to the site of injury, sections immunostained with CC1 were imaged with identical settings and exposure times using a Nikon Eclipse TE 300 microscope and NIS Elements BR v.3.1 software. Three sections with maximal cavitation and similar dorsal-ventral distance were examined per animal. The number of CC1+ cells in a field (2.9×105 um2 area) were counted both rostral and caudal within 600 um from the edge of the lesion in each section. To quantify GFAP immunoreactivity, immunostained sections were imaged with identical settings and exposure times using a Nikon Eclipse TE 300 microscope and NIS Elements BR v.3.1 software. Three sections with maximal cavitation and similar dorsal-ventral distance were examined per rat. For each section, the sum intensity values of three regions ($1.1 \times 10^6$ $um^2$ area) were determined at 0.45 mm and 1.8 mm from the edge of the lesion both rostrally and caudally. For each region, mean intensity values were averaged per group.

To quantify lesion volume, every eighth parasagittal section was processed for luxol fast blue and hemotoxylin & eosin (LFB/H&E) for tissue morphology. The sections were imaged with a Nikon Eclipse TE 300 microscope and the area of cavitation of each section was traced using Nikon NIS Elements v.3.1 software. Any necrotic tissue within the cavities was counted as part of the lesion. The total cavity volume was calculated by summation of the measured area of each section multiplied by the inter-section distance.

Anterograde Axonal Tracing of the Corticospinal Tract (CST) with Biotin Dextran Amine (BDA).

To visualize axons from the CST, anterograde axonal tracing with BDA was performed 6 weeks after SCI following completion of the functional assessment. Animals (n=3-4) from each group were randomly selected for BDA injection. Under deep anesthesia with 2% isofluorane with 1:2 NO:O2, rats were positioned in a stereotaxic frame and craniotomy was performed bilaterally to expose the sensorimotor cortex. BDA (10%, 10,000 MW; Invitrogen (Life Technologies)) was dissolved in 0.01M PBS and injected at 6 sites in each sensorimotor cortex using the following coordinates in reference to bregma: 1) 0.5 mm posterior and 1 mm lateral, 2) 0.5 mm posterior and 2 mm lateral, 3) 1 mm posterior and 1 mm lateral, 4) 1 mm posterior and 2 mm lateral, 5) 1.5 mm posterior and 1 mm lateral, 6) 1.5 mm posterior and 2 mm lateral. At each site, 1 μl of BDA was injected 1.2 mm from the surface of the cortex. Injections were made stereotactically with the aid of an operating microscope using a motorized microinjector at a rate of 0.5 μl/min with a 10 μl Hamilton syringe and a 32-gauge needle. The needle was left in place for an additional 2 min after injection to prevent leakage and the skin was closed with 6-0 Vicryl. Animals were allowed to survive for 3 more weeks and then intracardially perfused with 4% paraformaldehyde in 0.1 M PBS. BDA tissue including a 1.5 cm segment of tissue encompassing the lesion site was excised and processed as either 20 μm cryosections on slides or free-floating 30 μm sections. Free-floating sections were collected in 24-well plates containing PBS. Sections were pre-treated with 1% H2O2 in methanol for 10 min at RT, rinsed with PBS containing 0.5% Triton X for 30 min, and incubated in avidin-biotin peroxidase complex (Vectostain Elite ABC Kit Standard, Vector Laboratories, Burlington, ON, Canada) for 1 h at RT. Slides were washed with PBS, and then incubated with fluorescent Alexa-488 goat anti-mouse secondary antibody (1:500; Invitrogen (Life Technologies)) for 1 h at RT and coverslipped with Vectashield mounting medium containing DAPI (4', 6-diamidino-2-phenyl-indole) (Vector Laboratories, Burlington, Ontario, Canada) nuclear counterstain.

Statistical Analysis.

Functional tests were analyzed by two-way repeated-measures ANOVA comparing groups versus time points followed by post-hoc pairwise multiple comparisons using the Bonferroni method. Differences in cell counts were analyzed using one-way ANOVA, followed by pairwise multiple comparisons using the Bonferroni test. Data are presented as mean±standard error. Differences were considered significant when $p<0.05$.

Caspase-3 and NeuN Staining of Spinal Cord Sections.

A 1.5 cm segment of tissue from control (n=4) and 4Ig (n=4) treated rats encompassing the lesion site at T8 was excised and cryoprotected in 30% sucrose. Tissue was sectioned parasagittally into 20 μm serial sections. To co-label spared Neurons with caspase-3, sections were blocked and incubated overnight with rabbit anti caspase-3 (1:750; Cell Signaling) at 4° C. Next day, sections were washed and incubated with mouse anti-NeuN (1:500; Chemicon) for 4 hrs at RT, followed by Alexa 488 anti-mouse and Alexa 555 anti-rabbit secondary antibodies (1:500; Molecular Probes) along with DAPI/PBS for 1 hr at RT. For each cord, 5 sections 160 um apart, through the thickness of the cord were sampled to avoid double-counting of cells. All NeuN positive neurons and NeuN/Caspase-3 double labeled cells, as well as the total number of caspase-3 labeled cells and DAPI stained cells were counted 1.5 mm rostral and caudal from the lesion epicenter using cellSens software (Olympus).

Example 2

Presence of Neogenin in the Lipid Rafts of Growth Cones

To study the role of Neogenin in the developing central nervous system (CNS), the expression of Neogenin in brain membranes (E8) was examined by Western blotting. The following antibodies were used in this study: AF1079, which is an antibody directed against the entire extracellular domain of Neogenin, and N-20, which is an antibody directed against the N-terminus of Neogenin. AF1079 detected two bands at 180-kDA and 150-kDa while N-20 detected a band at 180-kDa (FIGS. 1A and 1B). This result indicated that brain membranes contained full-length Neogenin (i.e., 180-kDa) and a N-terminal truncation of Neogenin (i.e., 150-kDa), which lacked some of the 4Ig repeats.

To further study the expression of Neogenin, the membrane localization of Neogenin was examined by confocal imaging. Specifically, staining was performed with an antibody against the N-terminal part of Neogenin. This staining exhibited a punctate staining pattern in the growth cone of retinal ganglion cells (RGCs, E8, FIGS. 1A-1D). These punctate structures co-localized with the raft markers, cholera toxin (CTB) and RGMa (FIGS. 1E and 1F), with computed intensity correlation quotients of 0.27 and 0.32, respectively. This result indicated that Neogenin significantly associated with RGMa (P sign=0.005) and lipid rafts (P sign=0.0002). As a control, axons were stained for CTB and F-action. In this control experiment, the computed correlation quotient was 0.05, which indicated segregation of the staining for CTB and F-action (FIG. 8).

To further examine the localization of Neogenin in lipid rafts, the abundance of Neogenin in isolated lipid rafts from chick brain membrane was examined. Neogenin was recovered in fractions 2-4, which are enriched in the lipid raft markers Flotillin and RGMa (FIG. 1G). Neogenin was not recovered in the non-lipid raft fractions, which contained the heavy fraction marker transferrin receptor (FIG. 1G).

Additionally, embryos were treated with methyl-β-cyclodextrin (MβCD) to deplete membrane cholesterol, which disrupted the lipid rafts, and the brain samples were fractionated. In the presence of MβCD, Neogenin was recovered in the non-lipid raft fraction along with the transferrin receptor (FIG. 8C).

In summary, the above results demonstrated that Neogenin was localized in brain membranes in the developing CNS, and more specifically, that Neogenin was localized in the lipid rafts within these brain membranes.

Example 3

The Presence of Neogenin in Lipid Rafts was Regulated by an Interaction Between N-Raft and Neogenin-4Ig As described above, Neogenin was associated with lipid rafts and RGMa. To determine if an interaction between Neogenin and RGMa was involved in the recruitment of Neogenin to lipid rafts, binding studies were performed to examine the interactions between different regions of Neogenin and RGMa.

Specifically, the 4Ig-domain and 6FNIII-domain of Neogenin were each fused to alkaline phosphatase (AP). The 4Ig-domain and 6FNIII-domain of Neogenin were found in the extracellular portion of Neogenin. Accession No. AAC59662 (SEQ ID NO:1) was the amino acid sequence of Neogenin. The 4Ig-domain was amino acids 1 to 383 of Accession No. AAC59662 (SEQ ID NO:1). The 6FNIII-domain was amino acids 429 to 1036 of Accession No. AAC59662 (SEQ ID NO:1).

Figure 2:
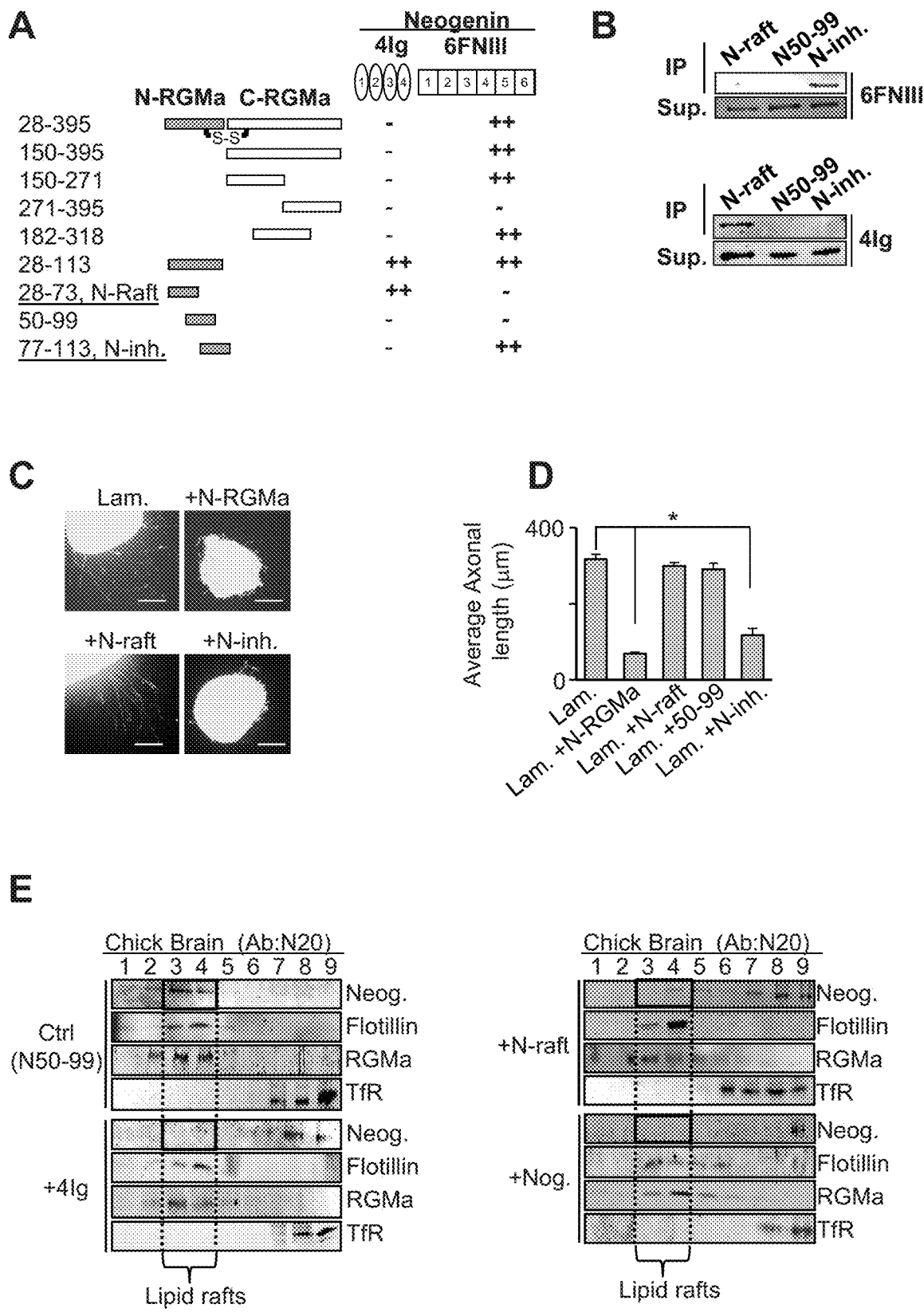
FIG. 2 shows the cis-interaction between the 4Ig domain in Neogenin and the N-terminal part of RGMa recruited Neogenin to lipid rafts. (A) RGMa proteins were incubated on plates coated with 4Ig- or 6FNIII-AP. (Binding: −, base line; ++>5×base line; quantitative analysis for this experiment is presented in FIG. 9). One C- and one N-RGMa domain (N-RGMa$^{77-113}$) interacted with 6FNIII. One N-RGMa domain (N-Raft) interacted with 4Ig. (B) Supernatants (Sup) from cells expressing His-6FNIII or His-4Ig, were pulled down (IP) with beads coated with N-Raft, N-RGMa$^{50-99}$, and N-inh. Western Blot was then performed with an anti-His antibody to reveal whether or not His-6FNIII or His-4Ig interacted with the coated beads. This showed that His-6FNIII was pulled down by N-inh whereas His-4Ig was pulled down by N-Raft. Western Blot on cell supernatants was performed to demonstrate that the same amount of His-FNIII and His-4Ig were used to perform the pull down. (C) Images and (D) Quantification of retinal-explant outgrowth on laminin (lam.) and laminin plus N-RGMa or N-RGMa protein domains showed that only N-RGMa and N-in. inhibited axonal growth. Data are average±SEM (n=3 independent experiments), *p<0.0001. Scale bar, 100 μm. (E) Chick brains were injected with control peptide (Ctrl; N-RGMa$^{50-99}$), 4Ig, N-Raft, or Noggin 1 day before preparing membrane fractionations. In control experiments, Neogenin localized to the Flotillin/RGMa-containing lipid raft fraction (as shown in solid lined boxes). 4Ig, N-Raft, or Noggin shifted Neogenin to heavy fractions.

The binding of these fusions to various RGMa peptides were analyzed in an ELISA assay (FIG. 2A). The 6FNIII-domain of Neogenin interacted with full-length RGMa, but the 4Ig-domain of Neogenin did not interact with full-length RGMa (FIG. 2A). This data suggested that the in vivo binding of RGMa and Neogenin may require an additional factor(s) to facilitate a cis interaction between RGMa and Neogenin, which is described below in more detail.

Additionally, the 4Ig-domain of Neogenin interacted with the N-terminal part of RGMa (FIG. 2A). The 6FNIII-domain of Neogenin (also referred to herein as the "fibronectin domain") also interacted with the N-terminal part of RGMa.

Figure 9:
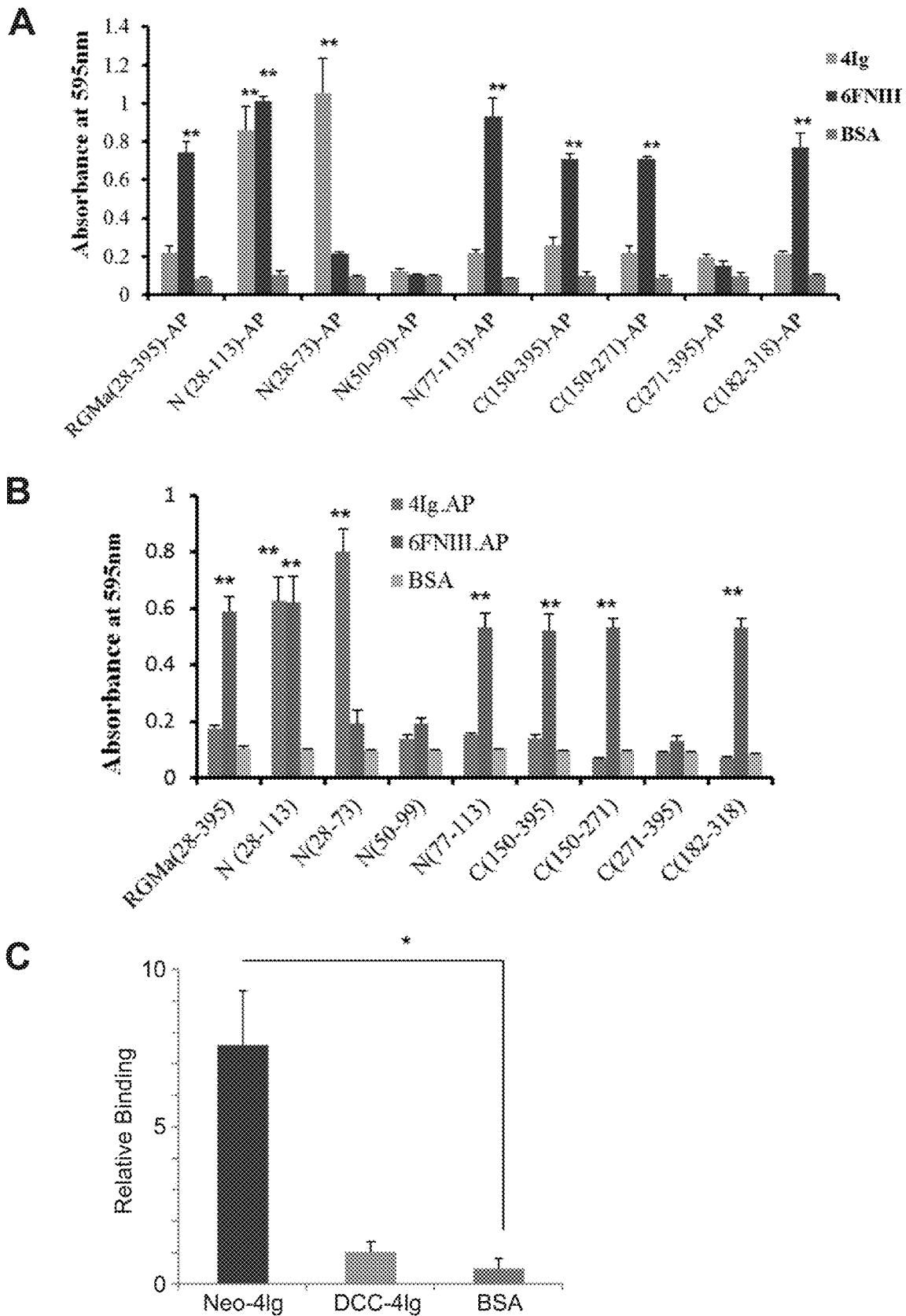
FIG. 9 shows identification of different RGMa domains that interact with separate Neogenin regions. (A) Different RGMa-AP proteins were incubated on wells coated with the 4Ig 6FNIII or BSA. Binding was revealed by adding a colorimetric substrate p-Nitrophenyl Phosphate, which revealed presence of the AP tag, and the absorbance at 405 nm was measured using a plate reader. Data were average±SEM (n=3 independent experiments), *p<0.005. (B) Quantification of a binding assay where 4Ig-AP and 6FNIII-AP proteins were assayed on wells coated with proteins from different RGMa regions. The fragments that showed interaction in (a) where confirmed in this assay. Thus, two N-RGMa fragments were identified (N-Raft and N-RGMa77-113) that bound the 4Ig and 6FNIII domains in Neogenin, respectively. C-RGMa proteins and full length RGMa only bound 6FNIII. Data were average±SEM (n=3 independent experiments), *p<0.005. (C) The 4Ig domain of DCC does not interact with N-Raft (N-RGMa28-73). Quantification of a binding assay where N-RGMa-AP was assayed on wells coated with proteins DCC-4Ig and Neogenin-4Ig. In this experiment Neogenin-4Ig but not DCC-4Ig interacted with N-Raft-AP. Data were average±SEM (n=4 independent experiments), *p<0.005. (D) Cis-interaction between the 4Ig domain of Neogenin and N-Raft is required for localization of Neogenin in lipid rafts. HEK-293 cells were transfected with Neogenin and RGMa constructs. BMP2 (100 nM) was added to the medium 1 hour before cells were collected. Western blotting was performed following lipid raft fractionation. Flotillin was used as a marker for lipid raft fractions, whereas the transferrin receptor (TfR) was used as a marker for heavy membrane-fractions. Every experiment was repeated twice. Western Blots for Neogenin were done with the antibody AF 1079, which recognizes both isoforms. In the first set of experiments, cells were only transfected with Neogenin. In cell membranes from that study, Neogenin co-localized with the marker for heavy membranes TfR and no co-localization with the lipid raft marker flotillin was observed. In the second set, full length Neogenin and RGMa were transfected and the 180 kDa Neogenin band localized to the lipid raft fractions that contain flotillin. In the third and fourth set, when either 4Ig truncation of Neogenin (Neo (4Ig del)) or a N-RGMa28-73 (N-Raft) truncation of RGMa (RGMa (28-73 del)) were transfected, Neogenin was no longer present in flotillin containing raft fractions. This suggests that an interaction between 4Ig and N-RGMa28-73 (N-Raft) is required for Neogenin presence in lipid rafts.
Figure 9:
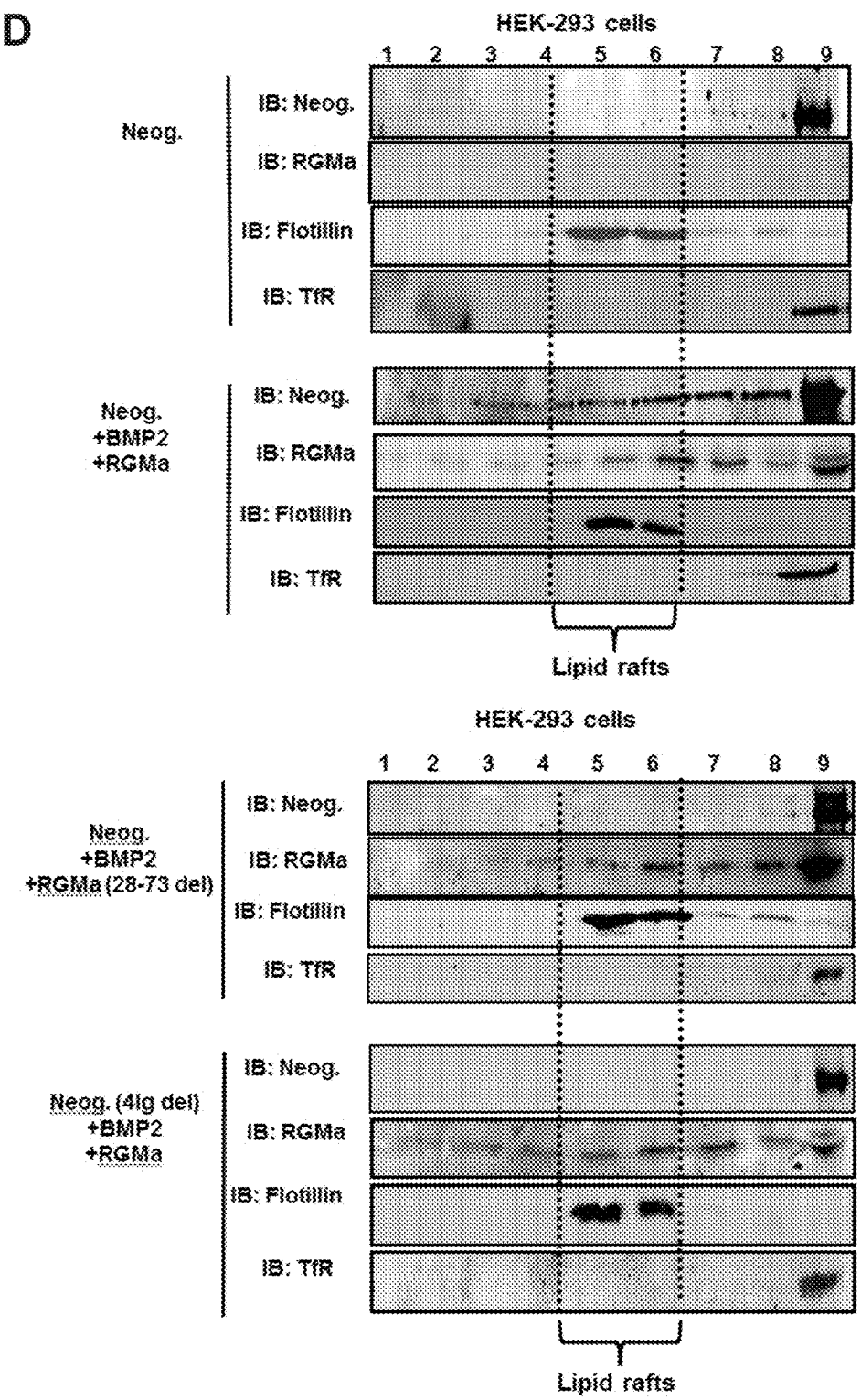

To determine if distinct N-terminal regions of RGMa bound the 4Ig- and 6FNIII-domains of Neogenin, peptides were generated that spanned the N-terminal region of RGMa. The amino acid sequence of RGMa was Accession No. NP_989868.1 (SEQ ID NO:6). These peptides were a peptide spanning amino acids 28-73 of RGMa (also referred to herein as "N-Raft") and a peptide spanning amino acids 77-113 of RGMa (also referred to herein as "N-inh"). The N-Raft peptide interacted with 4Ig-domain of Neogenin, but not the 6FNIII-domain of Neognin. The N-inh peptide interacted with the 6FNIII-domain of Neogenin, but not the 4Ig-domain of Neogenin. In a complementary experiment, in which the N-Raft and N-inh peptides of RGMa were fused with AP instead of the 4Ig- and 6FNIII-domains of Neogenin, N-Raft bound to the 4Ig-domain and not the 6FNIII-domain while N-inh bound to the 6FNIII-domain and not the 4Ig-domain (FIG. 9). Additionally, N-inh and N-Raft coated beads pulled down 6FNIII-domain and 4Ig-domain, respectively, which was consistent with the ELISA results described above (FIG. 2B).

To assess the specificity of the interaction between the 4Ig-domain of Neogenin and N-Raft, the closest Neogenin homologue DCC was examined to determine if DCC interacted with N-Raft. No significant interaction between the 4Ig-domain of DCC and N-Raft was observed (FIG. 9C).

To determine if the above described Neogenin-RGMa interactions were biologically relevant, outgrowth experiments using the RGMa peptides as substrates were performed (FIG. 2C). The full-length N-RGMa and the N-inh fragments caused a 3-4 fold decrease in axonal growth compared to controls (51.5±3.0 µm and 88.1±13.3 µm vs. 238.1±9.3 µm; FIGS. 2C and 2D). These data indicated that the interaction of N-RGMa and N-inh with the 6FNIII-domain of Neogenin inhibited retinal axon growth. When the N-Raft peptide was used as a substrate, no effect on axonal outgrowth was observed (FIG. 2C-D). These data indicated that the interaction between N-Raft of RGMa and the 4Ig-domain of Neogenin did not inhibit axonal outgrowth in trans. Accordingly, to inhibit axonal outgrowth in trans, RGMa interacted with the 6FNIII-domain of Neogenin and not the 4Ig-domain of Neogenin.

To assess whether the N-Raft and 4Ig interaction recruited Neogenin into lipid rafts, the N-Raft and 4Ig domains were deleted from RGMa and Neogenin, respectively, and Neogenin association with lipid rafts was then examined (FIG. 9). Specifically, HEK293 cells were co-transfected with Neogenin and RGMa and treated with BMP2. BMP2 promoted Neogenin recruitment to lipid rafts. In these HEK293 cells, Neogenin was found in the lipid raft fraction.

In contrast, the deletion mutants of Neogenin (i.e., deletion of 4Ig-domain and referred to herein as "4Ig-del") and RGMa (i.e., deletion of the N-Raft domain and referred to herein as "N-Raft-del") were normally targeted towards the cell surface (data not shown), but neither deletion mutant was recruited to the lipid raft fractions (FIG. 9). These data indicated that the interaction between N-Raft and 4Ig was needed for Neogenin to be present in lipid rafts.

As such, it was examined if overexpressing recombinant 4Ig and N-Raft competed with the endogenous 4Ig and N-Raft domains to displace Neogenin from the lipid raft fractions to the non-lipid raft fractions. Specifically, N-Raft, 4Ig-domain, or a control peptide, which was amino acid residues 50-99 of RGMa (also referred to herein as "N-RGMa$^{50-99}$"), was injected into the optic tectum at E8. The tecta were collected a day later for fractionation-analyses.

Full-length Neogenin localized exclusively to the raft fraction in the control (N-RGMa$^{50-99}$). In the presence of N-Raft or 4Ig, Neogenin was relocalized from the lipid raft fractions to the heavy fractions, which did not contain lipid raft proteins (FIG. 2E).

The presence of Neogenin in lipid rafts is also dependent on BMP. Accordingly, it was examined if in the presence of the BMP-chelator Noggin, Neogenin was relocalized from the lipid raft fractions to the heavy fractions. Specifically, for this study, Noggin was injected into chick brains and it was observed that in the presence of Noggin, Neogenin was not present in the lipid rafts (FIG. 2E). Accordingly, the above data indicated that Noggin, N-Raft, and 4Ig each prevented Neogenin associated with lipid rafts.

In summary, the above in vitro and in vivo results indicated that an interaction between the 4Ig-domain in Neogenin and the N-Raft-domain in RGMa was needed to recruit Neogenin to lipid rafts.

Example 4

Knock Down Analysis Revealed a Cis Interaction Between RGMa and Neogenin

The CNS contains three RGMa isoforms, namely N-RGMa, C-RGMa, and RGMaΔ. N-RGMa and C-RGMa were as shown in FIG. 2A. RGMaΔ was full-length RGMa.

N-RGMa, C-RGMa, and RGMaΔ each inhibited axonal outgrowth in trans, and thus, when provided as a growth substrate, each of N-RGMa, C-RGMa, and RGMaΔ blocked axon growth. Additionally, each of N-RGMa, C-RGMa, and RGMaΔ blocked axon growth in trans by interacting with the fibronectrin domain of Neogenin (FIGS. 2A-2D).

As described above and shown in FIGS. 2E and 9, the interaction between the 4Ig-domain of Neogenin and N-RGMa$^{23-73}$ recruited Neogenin into lipid rafts. RGMa was localized to lipid rafts through its GPI anchor. Additionally, as also described above, Neogenin and RGMa were co-localized in the growth cone (FIG. 1F) and when N-Raft was provided as a growth substrate (i.e., in trans), N-Raft did not block axonal outgrowth (FIG. 2D). Together, these results indicated that Neogenin was recruited to lipid rafts via cis interaction with RGMa.

To further determine that a cis interaction between RGMa and Neogenin recruited Neogenin into lipid rafts, short hairpin RNAs (shRNAs) were employed to silence RGMa in the growth cone. Specifically, shRNA was delivered into the E2 chick eye and outgrowth on each of the RGMa proteins (i.e., N-RGMa, C-RGMa, and RGMaΔ) was measured using explants from transfected E7 retinas. Transduction of shRNA in the eye only disrupted the cis RGMa interaction with Neogenin in retinal ganglion cells (RGCs) and did not affect trans interactions between the growth cone and RGMa that was provided exogenously as the growth substrate.

Figure 3:
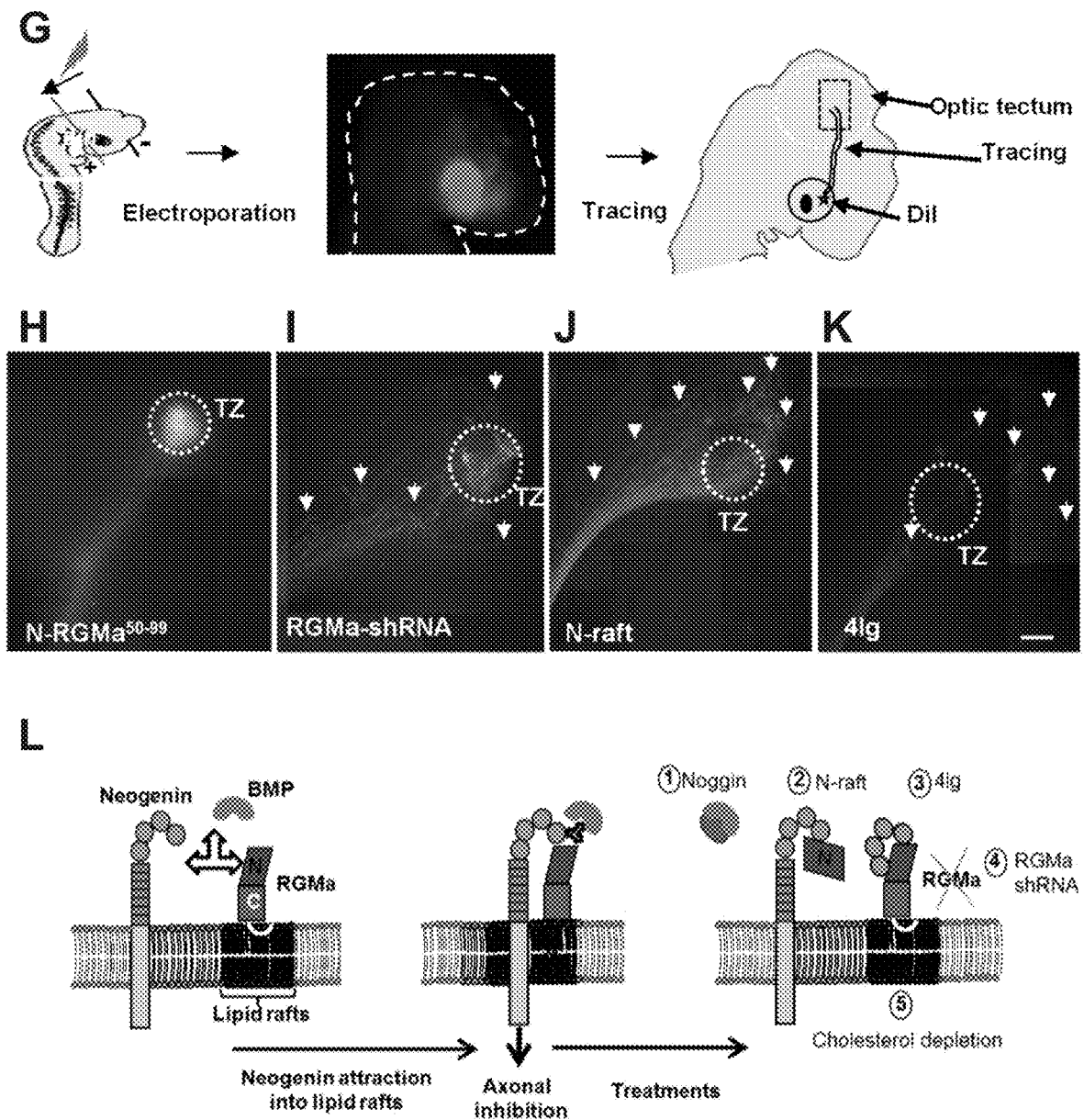
FIG. 3 shows that Neogenin association with lipid rafts was required for RGMa inhibitions. (A) Temporal explants cultured on N-RGMa and treated with 4Ig (1 μg/ml), N-Raft (1 μg/ml), RGMa ShRNAs (shRNA21 and shRNA37), MβCD (10 mM), CO (2 U/ml), and Noggin (100 nM). (B-F) Explants were grown on laminin (Ctrl), on laminin plus—N-RGMa, -C-RGMa, or -RGMaΔ and treated with (B) RGMa shRNA21 and shRNA37, (C) 4Ig, (D) N-Raft, (E) MβCD and CO, and (F) Noggin (Nog.). Data were average±SEM (n=3 independent experiments), *p<0.005. (G) Schematic representation of in vivo experiments in the chick visual pathway. The right eye was electroporated at E2 with plasmid expressing RGMa/Neogenin constructs and at E17 tracing was performed from the eye to the optic tectum. The inset denotes the area presented in panels h-k. (H) Control experiments using N-RGMa50-99, which does not interact with Neogenin. Axonal path was intact and all fibers established terminal arbors into the terminal zone (TZ). Electroporation of (I) RGMa-shRNA, (J) N-Raft or (K) 4Ig, perturbed axonal paths with numerous fibers establishing terminal arbors outside the predicted TZ (arrowheads). Scale Bar, 100 μm. (L) Schematic representation of the action of treatments presented above. The 4Ig domain in Neogenin interacted with the N-terminal part in RGMa (N-Raft) to allow a BMP-dependent recruitment of Neogenin into lipid rafts. Once in lipid rafts, Neogenin transduced axonal inhibition. Treatments that prevented Neogenin association with lipid rafts abolished axonal inhibition. These treatments were (1) Chelating of BMPs with Noggin; (2) Masking of the 4Ig site on Neogenin with the addition of N-Raft peptides; (3) Masking of the N-Raft site on RGMa with the addition of 4Ig peptides; (4) Silencing of RGMa with shRNAs (shRNA21 and ShRNA37), and (5) Disrupting lipid rafts using cholesterol depletion (MβCD and CO).

Two different shRNAs that suppressed endogenous RGMa (shRNA-21 and shRNA-37; FIG. 12) enhanced retinal explant outgrowth on N-RGMa substrate by 3.1- and 2.8-times, respectively, relative to control shRNA (FIGS. 3A and 3B). Additionally, silencing of RGMa provided a 2.8-3.4 fold increase in axonal growth on C-RGMa and RGMaΔ (FIGS. 3A and 3B).

In rescue experiments, co-transfection with mouse RGMa, which was resistant to shRNA37, restored the inhibitory activity of RGMa proteins in dissociated RGCs treated with shRNA37 (FIG. 10). Therefore, the result obtained with RGMa shRNA was not an off-target effect. Together, the above data indicated that in addition to the trans interaction, a cis interaction between RGMa and Neogenin, which recruited Neogenin to lipid rafts, was required to inhibit axonal outgrowth.

To further determine that the cis interaction between RGMa and Neogenin occurred between 4Ig and N-Raft, studies were performed to examine if 4Ig and/or N-Raft acted as blocking peptides and restored axonal growth in retinal explants grown on RGMa proteins. In these studies, the addition of 5 µg/ml of either 4Ig (FIGS. 3A and 3C) or N-Raft (FIGS. 3A and 3D) to the medium blocked the inhibitory effects of RGMa proteins and restored outgrowth. Together these data indicated that a cis interaction between the 4Ig-domain of Neogenin and N-Raft was required to inhibit axonal growth.

Example 5

RGMa Inhibition Required Neogenin Association with Lipid Rafts and BMPs

As described above, the interaction between 4Ig and N-Raft regulated Neogenin association with lipid rafts (FIG. 2E) and indicated that Neogenin must be present in lipid rafts to inhibit axonal growth. To further study whether Neogenin must be present in lipid rafts to inhibit axonal growth, the agents methyl-β-cyclodextrin (MβCD) and cholesterol oxidase (CO) were used to disrupt lipid rafts when axons were cultured on RGMa proteins. Specifically, when axons were cultured on RGMa proteins in the presence of 10 mM MβCD or 2 U/ml of CO, axonal outgrowth was restored to control values (FIGS. 3A, 3E, S3D). These data indicated that the axonal response to RGMa, which was provided in trans, was triggered by Neogenin transit to lipid rafts. This Neogenin transit to lipid rafts was mediated by the cis interaction between Neogenin and RGMa (i.e., the 4Ig-domain of Neogenin and N-Raft of RGMa).

The data in FIG. 2E indicated that in the developing CNS, Neogenin recruitment into lipid rafts was dependent on BMPs. To determine if Noggin, a protein that interacts with BMPs, affects the axonal response to RGMa proteins, axonal outgrowth was measured in the presence and absence of Noggin. In these studies, axonal outgrowth was unaffected by Noggin alone, but was markedly reduced by N-RGMa, C-RGMa or RGMaΔ (FIGS. 3A and 3F). Noggin restored outgrowth in retinal explants (E8) exposed to each individual RGMa to control values (FIGS. 3A and 3F). These data indicated that a similar mechanism, which was dependent on BMP, underlied the Neogenin-mediated response to all 3 RMGa proteins, i.e., N-RGMa, C-RGMa or RGMaΔ.

In summary, the above results indicated that RGMa, together with BMP(s), regulated Neogenin transport into lipid rafts and this transport was required to mediate axon growth inhibition by RGMa.

Example 6

Neogenin Required Lipid Rafts for Correct Axonal Pathfinding

To study the effect of the interaction between 4Ig and N-Raft on axonal paths in vivo, 4Ig, N-Raft, and the control NRGMa$^{50\text{-}99}$ were ectopically expressed and axonal pathfinding was examined. To ensure that the treatments affected growing axons and not their environment, when electroporation was performed, the application of the electric field was narrowed to the optic vesicle at E2, thereby restricting expression to the eye and retinal axons (FIG. 3G).

In the control experiments, all retinal axons established arborization within a well-defined terminal zone (FIG. 3H). As a positive control, an shRNA that silences RGMa and thus, perturbs axonal paths was electoporated, (FIG. 3I). 100% (8 of 8) of the 4Ig and 85.7% (6 of 7) of the N-Raft electroporations caused aberrant paths (FIGS. 3J and 3K).

Accordingly, these data that the interaction between 4Ig and N-Raft, which was required for Neogenin localization to lipid rafts, was also required for axonal pathfinding in vivo. Together, with the outgrowth experiments (FIGS. 3A-3F), these data indicated that RGMa binding in cis to Neogenin, aided by BMP, translocated Neogenin to lipid rafts, and this translocation was required for the subsequent trans RGMa-Neogenin interaction that inhibited axonal growth (FIG. 3L). In view of the foregoing, blocking translocation of Neogenin to lipid rafts with Noggin, N-Raft, 4Ig, or RGMa-knockdown in the growth cone or cholesterol depletion provided five strategies to stimulate axonal growth (FIG. 3L).

Example 7

Neogenin Required Lipid Rafts to Induce Cell Death

Neutralizing RGMa to inhibit the trans interaction increases axonal growth, but this, in turn, activates the pro-death function of Neogenin. To determine if Neogenin required lipid rafts to induce apoptosis, HEK293 cells were transfected with Neogenin and cell death was measured by trypan blue exclusion assay. In this assay, the HEK293 cells stably expressed RGMa (FIG. 11).

Figure 4:
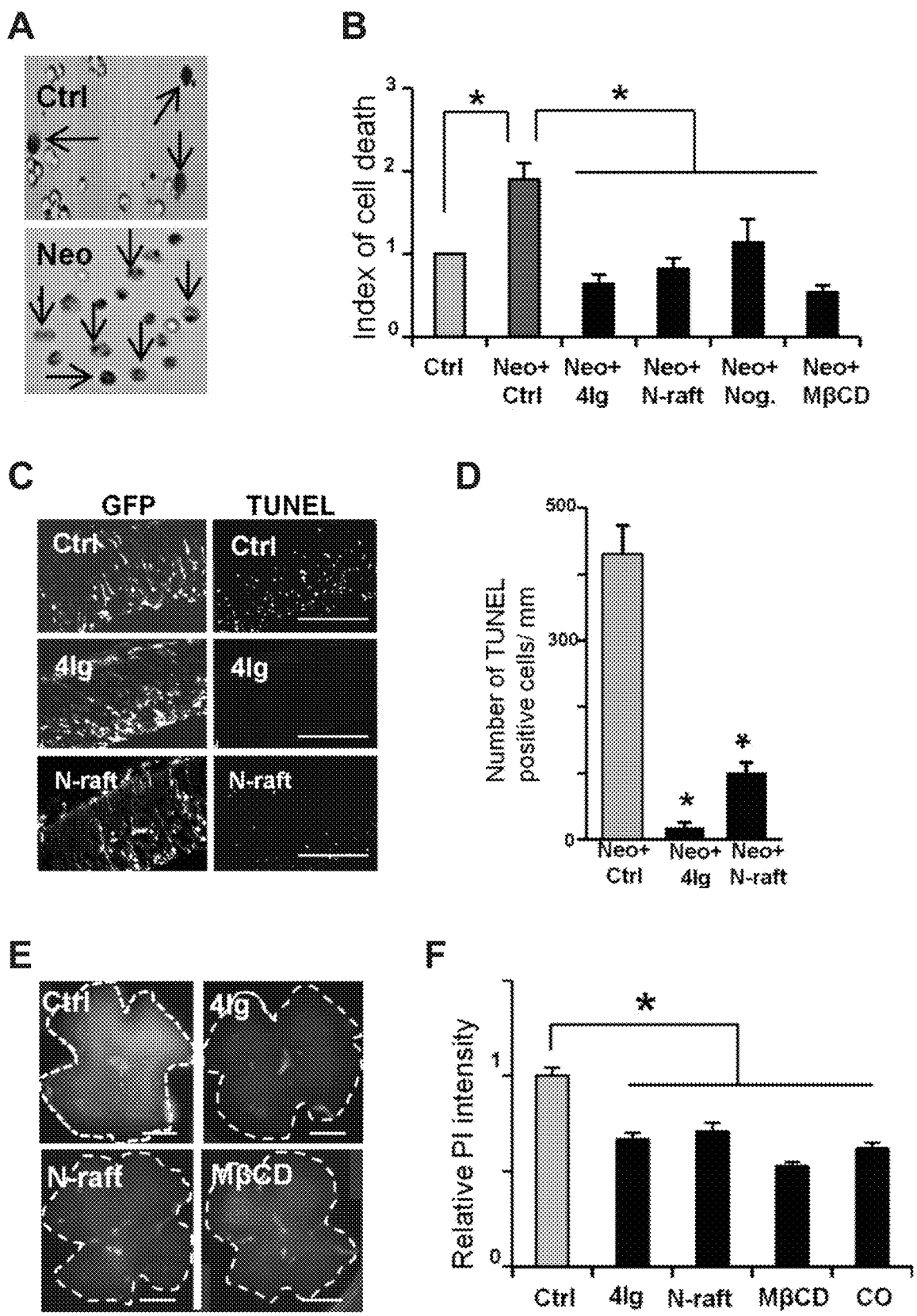
FIG. 4 shows that Neogenin required lipid rafts to induce cell death. (A) HEK293 cells that stably express RGMa (FIG. 11) were transfected with empty plasmid (Ctrl) or Neogenin (Neo). Neogenin induced cell death (arrows) when compared to control. (B) Quantification of cell death in Neogenin-transfected cells that were incubated in BSA (Neo+Ctrl), 4Ig (1 μg/ml), N-Raft (1 μg/ml), Noggin (100 nM), or MβCD (10 mM). Treatments that prevented Neogenin association with lipid rafts significantly rescued Neogenin-induced cell death. Data were average±SEM (n=3 independent experiments), *p<0.0001. (C) Representative images and (D) Quantification of cell death in chick E5 tecta electroporated with GFP- and a Neogenin-expression plasmid and then injected with N-RGMa50-99 (Ctrl; 1 μg/ml), 4Ig (1 μg/ml), or N-Raft (1 μg/ml) and subjected to TUNEL assay. 4Ig or N-Raft significantly reduced the number of TUNEL positive cells caused by Neogenin. Data were an average±SEM from 3 different tecta/conditions (*p<0.001). Bar, 100 μm. (E) Representative images and (F) Quantification of retinal whole mounts incubated for 4 days with control peptide (1 μg/ml), 4Ig (1 μg/ml), N-Raft (1 μg/ml), or MβCD (10 mM) and dead cells were stained with Propidium Iodide (PI). Images from 9 whole mounts per condition from 3 independent experiments were taken at the same intensities and the fluorescence measured using ImageJ. 4Ig, N-Raft, or MβCD significantly reduced cell death in retinal whole mounts. Bar, 500 μm. (G) Fluorescence micrographs of flat-mounted retinas depicting Fluorogold-labeled retinal ganglion cells (RGCs) in injured retinas at 14 days following axotomy. Control retinas (Ctrl) had few surviving RGCs. 4Ig, N-raft or MβCD increased cell survival. Bar, 200 μm. (H) Representations of the retinal areas selected in our analyses. Quantification of the density of surviving RGCs at 14 days post-axotomy showing (I) 4Ig or N-raft and (j) MβCD significantly increased RGC survival. Data were average±SEM (n=6 eyes), *p<0.01.
Figure 4:
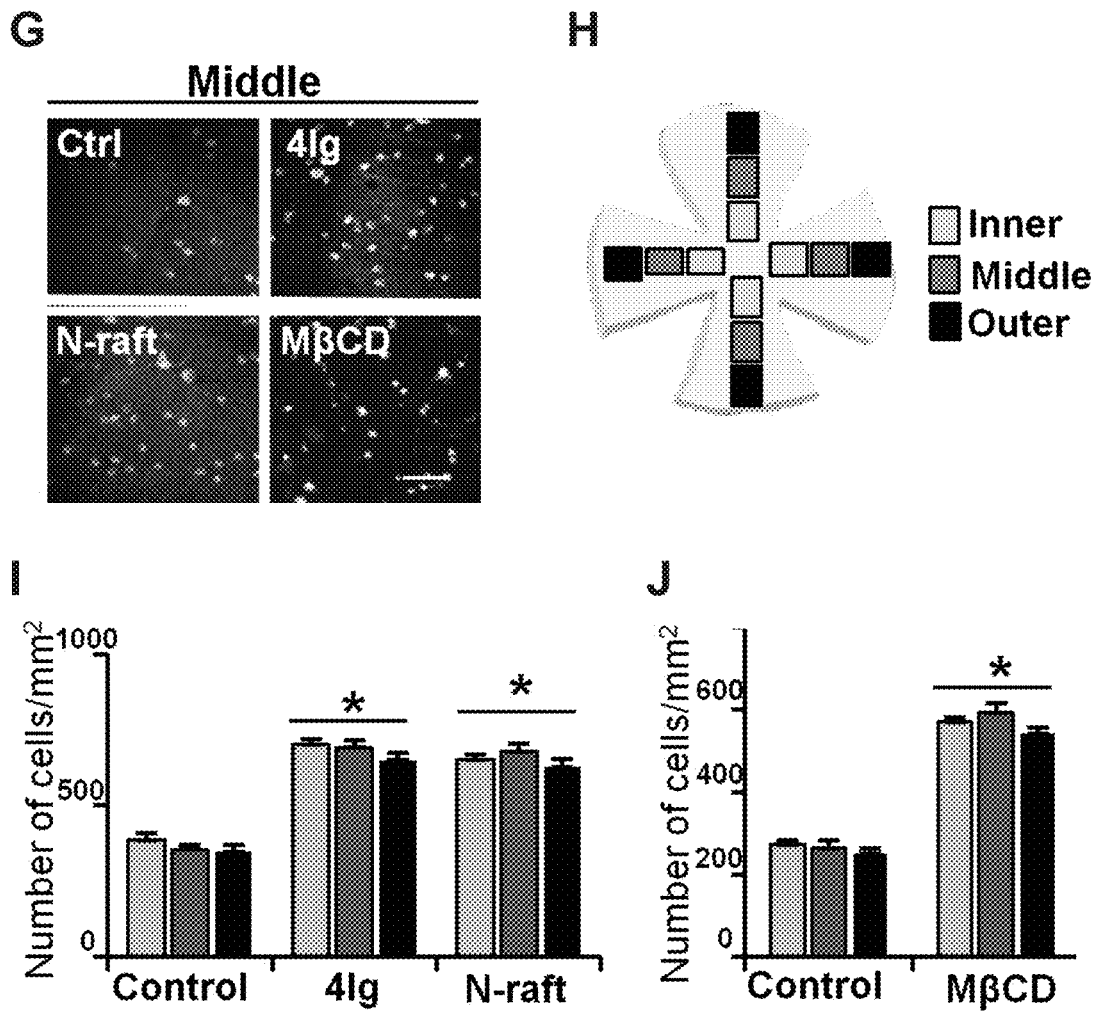

Neogenin elevated cell death by 2-fold above that seen in Mock-cells (FIG. 4A). When Noggin, 4Ig, N-Raft or MβCD was added to the medium of the Neogenin-transfected cells, cell viability was improved by about 2-3 times, indicating lipid rafts were required for Neogenin induced death (FIG. 4B).

Accordingly, these data, along with the above data, indicated that Neogenin required lipid rafts when functioning with RGMa to inhibit axonal growth and when function without RGMa to induce apoptosis. As such, preventing Neogenin transport into lipid rafts simultaneously promoted axon growth and cell survival.

RGMa was expressed in the developing chick neural tube, and thus, to determine if Neogenin required lipid rafts for its pro-death function in vivo, apoptosis was examined in the neural tubes of chick embryos (E2). Specifically, a GFP-construct was electroporated with plasmids that expressed either Mock or Neogenin and apoptosis was assayed by TUNEL staining.

In contrast to Mock expression, which did not induce apoptosis (FIG. 11), numerous TUNEL+ cells were observed in GFP-Neogenin transfected cells (FIGS. 4C and 4D). This pro-apoptotic effect of Neogenin was abolished when either 4Ig or N-Raft was injected into the tecta following Neogenin-electroporation. 4Ig and N-Raft reduced the number of TUNEL+ cells by about 18-fold (from 432±23 to 23±4) and about 4-fold (from 432±23 to 103±8), respectively (FIG. 4D). These data indicated that Neogenin was required to be present in the lipid rafts for apoptosis to occur in the developing brain. Furthermore, the above data demonstrated that Neogenin required lipid rafts to induce apoptosis, and thus, preventing Neogenin recruitment or localization to lipid rafts via 4Ig or N-Raft or cholesterol depletion with MβCD blocked the induction of apoptosis.

Example 8

Neogenin Required Lipid Rafts to Induce Apoptosis in Injured Retinal Neurons

The above data indicated that lipid rafts were required for RGMa/Neogenin pathway to function during brain development. The RGMa/Neogenin pathway mediated neuronal death in the injured central nervous system (CNS). Accordingly, whether localization of Neogenin in lipid rafts was needed for the pathophysiological roles of Neogenin was examined.

For this study, retinal organotypic cultures were used, in which axotomy of retinal ganglion cells (RGCs) deprived the cells of tropic factors and induced apoptosis. Cell death was detected using propidium iodide (PI) and all images were taken at the same intensity with the RGC-layer in focus. Cell death was gauged by measuring the relative PI intensity of whole mounts. The presence of either 4Ig or N-Raft in the medium significantly reduced cell death (by about 40%) (FIGS. 4E and 4F). Perturbing lipid rafts with either MβCD or CO similarly enhanced cell survival by about 50% vs. control (FIGS. 4E and 4F).

Accordingly, these data indicated that localization of Neogenin in lipid rafts was required for Neogenin to induce apoptosis in injured neurons. This apoptosis in the injured neurons was significantly reduced in the presence of 4Ig or N-Raft, which prevented recruitment of Neogenin to lipid rafts by blocking the cis interaction between RGMa and Neogenin, or MβCD or CO, which depleted cholesterol and disrupted lipid rafts. As such, 4Ig, N-raft, or cholesterol depletion with MβCD or CO promoted cell survival by blocking the induction of apoptosis by Neogenin.

After injury, higher levels of both Neogenin and RGMa were observed in the retina. Additionally, RGMa and Neogenin caused apoptotic-death of retinal ganglion cells (RGCs) in vivo following axotomy. To determine if Neogenin required lipid rafts in vivo to induce apoptosis after injury, 4Ig or N-Raft was injected intra-ocularly and cell survival was measured 14 days after axotomy. Both 4Ig (682±21 cells/mm$^2$) and N-Raft (652±24 cells/mm$^2$) increased RGC survival about 2-fold vs. control (361±19 cells/mm$^2$) (FIGS. 4G and 4I). Systemic application (intraperitoneal, IP) of MβCD also increased RGC survival about 2-fold (FIGS. 4G and 4J). CO was not stable in vivo and thus, was not tested. These data further indicated that Neogenin-induced apoptosis in the injured CNS required Neogenin association with lipid rafts. This association was dependent upon the cis interaction between the 4Ig-domain of Neogenin and N-Raft of RGMa.

Example 9

Neogenin Required Lipid Rafts to Inhibit Axonal Regeneration After Spinal Cord Injury As described above and shown in FIGS. 3 and 4, segregating Neogenin from lipid rafts supported axonal outgrowth and halted neuronal death in the developing CNS. Additionally, improved survival of RGCs following axotomy in vivo was observed as shown in FIGS. 4G-4J.

RGMa was expressed by radial glia cells during development and acted as a guidance molecule. RGMa was expressed by reactive astrocytes and oligodendrocytes in the injured CNS. In both developing and regenerating CNS, RGMa functioned as an inhibitor of axonal growth.

As the above data demonstrated that preventing Neogenin association with lipid rafts suppressed the inhibitory function of the RGMa/Neogenin pathway in developing RGCs, studies were performed in injury models, in which the RGMa/Neogenin pathway impeded regeneration, to determine if Neogenin association with lipid rafts was required by the RGMa/Neogenin pathway to impede regeneration of the injured CNS.

Regeneration after spinal cord injury (SCI) in a rat spinal cord compression model closely mimicked human SCI. Specifically, functional recovery was monitored weekly using the BBB locomoter rating scale, motor subscore, and ladder-walk tests.

Treatment with either 4Ig (intravenous, IV) or MβCD (IP) showed significant functional recovery as early as 2-3 weeks post-SCI as evidenced by a higher BBB score and motor subscore compared to controls (FIGS. 5A, 5B, 5D, and 5E).

Figure 5:
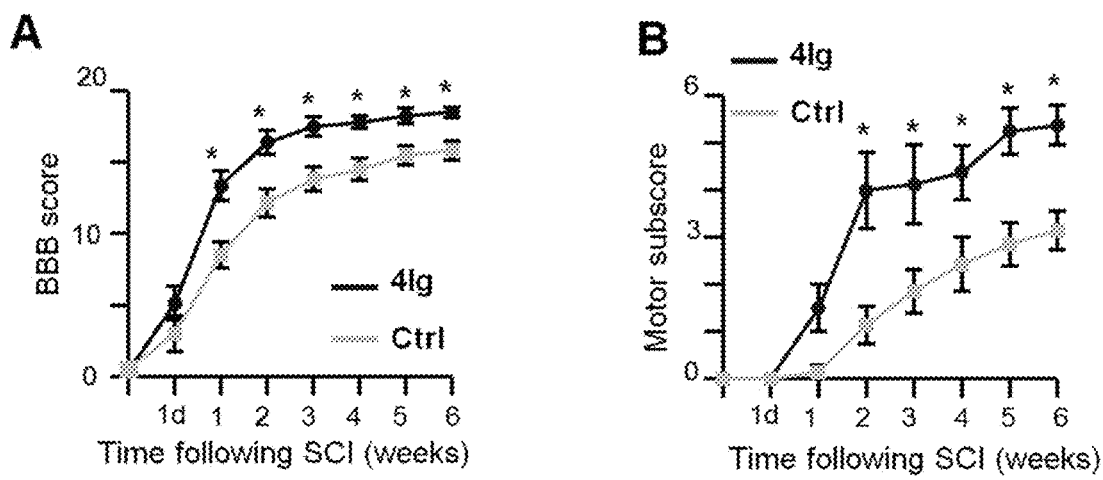
FIG. 5 shows that altering Neogenin presence in lipid raft promoted functional recovery and neuronal survival after spinal cord injury. Behavioral assessment using the BBB (A, D), motor subscore (B, E), and average number of footfalls (C, F) showed that systemic treatment with 4Ig (IV) or MβCD (IP) resulted in marked functional improvement in spinal cord injured rats vs. Control. Data were average±SEM (Control: n=7; 4Ig: n=8; MβCD: n=8) (* p<0.005). (G, H) Behavioral assessment using the BBB (G), and average number of footfalls (H) showed that intrathecal application of 4Ig resulted in marked functional improvement in spinal cord injured rats vs. Control. Data were an average±SEM (Control: n=10; 4Ig: n=10) (* p<0.005). (I-M) Longitudinal sections of an injured spinal cord stained with the neuronal marker, NeuN. The insets display perilesional neurons in the injured spinal cord from rats after systemic treatment with (I) vehicle control, (J) 4Ig, and (K) MβCD. Arrows point to neurons after 4Ig and MβCD treatments. Dotted line indicates border between white and grey matter. Quantification of experiments presented in I-K show that treatment with (L) 4Ig and (M) MβCD resulted in a significant increase in the number of spared neurons after SCI. For each animal, the absolute number of neurons was quantitated from 5 sections at equivalent anterior-posterior distance through the thickness of each cord encompassing equivalent gray matter tissue. (N-O) Neu-N staining of cross-sections of injured spinal cords after intrathecal treatment with 4Ig. The insets display cord from rats treated with (N) vehicle, and (O) 4Ig. Arrow heads point to neurons. (P) Quantification of experiments presented in N-O show that intrathecal treatment with 4Ig resulted in a significant increase in the number of neurons after SCI. Quantification at different distances to the lesion site are presented in FIG. 12D. Bar, 100 µm. Data were an average±SEM (n=8 animals/condition), *p<0.001. Scale bars, 100 µm.

Hindlimb coordination was assessed using the ladder-walk test where footfalls were considered errors and thus, a higher score reflected poorer coordination. Compared to controls, rats injected with 4Ig had fewer footfalls (FIG. 5C). A similar pattern of functional improvement was also observed in rats injected with MβCD (FIGS. 5D-5F).

Additionally, staining for astrocytes indicated that the treatments with 4Ig and MβCD did not affect these cell populations. Thus, the observed improvement in motor functions resulted from improved neuronal survival or axon regeneration (FIG. 12).

To determine that the effect observed with 4Ig resulted solely from an action of this peptide at the injury site, local intrathecal application using Alzet mini-osmotic pumps was performed. To lower spontaneous recovery, a stronger clip was used to perform compression (26 vs 20). Similar to the systemic application described above, local application of 4Ig showed significant functional recovery as early as 2-3 weeks post-SCI as evidenced by a higher BBB score (FIG. 5G). Here also, hindlimb coordination was significantly improved and rats locally-injected with 4Ig had fewer footfalls (FIG. 6H).

Figure 13:
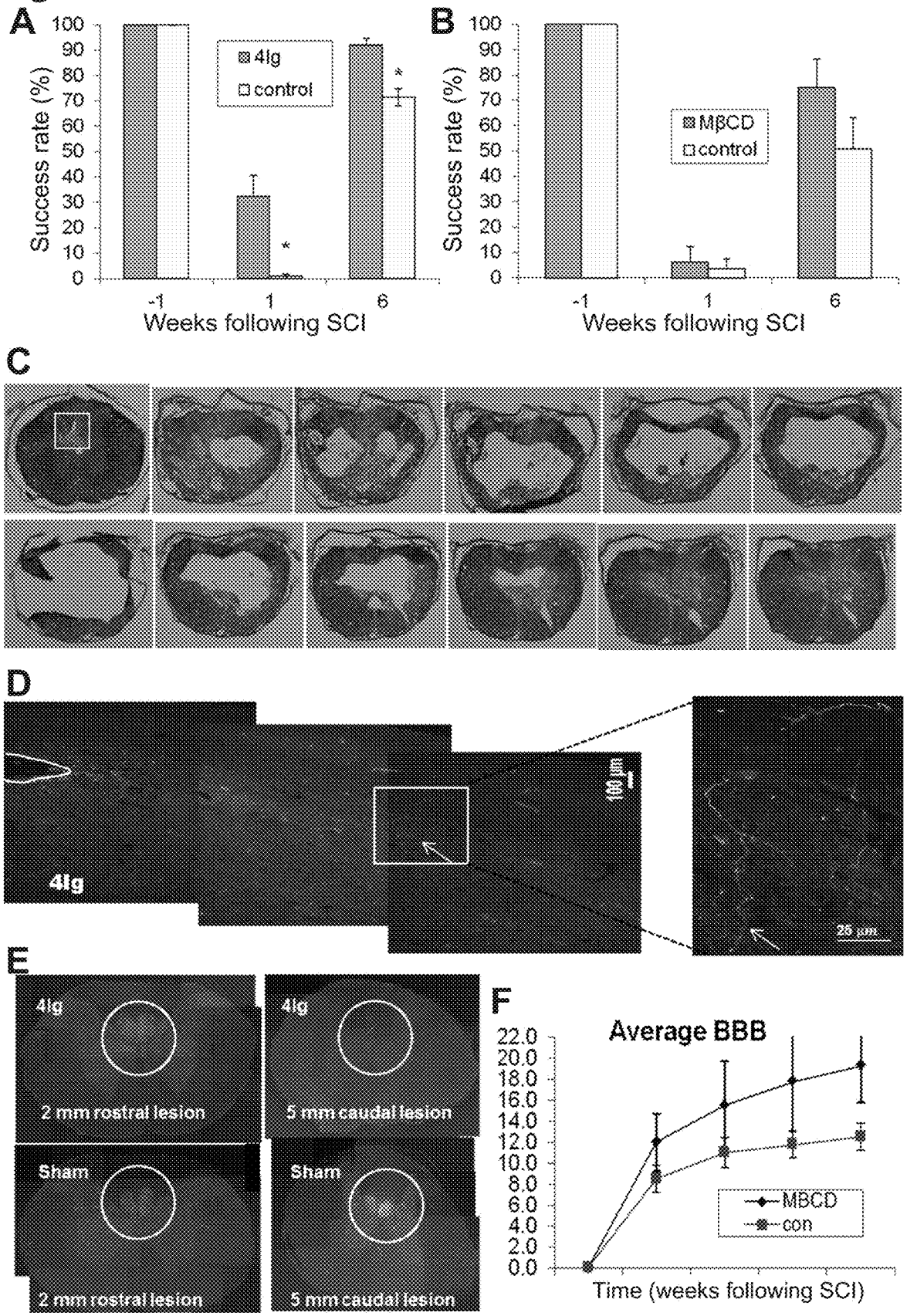
FIG. 13 shows treatments with 4Ig and MβCD improved functional outcome after spinal cord injury. Behavioral assessment after injury and treatments. (A,B) Recordings were analyzed in slow motion; the number of footfalls per hindlimb was recorded and the average was calculated for each rat per week. Injured rats with dragging hindlimbs were scored the maximum footfalls of 12. Uninjured rats had 0 or occasionally 1 footfall per crossing. The relative success rate on the test was calculated and is presented here. Treatment with 4Ig or MβCD resulted in marked functional improvement in spinal cord injured rats vs. Controls. Data were average±SEM (Control: n=8; 4Ig: n=8; MβCD: n=8) (*p<0.005). (C) H/E&LFB staining of spinal cord cut in cross-section rostrally to caudally showing typical cavitation and complete ablation of the cortico-spinal tract at the epicenter after clip compression spinal cord injury in rat (20 g injury at level T8). The corticospinal tract (CST) was marked by the box in the first rostral section which was intact. (D) Panels show BDA labeled fibers ~1000 um caudal from lesion in 4Ig rat injected with BDA at 4 wks. The box shows a higher magnification of the tortuous morphology of the BDA labeled fibers (Arrows). Labeled fibers were not apparent at further distances caudal from the lesion site in 4Ig rats injected with BDA at 4 wks. (E) BDA staining of cross-sections of the spinal cord 2 mm rostral and 5 mm caudal to the lesion site (T8) of a 4Ig treated rat and an uninjured control showing corticospinal tract axons. In cross-sections, BDA axonal profiles are apparent in the CST (circled) 2 mm rostral to the lesion site in 4Ig and uninjured controls. BDA labeled CST axons are also present 5 mm caudal to the lesion site in uninjured control rats showing continuity of the CST. In contrast, no BDA labeled axons are apparent in 4Ig treated rats in sections 5 mm caudal to the lesion site showing the disruption of the CST and no axonal sparing. (F) Behavioral assessment of old rats treated with MβCD: Elderly rats (>7 months) were injured and treated with MβCD for a period of 4 weeks. BBB assessment showed that treatment with MβCD resulted in marked functional improvement in spinal cord injured rats vs. Control. An effect was observed as soon as 7 days following injury, which fits with the notion that MβCD treatment also promote survival. Data were average±SEM (Control: n=4; MβCD: n=4) (* p<0.05).
Figure 15:
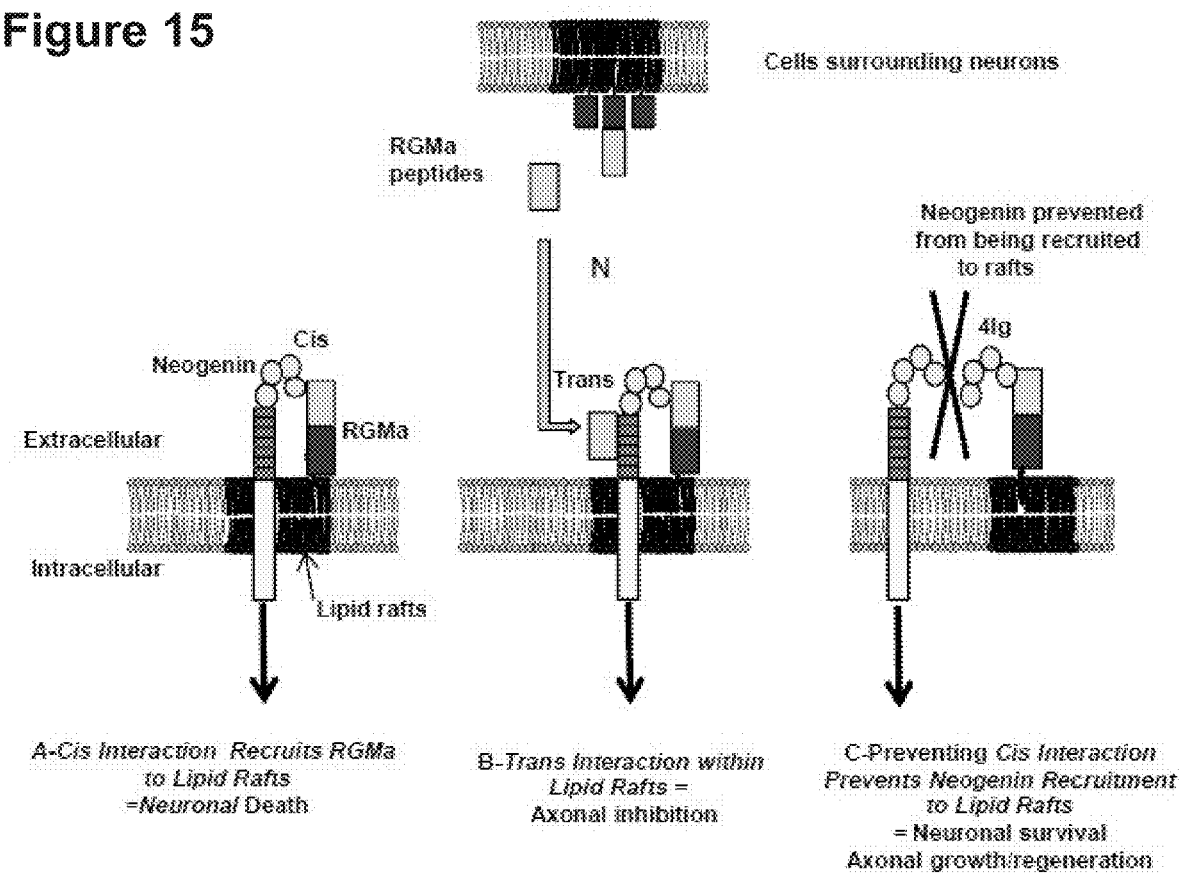
FIG. 15 shows model for RGMa action on Neogenin. RGMa and Neogenin establish two kinds of interactions to control neuronal death and axonal growth/regeneration. A) A cis interaction between the N-terminal part of RGMa and the 4Ig domain in Neogenin recruits Neogenin into lipid rafts. Once recruited in lipid rafts, Neogenin will induce cell death in the absence of a secreted source of RGMa from the environment. B) A trans interaction occurs between two distinct domains with the C- and N-terminal part of RGMa and the FNIII domain in Neogenin interaction between RGMa and Neogenin regulates axonal growth/regeneration inhibition. RGMa peptides interacting in trans are secreted by cells in the direct surrounding of the neurons. To block axonal growth/regeneration Neogenin needed to be present in lipid rafts. C) Because Neogenin requires lipid rafts association to cause cell death and block axonal growth/regeneration, altering Neogenin recruitment into these compartments can be used to prevent its function. This can be done using agents that include peptides like the 4Ig peptide (represented here), the N-raft peptide, or lipid raft disruption. Preventing Neogenin association with lipid rafts promotes cell survival and axonal growth/regeneration.

The effects of MβCD on locomotor recovery was tested in older animals (greater than 7 month, n=4), post-SCI. Similar to the results with young animals, MβCD-treatment provided marked improvements (+6.8 BBB points vs. control; FIG. 13C).

Accordingly, the above results indicated that hindering the association of Neogenin with lipid rafts via 4Ig or MβCD stimulated functional locomoter recovery following SCI.

Example 10

Neuronal Sparing and Motor Axon Regeneration

Neuronal loss after SCI resulted in loss of muscle control and eventual paralysis. The RGMa/Neogenin pathway triggered neuronal cell death in the injured CNS. Accordingly, studies were performed to examine whether blocking Neogenin association with lipid rafts halted neuronal loss and accelerated axonal regeneration after SCI and the ensuing functional recovery.

In this study, injured rats received systemic application of either 4Ig or MβCD for 6 weeks and peri-lesional neurons were quantified with the neuronal marker, NeuN. 4Ig or MβCD treatment increased the number of peri-lesional neurons compared to controls by about 2-fold (FIGS. 5I-5M). Intrathecal application of 4Ig over a 6 week period resulted in a similar increase (about 2-fold) of NeuN positive cells in cross-sections of the spinal cord (FIGS. 5N-5P and FIG. 12E). Measurements revealed that the lesion volumes for 4Ig and MβCD treated animals did not significantly vary when compared to controls (FIG. 12D). Accordingly, these data further indicated that blocking Neogenin association with lipid rafts attenuated neuronal loss following SCI.

Figure 6:
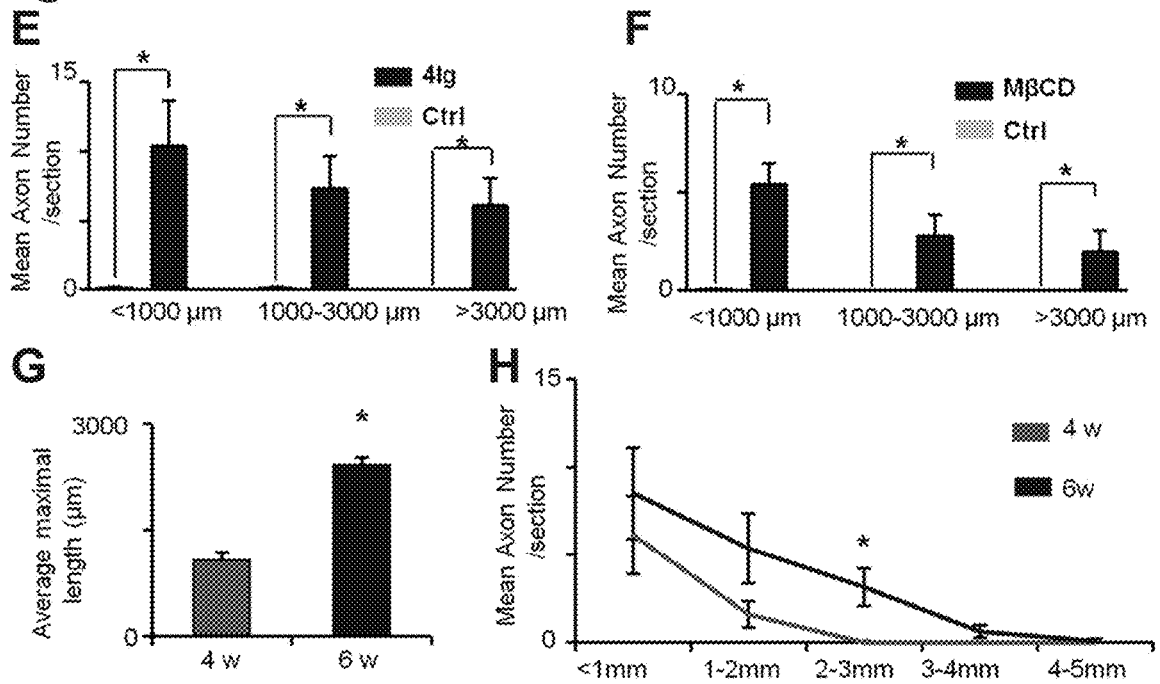
FIG. 6 shows that altering Neogenin presence in lipid rafts promoted axonal regeneration in the myelinated spinal cord. To visualize axons from the cortico-spinal tract, anterograde axonal tracing with biotin dextran amine (BDA) was performed at 6 weeks post-SCI. (A) Top panel displays a control spinal cord after injury. The insets represent higher magnifications. The lesion cavity is presented on the left. (B) Injured spinal cord treated with 4Ig. Tracing with BDA revealed fibers caudal to the cavity in 4Ig experiments but not in Control. The longest regenerating axons extended several mm beyond the caudal end of the cavity. Arrows indicate fibers. Arrow heads in the insets indicate turning fibers. Scale bar, 100 µm. (C, D) Average maximal length post-SCI was increased following (C) 4Ig and (D) MβCD treatments. Data were average±SEM (n=4 independent rats/condition; 3-4 sections/rat), *p<0.001. The average number of regenerating axons/section was measured, which showed greater number of regenerating axons in injured rats treated with (E) 4Ig and (F) MβCD. Data were an average±SEM (n=4 independent rats/condition; 3-4 sections/rat), *p<0.005. (G, H) Injured spinal cord treated with 4Ig for 4 or 6 weeks (w) before animals were sacrificed and axonal length was measured. (G) The average axonal length was significantly greater at 6 weeks when compared to 4 weeks. (H) The average number of regenerating axons/section was measured, which showed a significantly higher number of axons of 3-4 mm when cords were treated for 6 weeks when compared to 4 weeks. Data were average±SEM (n=5 independent rats/condition; 3-4 sections/rat), *p<0.005.

The inability of CNS axons to regenerate was largely due to inhibitors present in the myelin that are not conducive to regeneration. To determine whether the improved behavioral outcome resulted from axonal regeneration, anterograde tracing of cortico-spinal tracts by injecting biotin dextran amine (BDA) into the motor cortex was performed (FIG. 6).

Only one control animal showed a single regenerating fiber that extended beyond the injury site (cavity). In contrast, all 4Ig and MβCD treated animals had fibers protruding beyond the cavity and some extended a few millimeters beyond this site (FIGS. 6A and 6B). The average length of the longest axon was increased in animals treated with 4Ig (2875±228 μm) or MβCD (2195±335 μm) compared to its respective controls (18±7 μm and 128±118 μm) (FIG. 6C,D). While axons were rarely seen beyond the lesion site in controls, many fibers in the 4Ig- or MβCD-group spanned beyond 3000 μm of the lesion site (FIGS. 6E and 6F).

A SCI model of impact/compression injury, in which both the dorsal and ventral aspects of the spinal cord were simultaneously compressed, was used in further studies. The severity of SCI used resulted in central cavitation of the gray matter and adjacent white matter that severed all CST axons, leaving a spared rim of subpial white matter (FIG. 13C). In 4Ig and MβCD animals, fibers that displayed aberrant paths were observed (FIG. S6D) and were indicative of axonal regeneration.

To determine that the BDA-fibers were regenerating axons, the spinal cord from 4Ig (IV-injection) treated animals was examined at different time points (n=5 for each) and it was observed that fibers were significantly longer at 6 weeks when compared to 4 weeks following injury (FIG. 6G). In particular, a significantly higher number of fibers between 2 and 3 mm caudal from the lesion was observed in 6 wk vs. 4 wk animals (FIG. 6H).

Cross-sections of the spinal cord at 3 mm rostral and 5 mm caudal to the lesion were also examined. In sham animals, spared fibers were apparent at both locations, showing the continuity of the CST in the uninjured spinal cord. In contrast, in 4Ig (IV) treated animals, fibers were observed rostral to the lesion, but not at 5 mm caudal to the lesion, indicating the lack of spared fibers. In 4IG (IV) or MBCD (IP) treated rats, labeled fibers were detected at a maximal distance of about 4 mm caudal to the lesion site, indicating that these fibers were regenerating and were not spared.

In summary, the above results indicated that excluding Neogenin from lipid rafts via 4Ig or MβCD promoted axonal regeneration after SCI and the attendant functional recovery.

Example 11

Neogenin Required Lipid Rafts to Hamper Axonal Regeneration After Optic Nerve Crush To further examine regenerating fibers, an optic nerve crush model was employed along with GAP-43, which only stains regenerating fibers. This study indicated that treatment with 4Ig or N-Raft, by blocking Neogenin recruitment to lipid rafts, promoted axonal regeneration after optic nerve injury as was also observed after spinal cord injury as described above.

Figure 7:
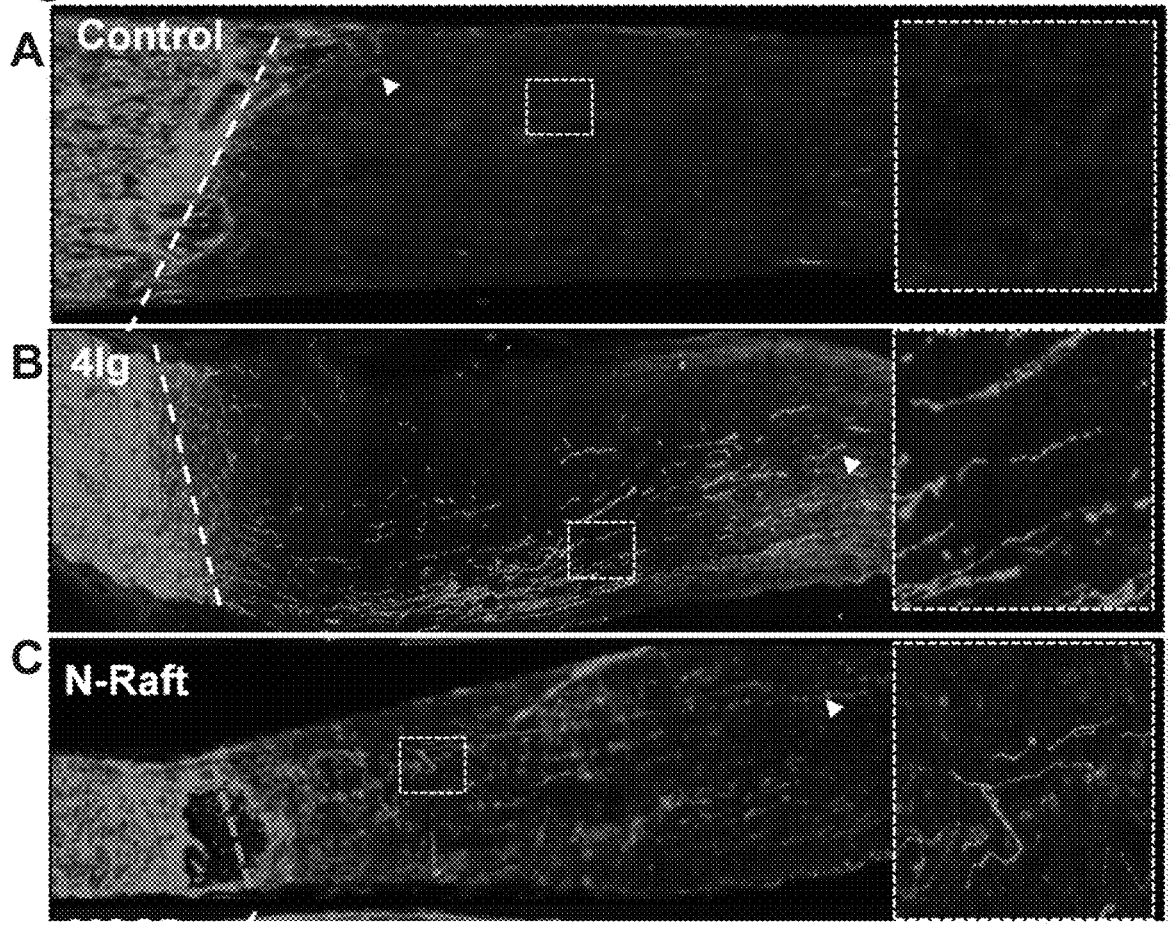
FIG. 7 shows that altering Neogenin presence in lipid rafts promoted axonal regeneration after optic nerve injury. (A-D) GAP-43 immunostaining in longitudinal sections of optic nerve at 21 days after optic nerve crush and various treatments. Compared to Controls (A), altering Neogenin presence in lipid rafts with (B) 4Ig and (C) N-Raft or (D) disrupting lipid raft with MβCD enhanced axonal regeneration past the crush site (most readily seen as dashed line in (C)) and into the distal myelinated optic nerve. Arrows demarcate some of the regenerating axons in each nerve section. Inset images are higher magnification views of regenerating axons from the corresponding section. (E) Quantification of axonal length showing 4Ig, N-Raft, and MβCD significantly enhanced axonal regeneration after optic nerve injury. Data were average±SEM (n=7 optic nerves/condition), *p<0.001. Scale Bar, 200 µm.
Figure 7:
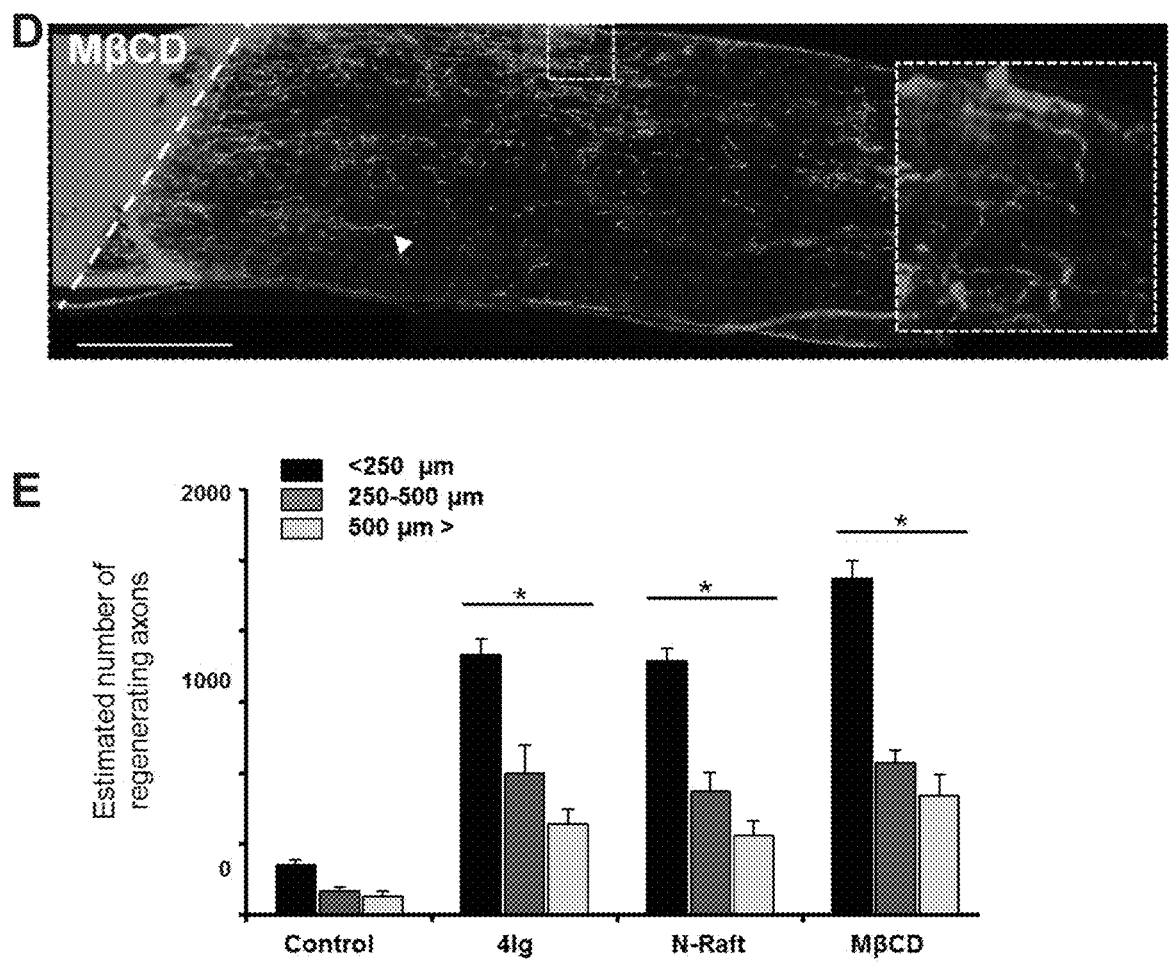

Following injury, animals received IV injections of 4Ig or N-Raft and axonal regeneration was examined 21 days later (FIG. 7). Regeneration was visualized by GAP-43 immunostaining, which localized to regenerating adult RGC-axons of the proximal and distal nerve stump.

In controls, few axons crossed the lesion site within the optic nerve and growth cones stopped abruptly at the crush site (FIG. 7A). Regenerating axons in controls were limited to less than 250 μm in length and an average of about 408 regenerating axons per optic nerve were observed beyond the lesion site (FIGS. 7A and 7E; less than 250 μm: 224±36; 250-500 μm: 108±12; and greater than 500 μm: 76±24).

In contrast, animals treated with 4Ig showed increased regeneration beyond the lesion site and more pronounced axon sprouting in the proximal segment of the nerve (FIGS. 7B and 7E). Quantification of axon numbers by length showed that 4Ig significantly increased the number of regenerating axons by 5.7-fold relative to controls (FIG. 7B,E; less than 250 μm: 1134±68; 250-500 μm: 640±128 and greater than 500 μm: 410±64). Animals that received N-Raft also showed regeneration beyond the lesion site to a degree comparable to 4Ig (FIGS. 7C and 7E). Accordingly, these data indicated that both 4Ig and N-Raft improved axon-regeneration in the myelinated adult CNS.

Whether cholesterol depletion promoted axonal regeneration after optic nerve crush was also examined in these studies. Axonal length was measured in rats that were treated over a 28-day period with MβCD (FIGS. 7D and 7E). For all distances measured, the average number of axons per section in animal treated with MβCD (IP injection) was significantly higher than controls by 7.1-fold (FIGS. 7D and 7E; less than 250 μm: 23.7±1.2; 250-500 μm: 10.7±0.9; and greater than 500 μm: 8.4±1.4).

The intraretinal integrity of RGC axons after optic nerve crush was examined for increased axon/soma preservation by the 4Ig, N-Raft and MβCD treatments 4 weeks following injury. The cell bodies of surviving RGCs with intact axons were visibly labeled with CTB-FITC (FIG. 14C). Treatments with 4Ig, N-Raft and MβCD resulted in (1) thicker axon bundles throughout the retina and (2) increased labeling of RGC somata, which was consistent with a role of these treatments in both cell survival and axonal regeneration.

In summary, these data showed that Neogenin mediated the failure of axons to regenerate after optic nerve injury and that preventing Neogenin association with lipid rafts via 4Ig, N-Raft, or MβCD resulted in axonal regeneration.

Because astroglia cells were not affected by the 4Ig, N-Raft, or MβCD treatments, the pro-regenerative effect of these treatments resulted from an effect on regenerating axons (FIG. 14). Accordingly, these data demonstrated that altering Neogenin presence in lipid rafts promoted axonal regeneration after CNS-injury.

Example 12

Materials and Methods for Example 13

Provided herein in Example 12 are materials and methods that were used in the experiments described below in Example 13.

Constructs.

All constructs used in this study, unless otherwise noted, were generated from the *Gallus gallus* species. Specifically, N-RGMa (i.e., amino acids 28-73; referred to also as "N-Raft" herein) was divided into four overlapping fragments: (1) amino acids 28-54, referred to herein as "N-RGMa (28-54aa)"; (2) amino acids 40-62, referred to herein as "N-RGMa (40-62aa)"; (3) amino acids 55-73, referred to herein as "N-RGMa (55-73aa)"; and (4) amino acids 64-62, referred to herein as "N-RGMa (54-62aa)". These sequences were cloned in the Psectag2B-AP plasmid, which allowed for secretion of the peptides as soluble proteins that were fused with an alkaline phosphatase tag.

Binding Assay.

The assay was conducted in a 96-well microtiter plate (Corning Incorporated). The wells were coated with 100 μl (10 μg/mL) of Poly-L-Lysine at 4° C. overnight. Wells were then washed three times with 100 μl of PB ST (+0.02% Tween).

50 μl (2.5 μg/mL) of His-tagged: Full-length Neogenin; the 4Ig-domain of Neogenin; and 6FNIII-domain of Neogenin were coated onto each well for 1 hour at 37° C. Following three washes of 100 μl PBST, each well was then blocked with 300 μl of 3% BSA in PBST for 1 hour at 37° C.

50 μl (1.0 μg/mL) AP-tagged: N-RGMa (28-73); N-RGMa (28-54); N-RGMa (40-62); N-RGMa (54-73); N-RGMa (54-62) in 1% BSA+PBST was then added to each well and incubated at 37° C. for 1 hour. Each well was washed thoroughly three times with 100 μl PBST followed by subsequent equilibration of each well with Alkaline Phosphatase (AP) developing buffer (100 mM $NaHCO_3$, 1 mM $MgCl_2$). The reaction was developed using AP developing buffer supplemented with, p-nitrophenyl phosphate (pNPP) (Sigma-Aldrich) and allowed to develop until color development. The reaction was stopped with the addition of 50 μl (0.1M) NaOH. The absorbance of each reaction was measured using a microplate autoreader (BIO-TEK Instruments Inc.) at 405 nanometers (nm) wavelength.

Example 13

As described above, N-Raft of RGMa bound to the 4Ig-domain of Neogenin to mediate the cis interaction between RGMa and Neogenin that was required for Neogenin localization to lipid rafts. N-Raft was residues 28-73 of RGMa. To further identify the binding site within N-Raft for the 4Ig-domain of Neogenin, N-Raft was divided into four overlapping fragments: N-RGMa (28-54aa); N-RGMa (40-62aa); N-RGMa (55-73aa); and N-RGMa (54-62aa). These four fragments were purified and tested for binding to full-length Neogenin, the 4Ig-domain of Neogenin, and the 6FNIII-domain of Neogenin (FIGS. 17A-17C).

These studies demonstrated that N-RGMa (40-62aa) and N-RGMa (54-73aa) bound specifically to the 4Ig-domain of Neogenin (FIG. 17C). Full-length RGMa, as also described above, did not bind to the 4Ig-domain of Neogenin. Additionally, N-RGMa (28-54aa) did not bind to the 4Ig-domain of Neogenin.

N-RGMa (54-62aa), which overlapped with the fragments that bound 4Ig, i.e., N-RGMa (40-62aa) and N-RGMa (55-73aa), did not bind to the 4Ig-domain of Neogenin. This result indicated that the amino acids and/or structure required for binding to the 4Ig-domain of Neogenin was located between residues 40-73 of RGMa.

The binding studies revealed that two overlapping fragments: N-RGMa (40-62aa) and N-RGMa (55-73aa) bound specifically to the 4Ig domain of Neogenin whereas the full-length RGMa protein as well as the N-RGMa (28-54aa) fragment did not. N-RGMa (SEQ ID NO:10) and N-RGMc (SEQ ID NO:9) from mouse were also tested and demonstrated binding to the 4Ig domain of Neogenin, as did the N-RGMa portion from human Neogenin (data not shown).

In an effort to further isolate the binding domain of N-RGMa, a fourth overlapping fragment N-RGMa (54-62aa), overlapping the specific region of interest identified in the above mentioned binding studies, was studied for its binding properties to Neogenin. The N-RGMa (54-62aa) fragment did not bind to the 4Ig domain of Neogenin. This revealed that a crucial folding composition was required for the binding of N-RGMa to the 4Ig of Neogenin, in the regions of 40-73aa.

Example 14

Retinal Degeneration

The irreversible loss of rods was a major determinant of the progressive and permanent functional deficit in Retinitis Pigmentosa (RP) patients. The rods were lost due to apoptosis, which resulted from genetic mutation. In RP, however, there was also a progressive loss of cones. Blocking Neogenin recruitment to lipid rafts promoted neuronal survival in vivo and in vitro when oxidative stress was present. Oxidative stress contributed to cone death in RP. Accordingly, studies were performed to determine if blocking Neogenin recruitment to lipid rafts inhibited photoreceptor cell death and promoted cone and rod survival in retinal degeneration.

Specifically, these studies demonstrated that Neogenin was expressed in adult rods and cones (FIG. 18). rd1 mice were used to determine if Neogenin was involved in rod death. The rd1 mouse model is a model for human RP and carried a loss-of-function mutation in the gene encoding for the β-subunit of the rod photoreceptor cGMP phosphodiesterase-6.2. This loss-of-function mutation led to an accumulation of cGMP, which caused photoreceptor cell death. Specifically, rd1 mice showed apoptosis 9 days after birth (P9) and at P21, over 90% of the photoreceptor cells were dead.

In these studies, intraocular injection of the 4Ig (2 μg/μl) peptide at P9 and P15 was performed and animals were sacrificed at P21 to examine cell survival. Treatment with the 4Ig peptide significantly improved the number of photoreceptors within the retina as compared to control animals, which did not receive the treatment with the 4Ig peptide. Additionally, in the control animals, which were injected with PBS instead of the 4Ig peptide, the photoreceptor layer had a thickness of an average of about 2 cells. Injection of 4Ig increased outer nuclear layer (ONL) thickness to about 6 cells (FIG. 19). This measurement was the average thickness of the ONL. Accordingly, these data indicated that treatment with the 4Ig peptide, which as described above blocked Neogenin localization to lipid rafts, increased the thickness of the ONL more than three-fold as compared to the control mice.

Figure 21:
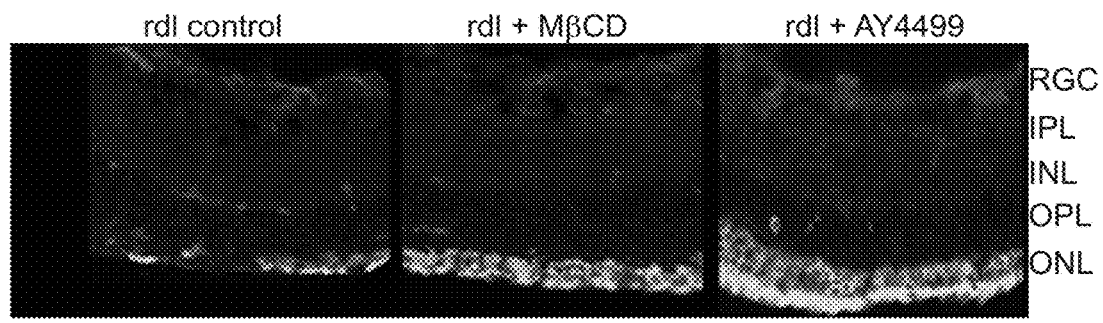
FIG. 21 shows Cholesterol depletion/inhibition promotes rods survival: rd1 mice were injected at P9 with PBS (control) or with the MBCD or AY-9944. At P21 animals were sacrificed and rods were stained with an anti-Rhodopsin antibody. In MBCD and AY-9944 injected animals, we could observe a dramatic increase in the number of rods within the Outer Nuclear Layer.

To determine if disrupting lipid rafts promoted cell survival in rd1 mice, the effect of cholesterol depletion on photoreceptor cell survival was examined. As described above, cholesterol depletion removes lipid rafts. Specifically, mice were treated with daily subcutaneous (IP) injections of MβCD from P9 to P21. In these treated mice, photoreceptor survival was improved (FIGS. 21 and 22). MβCD promoted cell survival to a similar extent as observed with the 4Ig treatment, i.e., a three-fold increase in the average thickness of the ONL and an average depth of about 6 cells. Accordingly, these data indicated that depleting cholesterol promoted survival of photoreceptor cells.

Figure 20:
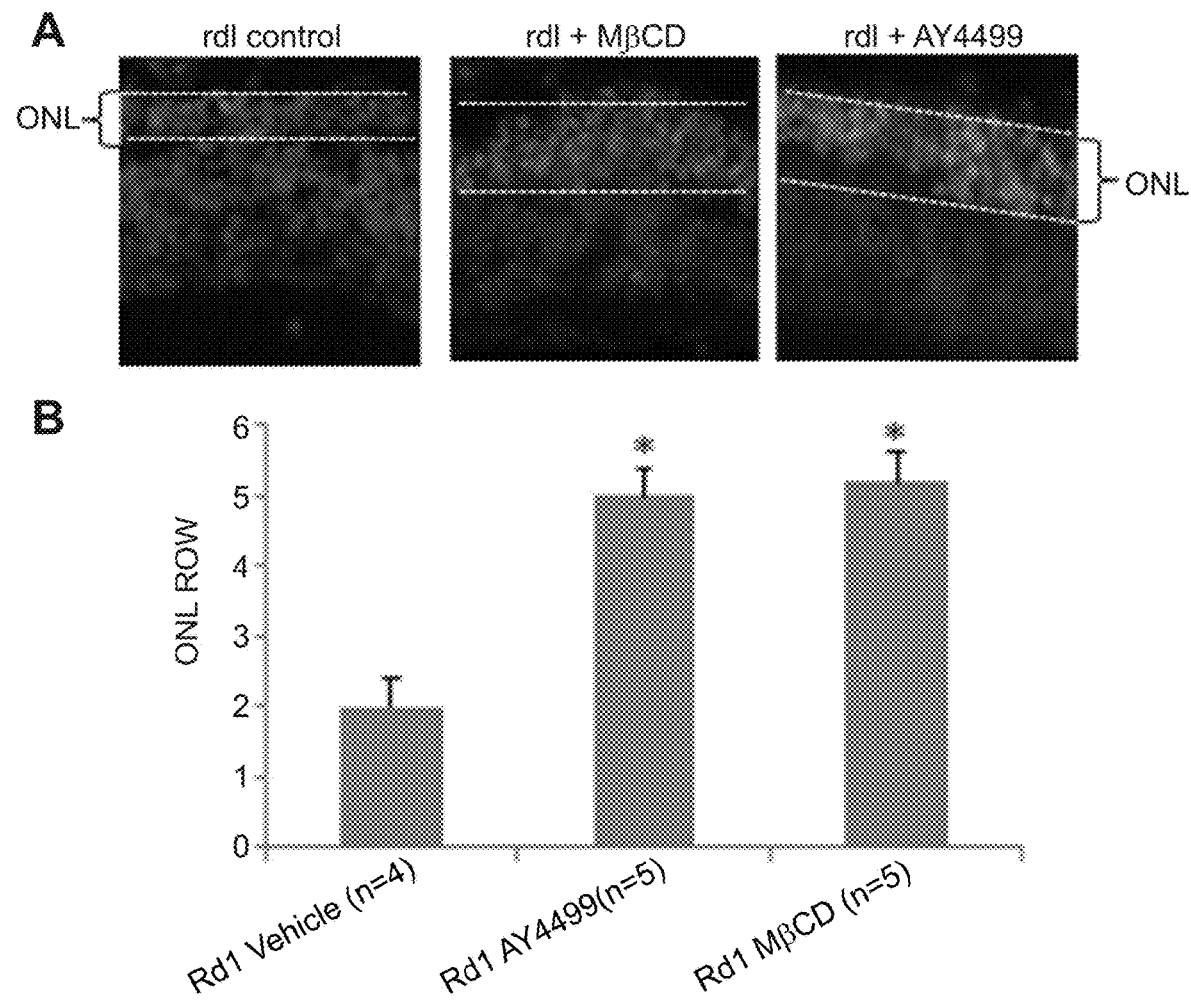
FIG. 20 shows cholesterol depletion/inhibition promotes photoreceptor survival: (A) rd1 mice were injected at P9 with PBS (control) or with the MBCD or AY-9944. At P21 animals were sacrificed and DAPI staining was performed to visualize photoreceptors. In MBCD and AY-9944 injected animals, the Outer Nuclear Layer appeared thicker in when compared to controls. B) Quantification for experiments presented in (A). The number of cells in the ONL was significantly increased in MBCD and AY-9944 treated animals vs. controls.

To examine the effect of reducing cholesterol synthesis on cell survival, AY-9944 was examined in rd1 mice (FIGS. 20 and 21). Rd1 mice were treated using two intra-peritoneal injections of AY-9944, at P9 and P15 and sacrificed at P21. Similar to MβCD, AY-9944 promoted photoreceptor survival in rd1 mice. Accordingly, these data indicated that reducing cholesterol synthesis promoted photoreceptor survival in rd1 mice.

In summary, the above data indicated that blocking Neogenin recruitment to lipid rafts reduced photoreceptor cell death and promoted photoreceptor cell survival in rd1 mice, which are a model for human retinitis pigmentosa.

Example 15

Inhibition of Cholesterol Biosynthesis with AY-9944 and BM 15.766 Promoted Growth of Retinal Ganglion Cell Neurites on Myelin As demonstrated above, AY-9944, which reduced cholesterol synthesis, promoted neuronal cell survival. To further examine the role of reducing cholesterol synthesis, studies were conducted to examine if reducing cholesterol synthesis promoted growth of retinal ganglion cell neuritis on myelin.

Specifically, retinal explants were prepared from E7 chick embryos, cultured on coverslips coated with on Laminin or myelin, and treated with control (DMSO) or AY-9944 (1 µM) or BM15.766 (4 µM), two inhibitors of cholesterol biosynthesis. After 18 hrs in culture, explants were fixed with 4% PFA and stained with Alexa488-Phalloidin. Neurites were measured using Cellsens software. Retinal explants were cultured on laminin (control) or myelin (the inhibitory compound of the CNS). On laminin, axon growth was normal compared to myelin because myelin inhibited outgrowth. When cholesterol inhibitors were added to the medium, they did not influence outgrowth on laminin. However, they restored outgrowth on myelin, which indicated that they suppressed the inhibitory activity of myelin.

Example 16

Materials and Methods for Example 17

Provided herein in Example 15 are materials and methods that were used in the experiments described below in Example 16.

Cerebral Focal Ischemia Model.

In all experiments, female Sprague-Dawley rats weighing 200-250 g were used. Briefly, focal cerebral ischemia was induced by injection of a preformed clot into the MCA. The rats were initially anesthetized with 3.0% isoflurane and then maintained with 1.5% isoflurane in a mixture of 30:70 $O_2$ and $NO_2$ with a face mask during surgery. Body temperature was maintained at 37° C. in the normothermic rats with a heating pad for the duration of surgery and in the immediate postoperative period until the animal was fully recovered from anesthesia.

A 1.5-cm longitudinal incision was made in the midline of the ventral cervical skin. The right common carotid artery (CCA), right internal carotid artery (ICA), and right external carotid artery (ECA) were exposed. The distal portion of the ECA was ligated and cut. A modified polyethylene-10 catheter, filled with bovine thrombin (Thrombostat, TM Warner-Lambert Co.), was introduced into the lumen of the right ECA via a small puncture. Ten micro liters of blood was withdrawn into the catheter and retained for 15 minutes to allow formation of a clot. Once the clot was formed, the catheter was advanced 17 mm into the internal carotid artery until its tip was 1-2 mm away from the origin of the MCA. The preformed clot in the catheter was then injected, and the catheter removed. Surgery was usually finished in 15 minutes and the wound was closed. The animal was then returned to its cage. After returning to their cage, animals were monitored for normal recovery.

Quantification of Brain Infarct Volume and Edema.

The infarct volume was expressed as a percentage of the total volume from the ipsilateral hemisphere. Brain edema was determined by calculating the volume difference between the 2 hemispheres and dividing by the volume of the left hemisphere.

Briefly, 7 days after MCA occlusion the anesthetized rats were killed. The brains were removed from the skull and cooled in ice-cold saline for about 5 minutes. For morphometric examination, 2-mm-thick coronal sections were cut using a rat brain matrix. A total of 8 coronal sections were collected, and the sections were stained using a 2% 2,3,5-triphenyltetrazolium chloride solution. The infarct appeared pale white on a background of red normal brain. The stained brain sections were scanned with the Scan Jet (Hewlett Packard) flatbed scanner. The images were analyzed and the determination of infarct volume and edema was blinded. The infarct volume was calculated using the following formula:

Infarct volume=[left hemisphere volume−(the right hemisphere volume−measured infarct volume)]/ left hemisphere volume.

Brain swelling was determined using the following formula:

Swelling (edema)=(right hemisphere volume−left hemisphere volume)/left hemisphere volume.

The infarct volume and brain swelling was expressed in percentage.

Neurological Deficits and Seizure Activity.

Neurological deficits and seizure activity of each rat was evaluated carefully at 2, 8, 24, 48, 72 hours and 1 week (six times for each rat) after ischemic injury by an observer who had no knowledge of which procedure had been performed.

Briefly, neurological deficits were determined using a modified Bederson's scoring system. In the modified system, the grading scale of 0-4 was used to assess the behavior, instead of the previous standard grading (scale 0-3) system. The modified scoring system was more clinically relevant and had more capability to assess behavior as compared with the un-modified scoring system. Seizure activity was classified with the Racine scale. Mortality was also recorded.

Example 17

Stroke

RGMa was highly expressed in the human adult nervous system (in the myelin) and in the penumbra after stroke. After focal brain ischemia in the human brains, RGMa was upregulated in the lesion site as well as in the peri-infarct region. The lesion site and peri-infarct region had restricted regeneration. As described above, RGMa inhibits axonal growth, and thus, regeneration in areas of injury. Accordingly, further studies were conducted to examine the RGMa/Neogenin pathway after an ischemic insult such as stroke.

RGMa Promoted Neuronal Survival after Ischemic Insult.

To evaluate the role of the RGMa/Neogenin pathway in stroke, stroke-induced cell death was studied using an in vitro stroke model (Oxygen Glucose Deprivation; OGD).

Specifically, retinal whole mounts were subjected to OGD for 1 hour. After ischemia, whole mounts were incubated for 24 hours and dead cells were identified using propidium iodide (PI) staining. Using this approach, it was observed that the addition of RGMa to the medium promoted cell survival (FIG. 22). This approach also showed that Neogenin mediated this promotion in cell survival because anti-Neogenin antibodies restored cell death.

Figure 23:
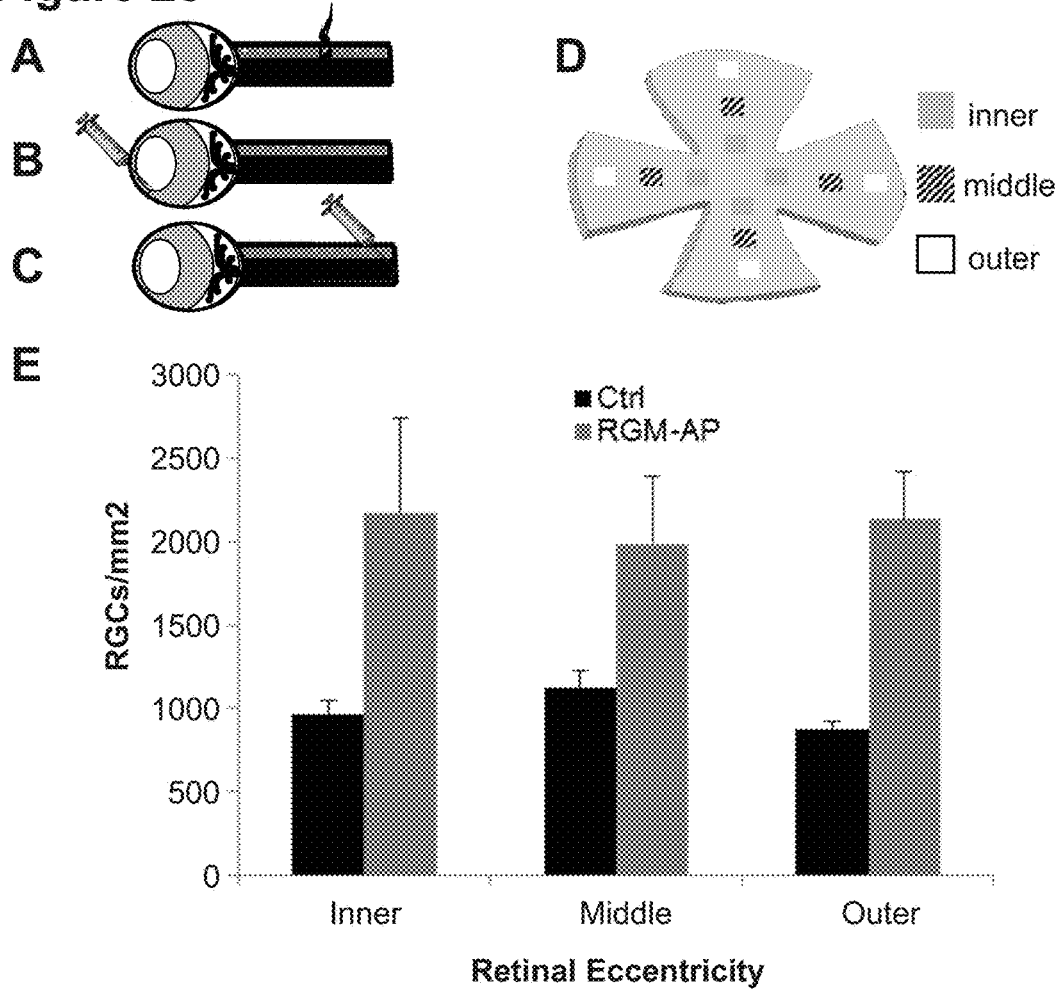
FIG. 23 shows RGMa injection promotes cell survival in an in vivo stroke model. (A,B,C) Schematic representation of the experiments performed on the eye. A) the main artery was ligated to stop blood flow for 15 min. B) RGMa was injected into the eye vitreous just after ligation. C) 2 weeks after ligation, retrograde labeling was performed to assess cell survival. D) Representation of the retinal areas used for quantification. E) Quantification of cell survival performed on 8 rats for each condition. This shows that RGMa injection promotes survival by two-fold in this in vivo stroke model.

To extend this study, whether RGMa injection into the eye affected cell survival after ligation of the main optic artery to induce ocular ischemia was tested. This injection treatment enhanced survival up to 2 times when compared to controls (FIG. 23), further indicating that the Neogenin/RGMa pathway was involved in cell death following ischemic insult.

Disrupting Neogenin Association with Lipid Rafts Promoted Cell Survival after OGD.

Figure 24:
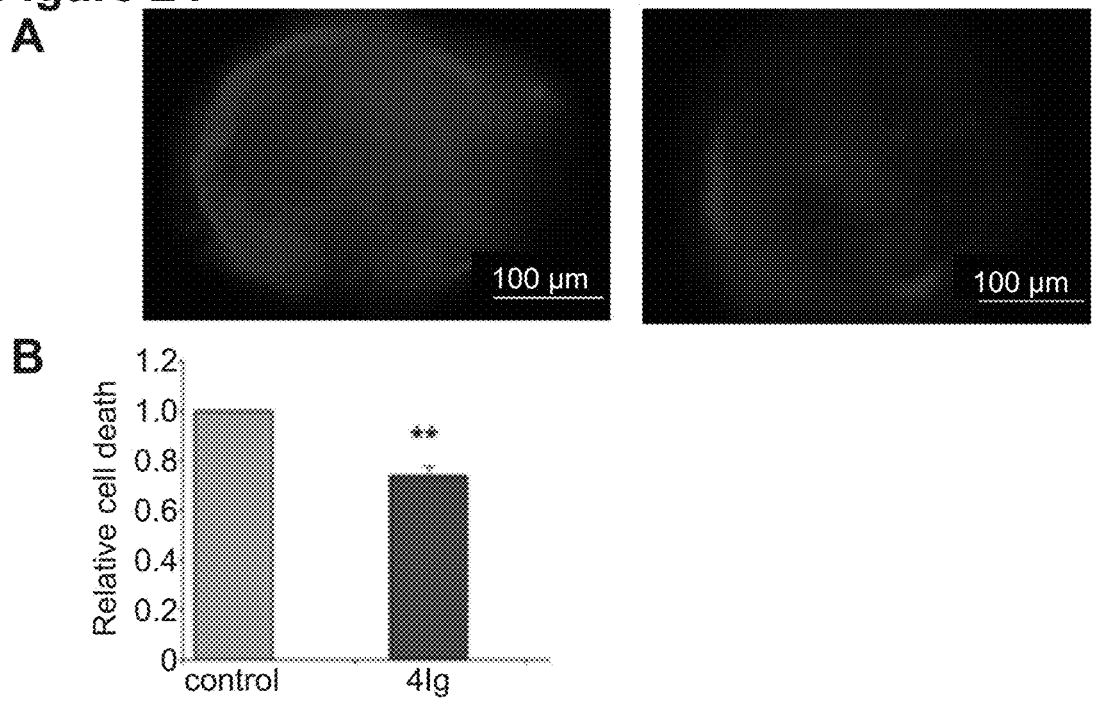
FIG. 24 shows 4Ig increases survival after OGD (Oxygen Glucose deprivation) in retinal whole mounts: A) The effect of 4Ig on cell survival was assessed in retinal whole mounts. After 2 days in culture, propidium iodide staining was performed to visualize dead cells. OGD was performed (1 h) in the presence of control or 4Ig. One day after OGD cell survival was assessed by PI staining. B) Quantification of behavior observed in A. There is a significant improvement of cell survival in 4Ig treated cultures.

To determine whether Neogenin required lipid raft association to induce cell death, OGD was performed on retinal whole mounts in the presence of 4Ig, which as described above, prevented Neogenin localization into lipid rafts. These studies demonstrated that the 4Ig peptide enhanced cell survival and reduced the number of dead neurons by two-fold compared to controls (FIG. 24).

Disrupting Neogenin Association with Lipid Rafts Reduced Brain Damage In Vivo.

Figure 25:
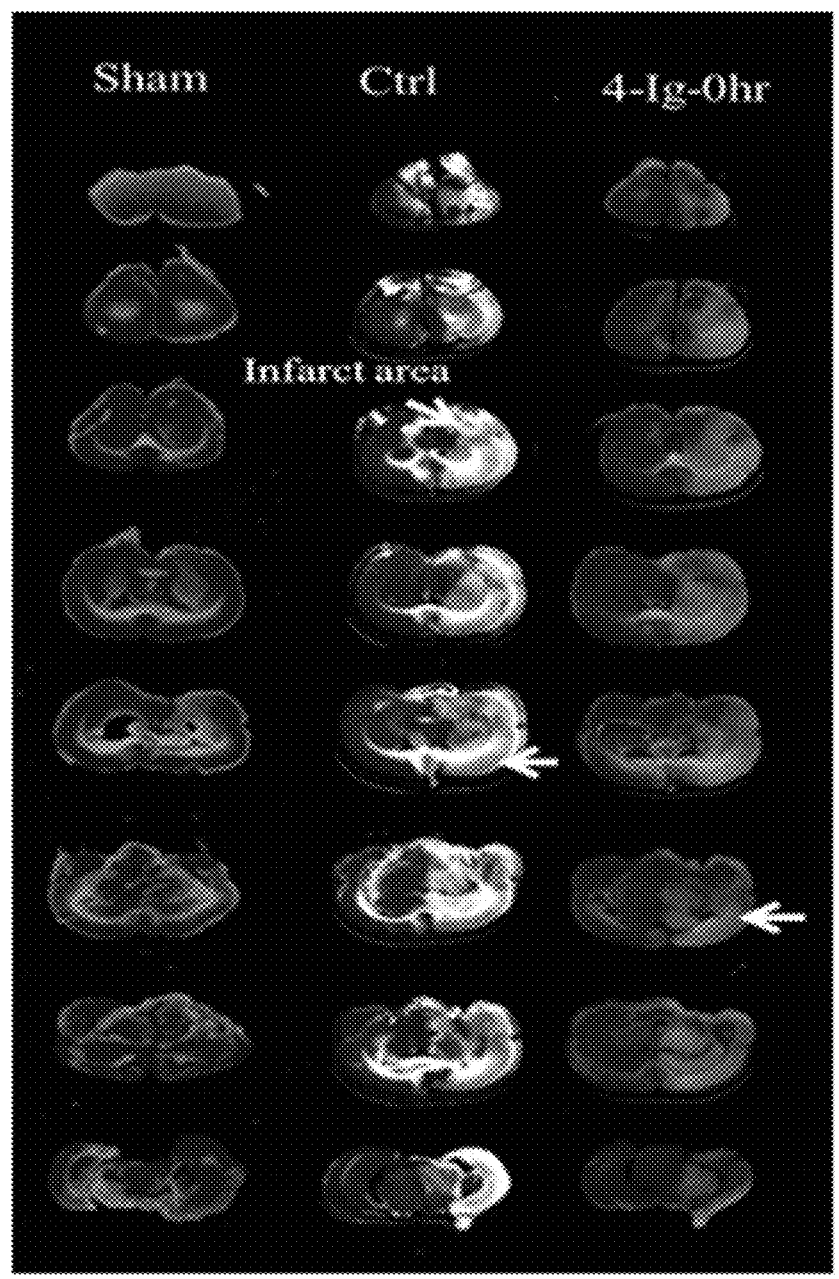
FIG. 25 shows altering Neogenin association with lipid rafts (4Ig) prevents brain damage after stroke: A blood clot was injected into the middle Cerebral Artery to create a stroke and animals were treated with tail vein injection of 4Ig (daily) and animals or control peptide. Animals were kept for a week and the brain was stained (2% 2,3,5-triphenyltetrazolium chloride solution) to visualize damages. Next cholera toxin was injected in the vitreous of the white areas (arrows) indicate damage. In 4Ig treated animals, damage was reduced when compared to controls.

To determine whether Neogenin required lipid raft association to induce cell death, Middle Cerebral Artery Occlusion was performed using a blood clot. Animals were treated by daily injections of peptide control or 4Ig. In these studies, functional assessment of the animals was performed and brain damage was examined. These studies demonstrated that brain edema and infarct volume were significantly reduced in the presence of 4Ig when compared to control (FIGS. 25 and 26). Additionally, behavioral deficits were also significantly reduced in 4Ig treated animals when compared to control (FIG. 27).

In summary, these data indicated that blocking Neogenin association with lipid rafts after an ischemic event such as a stroke, promoted cell survival and reduced brain edema, infarct volume, and behavioral deficits.

Example 18

Multiple Sclerosis

The above data indicated that the 4Ig peptide promoted neuronal cell survival and axon regeneration in the spinal cord injury and optic nerve injury models, which are relevant models for multiple sclerosis. To determine if modulating the RGMa/Neogenin pathway attenuated multiple sclerosis, the EAE mouse model was treated with the 4Ig peptide, which as described above, blocked Neogenn localization to lipid rafts.

Figure 28:
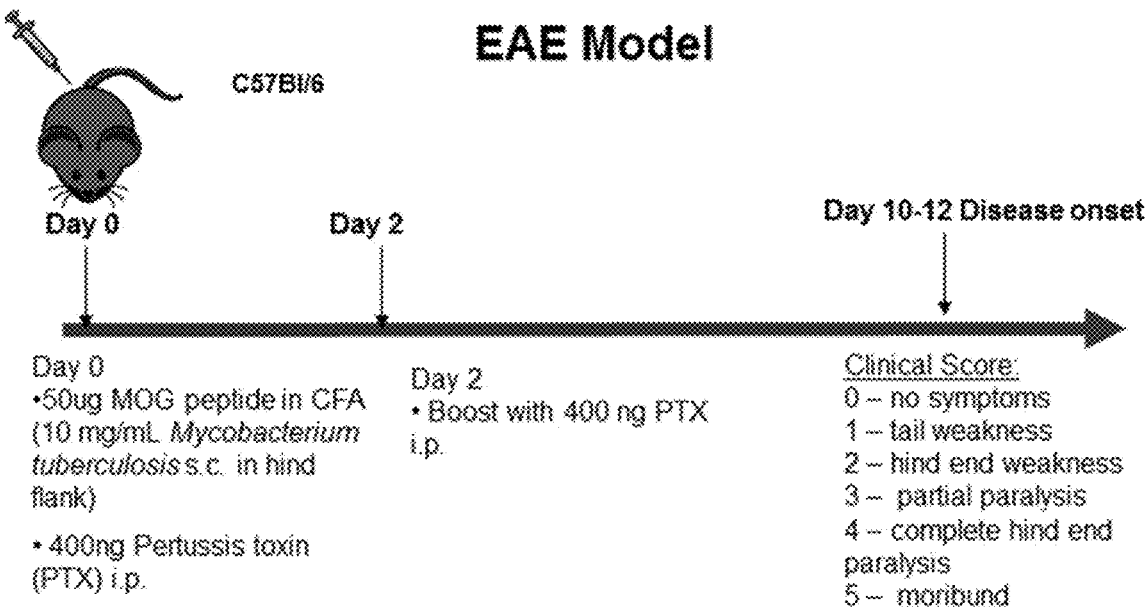
FIG. 28 shows representation of the experimental design. Schematic representation of the EAE experiments performed in mice

Specifically, whether or not 4Ig reduced paralysis in the EAE model was tested. To induce EAE, C57BL6/J mice were injected with an emulsion of MOGp35-55 peptide (50 μg, day 0) mixed with complete Freund's adjuvant (CFA). On day 2, the animals also received 400 ng of pertussis toxin (PTX) intraperitoneally in order to produce severe and reliable EAE and then were examined for clinical signs in over a 17 day period (FIG. 28).

Figure 29:
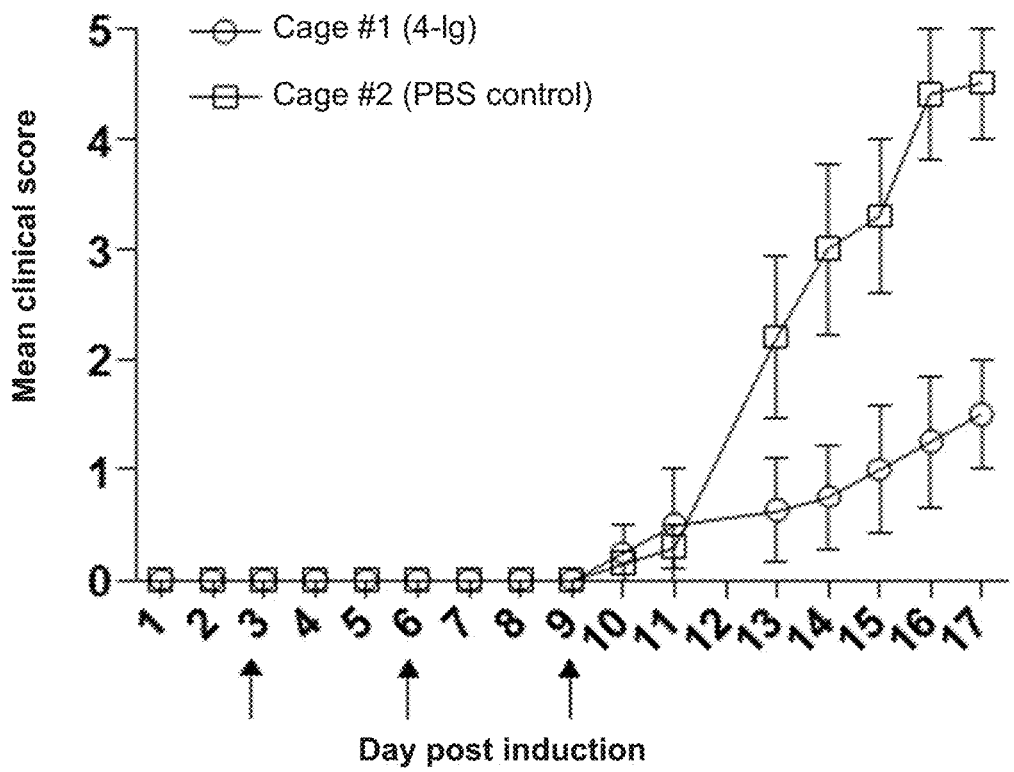
FIG. 29 shows the 4Ig peptide alleviated paralysis in EAE: EAE was induced in 10 mice, 5 per treatment group. On the days indicated with arrows mice were given either the 4Ig peptide (3 μg in PBS) or PBS as control. At day 17 control mice were severely paralyzed whereas 4Ig strongly reduced the severity of paralysis.

At days 3, 6, and 9 post-EAE induction, animals were treated with either 3 μg of 4Ig in PBS (IV injection) or PBS (Control). After 17 days, control mice exhibited a clinical score approaching 5, indicating that they were severely paralyzed (FIG. 29). In contrast, 4Ig injected mice had a significantly lower score of 1.4, indicating that Neogenin presence in lipid rafts was required for the immune-mediated paralysis in these mice because as described above, 4Ig blocked the presence of Neogenin in lipid rafts.

In summary, these data indicated that blocking Neogenin recruitment to lipid rafts via the 4Ig peptide reduced paralysis in the EAE model.

Example 19

Preparation of Antibodies that Block the Cis Interaction Between RGMa and Neogenin As described above, the following portions of RGMa bound the 4Ig domain of Neogenin: amino acids 28 to 73 (i.e., N-Raft and SEQ ID NO:2), amino acids 40 to 62 (i.e., SEQ ID NO:4), and amino acids 54 to 73 (i.e., SEQ ID NO:3). As described above, the 4Ig domain of Neogenin was amino acids 1 to 383 of Accession No. AAC59662 (SEQ ID NO:1). Other fragments may include 4Ig domain of mouse Neogenin (SEQ ID NO:8), mouse N-RGMc (SEQ ID NO:9), mouse N-RGMa (SEQ ID NO:10), or amino acids 1 to 417 of Accession No. AAI43272 (human Neogenin; SEQ ID NO:11).

Unlike these RGMa peptides, full-length RGMa was unable to bind the 4Ig domain of Neogenin as shown in FIG. 2A. Additionally, the data in FIG. 17C indicated that amino acids 40 to 73 of RGMa may also bind the 4Ig domain of Neogenin. Amino acids 40 to 73 of RGMa are set forth in SEQ ID NO:7. Together, these data suggested that a particular structure of RGMa contained within amino acids 40 to 73 of RGMa may be required to bind 4Ig and thus, mediate the cis interaction between RGMa and Neogenin and recruit Neogenin to the lipid rafts. This structure may be occluded in full-length RGMa, thus preventing full-length RGMa from binding the 4Ig-domain of Neogenin. This occlusion may be removed by another factor(s), for example, BMP, which as described above, was required for Neogenin recruitment to the lipid rafts. Removal of the occlusion may include a conformation change in RGMa.

Accordingly, an antibody that binds the 4Ig domain or this structure contained within amino acids 40 to 73 of RGMa may block the cis interaction between RGMa and Neogenin, and thus, block Neogenin recruitment to lipid rafts, promote neuronal cell survival and axon growth and/or regeneration.

These RGMa peptides and the 4Ig peptide will be used to generate and identify antibodies that block the cis interaction between RGMa and Neogenin, and thus, block Neogenin recruitment to lipid rafts. It is expected that these antibodies, by blocking Neogenin recruitment to lipid rafts, will promote neuronal cell survival and axon growth and/or regeneration.

Specifically, these antibodies will be generated by immunizing animals with one or more of the RGMa peptides or the 4Ig peptide. Sera will be collected from the animals and using the binding assay described in connection with FIG. 2A, FIG. 9, and FIG. 17, the sera will be screened for those sera that disrupt the interaction between N-Raft and 4Ig, i.e., binding between N-Raft and 4Ig is reduced or not measurable in the presence of the sera. Antibodies will then be purified from those sera that disrupt the interaction between N-Raft and 4Ig. It is expected that these purified antibodies will block Neogenin recruitment to the lipid rafts, and thus, promote neuronal cell survival and axon growth and/or regeneration.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method of treating retinitis pigmentosa, ischemia, multiple sclerosis, spinal cord injury, or optic nerve injury wherein the method comprises administering to the subject a composition comprising a pharmaceutically acceptable carrier and
   (i) a peptide consisting of amino acids 1 to 383 of SEQ ID NO: 1, or
   (ii) a peptide consisting of amino acids 1 to 417 of SEQ ID NO: 11.

2. The method of claim 1, wherein the ischemia is stroke.

3. The method of claim 2, wherein the method further comprises reducing at least one of infarct volume, brain edema, or a combination thereof in the subject.

4. The method of claim 1, wherein the disease is spinal cord injury and wherein the method further comprises restoring locomotor function in the subject.

5. The method of claim 1, wherein the disease is retinitis pigmentosa and wherein the method further comprises promoting survival of photoreceptor cells in the subject.

6. A method of treating retinitis pigmentosa, ischemia, multiple sclerosis, spinal cord injury, or optic nerve injury, wherein the wherein the method comprises administering to the subject a composition comprising a pharmaceutically acceptable carrier and a peptide consisting of an amino acid sequence having at least 95% identity to an amino acid sequence consisting of amino acids 1 to 383 of SEQ ID NO:1 or an amino acid sequence consisting of amino acids 1 to 417 of SEQ ID NO:11, which disrupts a cis interaction between Repulsive Guidance Molecule A (RGMa) and Neogenin.

* * * * *

SEQUENCE LISTING

<160> NUMBER OF SEQ ID NOS: 11

<210> SEQ ID NO 1
<211> LENGTH: 1443
<212> TYPE: PRT
<213> ORGANISM: Gallus gallus
<220> FEATURE:
<221> NAME/KEY: MISC_FEATURE
<223> OTHER INFORMATION: Neogenin - Accession No. AAC59662

<400> SEQUENCE: 1

```
Arg Ser Gly Pro Arg Ser Pro Leu Thr Gly Ser Val Val Arg Thr Phe
1               5                   10                  15

Thr Pro Phe Tyr Phe Leu Val Glu Pro Met Asp Ile Leu Ser Val Arg
            20                  25                  30

Gly Ala Ser Val Ile Met Asn Cys Ser Ser Tyr Cys Glu Thr Pro Pro
        35                  40                  45

Lys Ile Glu Trp Lys Lys Asp Gly Thr Leu Leu Asn Leu Val Ser Asp
    50                  55                  60

Asp Arg Arg Gln Leu Leu Pro Asp Gly Ser Leu Leu Ile Asn Ser Val
65                  70                  75                  80

Val His Ser Lys His Asn Lys Pro Asp Glu Gly Tyr Tyr Gln Cys Val
                85                  90                  95

Ala Thr Val Glu Ser Leu Gly Ser Ile Val Ser Arg Thr Ala Lys Leu
            100                 105                 110

Thr Val Ala Gly Leu Pro Arg Phe Thr Ser Gln Pro Glu Leu Ser Ser
        115                 120                 125

Val Tyr Lys Gly Asn Ser Ala Ile Leu Asn Cys Glu Val Asn Val Asp
    130                 135                 140

Leu Ala Pro Phe Val Arg Trp Glu Gln Asp Arg Gln Pro Leu Ser Leu
145                 150                 155                 160

Asp Asp Arg Val Phe Lys Leu Pro Ser Gly Ala Leu Leu Ile Gly Asn
                165                 170                 175

Ala Thr Asp Thr Asp Gly Gly Phe Tyr Arg Cys Val Ile Glu Ser Gly
            180                 185                 190

Gly Thr Pro Lys Tyr Ser Glu Glu Ala Glu Leu Lys Ile Leu Pro Asp
        195                 200                 205

Pro Glu Glu Pro Gln Ser Leu Val Phe Val Arg Gln Pro Ser Ser Leu
    210                 215                 220

Thr Lys Val Thr Gly Gln Asn Ala Val Phe Pro Cys Val Ala Gly Gly
225                 230                 235                 240

Phe Pro Thr Pro Tyr Val Arg Trp Thr Lys Asn Gly Glu Glu Leu Ile
                245                 250                 255

Thr Glu Asp Ser Glu Arg Phe Ala Leu Arg Ala Gly Gly Ser Leu Leu
            260                 265                 270

Ile Ser Asp Val Thr Glu Asp Val Gly Thr Tyr Thr Cys Ile Ala
        275                 280                 285

Asp Asn Glu Asn Glu Thr Ile Glu Ala Gln Ala Glu Leu Ala Val Gln
    290                 295                 300

Val Pro Pro Glu Phe Leu Lys Arg Pro Ala Asn Ile Tyr Ala His Glu
305                 310                 315                 320

Ser Met Asp Ile Val Phe Glu Cys Glu Val Thr Gly Lys Pro Thr Pro
                325                 330                 335

Thr Val Lys Trp Val Lys Asn Gly Asp Val Val Ile Pro Ser Asp Tyr
            340                 345                 350
```

```
Phe Lys Ile Val Lys Glu His Asn Leu Gln Val Leu Gly Leu Val Lys
        355                 360                 365

Ser Asp Glu Gly Phe Tyr Gln Cys Ile Ala Glu Asn Asp Val Gly Asn
    370                 375                 380

Ala Gln Ala Gly Ala Gln Leu Ile Ile Leu Asp Leu Asp Val Ala Ile
385                 390                 395                 400

Pro Thr Leu Pro Pro Thr Ser Leu Thr Ser Ala Thr Asn Asp His Leu
                405                 410                 415

Ala Pro Ala Thr Thr Gly Pro Leu Pro Thr Ala Pro Arg Asp Val Val
            420                 425                 430

Ala Thr Leu Val Ser Thr Arg Phe Ile Arg Leu Thr Trp Arg Thr Pro
        435                 440                 445

Val Ser Asp Pro Gln Gly Asp Asn Leu Thr Tyr Ser Ile Phe Tyr Thr
    450                 455                 460

Lys Glu Gly Ile Asn Arg Glu Arg Val Glu Asn Thr Ser Arg Pro Gly
465                 470                 475                 480

Glu Thr Gln Val Met Ile Gln Asn Leu Met Pro Glu Thr Val Tyr Val
                485                 490                 495

Phe Arg Val Val Ala Gln Asn Lys His Gly His Gly Glu Ser Ser Ala
            500                 505                 510

Pro Leu Lys Val Ala Thr Gln Pro Glu Val Gln Leu Pro Gly Pro Ala
        515                 520                 525

Pro Asn Ile Arg Ala Tyr Ala Gly Ser Pro Thr Ser Val Thr Val Thr
    530                 535                 540

Trp Glu Thr Pro Leu Ser Gly Asn Gly Glu Ile Gln Asn Tyr Lys Leu
545                 550                 555                 560

Tyr Tyr Met Glu Lys Gly Gln Asp Ser Glu Gln Asp Val Asp Val Ala
                565                 570                 575

Gly Leu Ser Tyr Thr Ile Thr Gly Leu Lys Lys Tyr Thr Glu Tyr Ser
            580                 585                 590

Phe Arg Val Val Ala Tyr Asn Lys His Gly Pro Gly Val Ser Thr Gln
        595                 600                 605

Asp Val Val Arg Thr Leu Ser Asp Val Pro Ser Ala Ala Pro Gln
    610                 615                 620

Asn Leu Thr Leu Glu Ala Arg Asn Ser Lys Ser Ile Met Leu His Trp
625                 630                 635                 640

Gln Pro Pro Pro Ala Gly Thr His Ser Gly Gln Ile Thr Gly Tyr Lys
                645                 650                 655

Ile Arg Tyr Arg Lys Val Ser Arg Lys Ser Asp Val Thr Glu Ser Val
            660                 665                 670

Gly Gly Thr Gln Leu Phe Gln Leu Ile Glu Gly Leu Glu Arg Gly Thr
        675                 680                 685

Glu Tyr Asn Phe Arg Ile Ala Ala Met Thr Val Asn Gly Thr Gly Pro
    690                 695                 700

Ala Thr Asp Trp Val Ser Ala Glu Thr Phe Glu Ser Asp Leu Asp Glu
705                 710                 715                 720

Ser Arg Val Pro Glu Val Pro Ser Ser Leu His Val Arg Pro Leu Val
                725                 730                 735

Thr Ser Ile Val Val Ser Trp Thr Pro Pro Glu Asn Gln Asn Ile Val
            740                 745                 750

Val Arg Gly Tyr Ala Ile Gly Tyr Gly Ile Gly Ser Pro His Ala Gln
        755                 760                 765

Thr Ile Lys Val Asp Tyr Lys Gln Arg Tyr Tyr Thr Ile Glu Asn Leu
```

```
                770                 775                 780
Asp Pro Ser Ser His Tyr Val Ile Thr Leu Lys Ala Phe Asn Asn Val
785                 790                 795                 800

Gly Glu Gly Ile Pro Leu Tyr Glu Ser Ala Val Thr Arg Pro His Ser
            805                 810                 815

Asp Thr Ser Glu Val Asp Leu Phe Val Ile Asn Ala Pro Tyr Thr Pro
            820                 825                 830

Val Pro Asp Pro Ser Pro Met Met Pro Pro Val Gly Val Gln Ala Ser
            835                 840                 845

Ile Leu Ser His Asp Thr Ile Arg Ile Thr Trp Ala Asp Asn Ser Leu
            850                 855                 860

Pro Lys Asn Gln Lys Ile Thr Asp Ala Arg Tyr Tyr Thr Val Arg Trp
865                 870                 875                 880

Lys Thr Asn Ile Pro Ala Asn Thr Lys Tyr Lys Thr Ala Asn Ala Thr
                885                 890                 895

Thr Leu Ser Tyr Leu Val Thr Gly Leu Lys Pro Asn Thr Leu Tyr Glu
                900                 905                 910

Phe Ser Val Met Val Thr Lys Gly Arg Arg Ser Ser Thr Trp Ser Met
            915                 920                 925

Thr Ala His Gly Thr Thr Phe Glu Leu Val Pro Thr Ser Pro Pro Lys
930                 935                 940

Asp Val Thr Val Val Ser Lys Glu Gly Lys Pro Arg Thr Ile Ile Val
945                 950                 955                 960

Asn Trp Gln Pro Pro Ser Glu Ala Asn Gly Lys Ile Thr Gly Tyr Ile
                965                 970                 975

Ile Tyr Tyr Ser Thr Asp Val Asn Ala Glu Ile His Asp Trp Val Ile
            980                 985                 990

Glu Pro Val Val Gly Asn Arg Leu Thr His Gln Ile Gln Glu Leu Thr
            995                 1000                1005

Leu Asp Thr Pro Tyr Tyr Phe Lys Ile Gln Ala Arg Asn Ser Lys
    1010                1015                1020

Gly Met Gly Pro Met Ser Glu Ala Val Gln Phe Arg Thr Pro Lys
    1025                1030                1035

Ala Glu Ser Ser Asp Lys Met Pro Asn Asp Gln Ala Ser Gly Ser
    1040                1045                1050

Ala Gly Lys Gly Ser Arg Pro Val Asp Val Gly Pro Asp Tyr Lys
    1055                1060                1065

Pro Pro Leu Ser Gly Ser Asn Ser Pro His Gly Ser Pro Thr Ser
    1070                1075                1080

Pro Leu Asp Ser Asn Met Leu Leu Val Ile Ile Val Ser Val Gly
    1085                1090                1095

Val Ile Thr Ile Val Ile Val Val Ile Val Ala Val Phe Cys Thr
    1100                1105                1110

Arg Arg Thr Thr Ser His Gln Lys Lys Lys Arg Ala Ala Cys Lys
    1115                1120                1125

Ser Val Asn Gly Ser His Lys Tyr Lys Gly Asn Ser Lys Asp Val
    1130                1135                1140

Lys Pro Pro Asp Leu Trp Ile His His Glu Arg Leu Glu Leu Lys
    1145                1150                1155

Pro Ile Asp Lys Ser Pro Asp Pro Asn Pro Ile Met Thr Asp Thr
    1160                1165                1170

Pro Ile Pro Arg Asn Ser Gln Asp Ile Thr Pro Val Asp Asn Ser
    1175                1180                1185
```

```
Met Asp Ser Asn Ile His Gln Arg Arg Asn Ser Tyr Arg Gly His
        1190                1195                1200

Glu Ser Glu Asp Ser Met Ser Thr Leu Ala Gly Arg Arg Gly Met
        1205                1210                1215

Arg Pro Lys Met Met Met Pro Phe Asp Ser Gln Pro Pro Gln Pro
        1220                1225                1230

Val Ile Ser Ala His Pro Ile His Ser Leu Asp Asn Pro His His
        1235                1240                1245

His Phe His Ser Gly Ser Leu Ala Ser Pro Thr Arg Ser Tyr Leu
        1250                1255                1260

His His Gln Val Ser Pro Trp Pro Val Gly Thr Ser Met Ser His
        1265                1270                1275

Ser Asp Arg Ala Asn Ser Thr Glu Ser Val Arg Asn Thr Pro Ser
        1280                1285                1290

Ser Asp Thr Met Pro Ala Ser Ser Ser Gln Pro Cys Ala Asp His
        1295                1300                1305

Gln Asp Pro Asp Ser Ser Ser Gly Ala Tyr Leu Gly Ser Ala Gln
        1310                1315                1320

Glu Glu Asp Ala Ala Gln Ser Leu Pro Thr Ala His Val Arg Pro
        1325                1330                1335

Ser His Pro Leu Lys Ser Phe Ala Val Pro Ala Val Pro Ala Ala
        1340                1345                1350

Gly Ser Ala Tyr Asp Pro Thr Leu Pro Ser Thr Pro Leu Leu Thr
        1355                1360                1365

Gln Gln Ala Pro Ser His Pro Val His Ser Val Lys Thr Ala Ser
        1370                1375                1380

Ile Gly Thr Leu Gly Arg Thr Arg Pro Pro Met Pro Val Val Val
        1385                1390                1395

Pro Ser Ala Pro Asp Val Gln Glu Thr Thr Arg Met Leu Glu Asp
        1400                1405                1410

Ser Glu Ser Ser Tyr Glu Pro Asp Gly Leu Thr Lys Glu Met Ala
        1415                1420                1425

His Leu Glu Gly Leu Met Lys Asp Leu Asn Ala Ile Thr Thr Ala
        1430                1435                1440

<210> SEQ ID NO 2
<211> LENGTH: 46
<212> TYPE: PRT
<213> ORGANISM: Artificial Sequence
<220> FEATURE:
<223> OTHER INFORMATION: N-Raft - amino acids 28-73 of RGMa

<400> SEQUENCE: 2

Ser Pro Cys Lys Ile Leu Lys Cys Asn Ser Glu Phe Trp Ala Ala Thr
1               5                   10                  15

Ser Gly Ser His His Leu Gly Ala Glu Glu Thr Pro Glu Phe Cys Thr
                20                  25                  30

Ala Leu Arg Ala Tyr Ala His Cys Thr Arg Arg Thr Ala Arg
        35                  40                  45

<210> SEQ ID NO 3
<211> LENGTH: 20
<212> TYPE: PRT
<213> ORGANISM: Artificial Sequence
<220> FEATURE:
<223> OTHER INFORMATION: Amino acids 54-73 of RGMa
```

```
<400> SEQUENCE: 3

Thr Pro Glu Phe Cys Thr Ala Leu Arg Ala Tyr Ala His Cys Thr Arg
1               5                   10                  15

Arg Thr Ala Arg
            20

<210> SEQ ID NO 4
<211> LENGTH: 23
<212> TYPE: PRT
<213> ORGANISM: Artificial Sequence
<220> FEATURE:
<223> OTHER INFORMATION: Amino acids 40-62 of RGMa

<400> SEQUENCE: 4

Trp Ala Ala Thr Ser Gly Ser His His Leu Gly Ala Glu Glu Thr Pro
1               5                   10                  15

Glu Phe Cys Thr Ala Leu Arg
            20

<210> SEQ ID NO 5
<211> LENGTH: 232
<212> TYPE: PRT
<213> ORGANISM: Homo sapiens
<220> FEATURE:
<221> NAME/KEY: MISC_FEATURE
<223> OTHER INFORMATION: Noggin - Accession No. AAA83259

<400> SEQUENCE: 5

Met Glu Arg Cys Pro Ser Leu Gly Val Thr Leu Tyr Ala Leu Val Val
1               5                   10                  15

Val Leu Gly Leu Arg Ala Thr Pro Ala Gly Gly Gln His Tyr Leu His
            20                  25                  30

Ile Arg Pro Ala Pro Ser Asp Asn Leu Pro Leu Val Asp Leu Ile Glu
        35                  40                  45

His Pro Asp Pro Ile Phe Asp Pro Lys Glu Lys Asp Leu Asn Glu Thr
    50                  55                  60

Leu Leu Arg Ser Leu Leu Gly Gly His Tyr Asp Pro Gly Phe Met Ala
65                  70                  75                  80

Thr Ser Pro Pro Glu Asp Arg Pro Gly Gly Gly Gly Ala Ala Gly Gly
                85                  90                  95

Gly Ala Glu Asp Leu Ala Glu Leu Asp Gln Leu Leu Arg Gln Arg Pro
            100                 105                 110

Ser Gly Ala Met Pro Ser Glu Ile Lys Gly Leu Glu Phe Ser Glu Gly
        115                 120                 125

Leu Ala Gln Gly Lys Lys Gln Arg Leu Ser Lys Lys Leu Arg Arg Lys
    130                 135                 140

Leu Gln Met Trp Leu Trp Ser Gln Thr Phe Cys Pro Val Leu Tyr Ala
145                 150                 155                 160

Trp Asn Asp Leu Gly Ser Arg Phe Trp Pro Arg Tyr Val Lys Val Gly
                165                 170                 175

Ser Cys Phe Ser Lys Arg Ser Cys Ser Val Pro Glu Gly Met Val Cys
            180                 185                 190

Lys Pro Ser Lys Ser Val His Leu Thr Val Leu Arg Trp Arg Cys Gln
        195                 200                 205

Arg Arg Gly Gly Gln Arg Cys Gly Trp Ile Pro Ile Gln Tyr Pro Ile
    210                 215                 220

Ile Ser Glu Cys Lys Cys Ser Cys
225                 230
```

<210> SEQ ID NO 6
<211> LENGTH: 432
<212> TYPE: PRT
<213> ORGANISM: Gallus gallus
<220> FEATURE:
<221> NAME/KEY: MISC_FEATURE
<223> OTHER INFORMATION: RGMa - Accession No. NP_989868.1

<400> SEQUENCE: 6

```
Met Gly Arg Gly Ala Gly Ser Thr Ala Leu Gly Leu Phe Gln Ile Leu
1               5                   10                  15

Pro Val Phe Leu Cys Ile Phe Pro Pro Val Thr Ser Pro Cys Lys Ile
            20                  25                  30

Leu Lys Cys Asn Ser Glu Phe Trp Ala Ala Thr Ser Gly Ser His His
        35                  40                  45

Leu Gly Ala Glu Glu Thr Pro Glu Phe Cys Thr Ala Leu Arg Ala Tyr
    50                  55                  60

Ala His Cys Thr Arg Arg Thr Ala Arg Thr Cys Arg Gly Asp Leu Ala
65                  70                  75                  80

Tyr His Ser Ala Val His Gly Ile Asp Asp Leu Met Val Gln His Asn
                85                  90                  95

Cys Ser Lys Asp Gly Pro Thr Ser Gln Pro Arg Leu Arg Thr Leu Pro
            100                 105                 110

Pro Gly Asp Ser Gln Glu Arg Ser Asp Ser Pro Glu Ile Cys His Tyr
        115                 120                 125

Glu Lys Ser Phe His Lys His Ser Ala Ala Pro Asn Tyr Thr His Cys
    130                 135                 140

Gly Leu Phe Gly Asp Pro His Leu Arg Thr Phe Thr Asp Thr Phe Gln
145                 150                 155                 160

Thr Cys Lys Val Gln Gly Ala Trp Pro Leu Ile Asp Asn Asn Tyr Leu
                165                 170                 175

Asn Val Gln Val Thr Asn Thr Pro Val Leu Pro Gly Ser Ser Ala Thr
            180                 185                 190

Ala Thr Ser Lys Leu Thr Ile Ile Phe Lys Ser Phe Gln Glu Cys Val
        195                 200                 205

Glu Gln Lys Val Tyr Gln Ala Glu Met Asp Glu Leu Pro Ala Ala Phe
    210                 215                 220

Ala Asp Gly Ser Lys Asn Gly Gly Asp Lys His Gly Ala Asn Ser Leu
225                 230                 235                 240

Lys Ile Thr Glu Lys Val Ser Gly Gln His Ile Glu Ile Gln Ala Lys
                245                 250                 255

Tyr Ile Gly Thr Thr Ile Val Val Arg Gln Val Gly Arg Tyr Leu Thr
            260                 265                 270

Phe Ala Val Arg Met Pro Glu Glu Val Val Asn Ala Val Glu Asp Arg
        275                 280                 285

Asp Ser Gln Gly Leu Tyr Leu Cys Leu Arg Gly Cys Pro Leu Asn Gln
    290                 295                 300

Gln Ile Asp Phe Gln Thr Phe Arg Leu Ala Gln Ala Ala Glu Gly Arg
305                 310                 315                 320

Ala Arg Arg Lys Gly Pro Ser Leu Pro Ala Pro Pro Glu Ala Phe Thr
                325                 330                 335

Tyr Glu Ser Ala Thr Ala Lys Cys Arg Glu Lys Leu Pro Val Glu Asp
            340                 345                 350

Leu Tyr Phe Gln Ser Cys Val Phe Asp Leu Leu Thr Thr Gly Asp Val
```

```
                355                 360                 365
Asn Phe Met Leu Ala Ala Tyr Tyr Ala Phe Glu Asp Val Lys Met Leu
        370                 375                 380

His Ser Asn Lys Asp Lys Leu His Leu Tyr Glu Arg Thr Arg Ala Leu
385                 390                 395                 400

Ala Pro Gly Asn Ala Ala Pro Ser Glu His Pro Trp Ala Leu Pro Ala
                405                 410                 415

Leu Trp Val Ala Leu Leu Ser Leu Ser Gln Cys Trp Leu Gly Leu Leu
        420                 425                 430

<210> SEQ ID NO 7
<211> LENGTH: 34
<212> TYPE: PRT
<213> ORGANISM: Artificial Sequence
<220> FEATURE:
<223> OTHER INFORMATION: Amino acids 40-73 of RGMa

<400> SEQUENCE: 7

Trp Ala Ala Thr Ser Gly Ser His His Leu Gly Ala Glu Glu Thr Pro
1               5                   10                  15

Glu Phe Cys Thr Ala Leu Arg Ala Tyr Ala His Cys Thr Arg Arg Thr
                20                  25                  30

Ala Arg

<210> SEQ ID NO 8
<211> LENGTH: 417
<212> TYPE: PRT
<213> ORGANISM: Artificial Sequence
<220> FEATURE:
<223> OTHER INFORMATION: 4Ig domain of Human Neogenin

<400> SEQUENCE: 8

Met Ala Ala Glu Arg Gly Ala Arg Arg Leu Leu Ser Thr Pro Ser Phe
1               5                   10                  15

Trp Leu Tyr Cys Leu Leu Leu Gly Arg Arg Ala Pro Gly Ala Ala
                20                  25                  30

Ala Ala Arg Ser Gly Ser Ala Pro Gln Ser Pro Gly Ala Ser Ile Arg
            35                  40                  45

Thr Phe Thr Pro Phe Tyr Phe Leu Val Glu Pro Val Asp Thr Leu Ser
        50                  55                  60

Val Arg Gly Ser Ser Val Ile Leu Asn Cys Ser Ala Tyr Ser Glu Pro
65                  70                  75                  80

Ser Pro Lys Ile Glu Trp Lys Lys Asp Gly Thr Phe Leu Asn Leu Val
                85                  90                  95

Ser Asp Asp Arg Arg Gln Leu Leu Pro Asp Gly Ser Leu Phe Ile Ser
            100                 105                 110

Asn Val Val His Ser Lys His Asn Lys Pro Asp Glu Gly Tyr Tyr Gln
        115                 120                 125

Cys Val Ala Thr Val Glu Ser Leu Gly Thr Ile Ile Ser Arg Thr Ala
    130                 135                 140

Lys Leu Ile Val Ala Gly Leu Pro Arg Phe Thr Ser Gln Pro Glu Pro
145                 150                 155                 160

Ser Ser Val Tyr Ala Gly Asn Asn Ala Ile Leu Asn Cys Glu Val Asn
                165                 170                 175

Ala Asp Leu Val Pro Phe Val Arg Trp Glu Gln Asn Arg Gln Pro Leu
            180                 185                 190

Leu Leu Asp Asp Arg Val Ile Lys Leu Pro Ser Gly Met Leu Val Ile
```

```
            195                 200                 205
Ser Asn Ala Thr Glu Gly Asp Gly Leu Tyr Arg Cys Val Val Glu
210                 215                 220

Ser Gly Gly Pro Pro Lys Tyr Ser Asp Glu Val Glu Leu Lys Val Leu
225                 230                 235                 240

Pro Asp Pro Glu Val Ile Ser Asp Leu Val Phe Leu Lys Gln Pro Ser
                245                 250                 255

Pro Leu Val Arg Val Ile Gly Gln Asp Val Val Leu Pro Cys Val Ala
                260                 265                 270

Ser Gly Leu Pro Thr Pro Thr Ile Lys Trp Met Lys Asn Glu Glu Ala
                275                 280                 285

Leu Asp Thr Glu Ser Ser Glu Arg Leu Val Leu Leu Ala Gly Gly Ser
290                 295                 300

Leu Glu Ile Ser Asp Val Thr Glu Asp Ala Gly Thr Tyr Phe Cys
305                 310                 315                 320

Ile Ala Asp Asn Gly Asn Glu Thr Ile Glu Ala Gln Ala Glu Leu Thr
                325                 330                 335

Val Gln Ala Gln Pro Glu Phe Leu Lys Gln Pro Thr Asn Ile Tyr Ala
                340                 345                 350

His Glu Ser Met Asp Ile Val Phe Glu Cys Glu Val Thr Gly Lys Pro
                355                 360                 365

Thr Pro Thr Val Lys Trp Val Lys Asn Gly Asp Met Val Ile Pro Ser
                370                 375                 380

Asp Tyr Phe Lys Ile Val Lys Glu His Asn Leu Gln Val Leu Gly Leu
385                 390                 395                 400

Val Lys Ser Asp Glu Gly Phe Tyr Gln Cys Ile Ala Glu Asn Asp Val
                405                 410                 415

Gly

<210> SEQ ID NO 9
<211> LENGTH: 165
<212> TYPE: PRT
<213> ORGANISM: Artificial Sequence
<220> FEATURE:
<223> OTHER INFORMATION: Mouse N-RGMc

<400> SEQUENCE: 9

Met Gly Gln Ser Pro Ser Pro Arg Ser Pro His Gly Ser Pro Pro Thr
1               5                   10                  15

Leu Ser Thr Leu Thr Leu Leu Leu Leu Cys Gly Gln Ala His Ser
                20                  25                  30

Gln Cys Lys Ile Leu Arg Cys Asn Ala Glu Tyr Val Ser Ser Thr Leu
            35                  40                  45

Ser Leu Arg Gly Gly Gly Ser Pro Asp Thr Pro Arg Gly Gly Arg
50                  55                  60

Gly Gly Leu Ala Ser Gly Gly Leu Cys Arg Ala Leu Arg Ser Tyr Ala
65                  70                  75                  80

Leu Cys Thr Arg Arg Thr Ala Arg Thr Cys Arg Gly Asp Leu Ala Phe
                85                  90                  95

His Ser Ala Val His Gly Ile Glu Asp Leu Met Ile Gln His Asn Cys
                100                 105                 110

Ser Arg Gln Gly Pro Thr Ala Pro Pro Ala Arg Gly Pro Ala Leu
            115                 120                 125

Pro Gly Ala Gly Pro Ala Pro Leu Thr Pro Asp Pro Cys Asp Tyr Glu
            130                 135                 140
```

-continued

Ala Arg Phe Ser Arg Leu His Gly Arg Ala Pro Gly Phe Leu His Cys
145                 150                 155                 160

Ala Ser Phe Gly Asp
                165

<210> SEQ ID NO 10
<211> LENGTH: 162
<212> TYPE: PRT
<213> ORGANISM: Artificial Sequence
<220> FEATURE:
<223> OTHER INFORMATION: Mouse N-RGMa

<400> SEQUENCE: 10

Met Gln Pro Pro Arg Glu Arg Leu Val Val Thr Gly Arg Ala Gly Trp
1               5                   10                  15

Met Gly Met Gly Arg Gly Ala Gly Arg Ser Ala Leu Gly Leu Trp Pro
            20                  25                  30

Thr Leu Ala Phe Leu Leu Cys Ser Phe Pro Ala Ala Ile Ser Pro Cys
        35                  40                  45

Lys Ile Leu Lys Cys Asn Ser Glu Phe Trp Ser Ala Thr Ser Ser Gly
    50                  55                  60

Ser His Ala Pro Ala Ser Asp Asp Val Pro Glu Phe Cys Ala Ala Leu
65                  70                  75                  80

Arg Thr Tyr Ala Leu Cys Thr Arg Arg Thr Ala Arg Thr Cys Arg Gly
                85                  90                  95

Asp Leu Ala Tyr His Ser Ala Val His Gly Ile Glu Asp Leu Met Ser
            100                 105                 110

Gln His Asn Cys Ser Lys Asp Gly Pro Thr Ser Gln Pro Arg Val Arg
        115                 120                 125

Thr Leu Pro Pro Ala Gly Asp Ser Gln Glu Arg Ser Asp Ser Pro Glu
    130                 135                 140

Ile Cys His Tyr Glu Lys Ser Phe His Lys His Ser Ala Ala Pro Asn
145                 150                 155                 160

Tyr Thr

<210> SEQ ID NO 11
<211> LENGTH: 1450
<212> TYPE: PRT
<213> ORGANISM: Homo sapiens
<220> FEATURE:
<221> NAME/KEY: MISC_FEATURE
<223> OTHER INFORMATION: Neogenin - Accession No. AAI43272

<400> SEQUENCE: 11

Met Ala Ala Glu Arg Gly Ala Arg Arg Leu Leu Ser Thr Pro Ser Phe
1               5                   10                  15

Trp Leu Tyr Cys Leu Leu Leu Gly Arg Arg Ala Pro Gly Ala Ala
            20                  25                  30

Ala Ala Arg Ser Gly Ser Ala Pro Gln Ser Pro Gly Ala Ser Ile Arg
        35                  40                  45

Thr Phe Thr Pro Phe Tyr Phe Leu Val Glu Pro Val Asp Thr Leu Ser
    50                  55                  60

Val Arg Gly Ser Ser Val Ile Leu Asn Cys Ser Ala Tyr Ser Glu Pro
65                  70                  75                  80

Ser Pro Lys Ile Glu Trp Lys Lys Asp Gly Thr Phe Leu Asn Leu Val
                85                  90                  95

Ser Asp Asp Arg Arg Gln Leu Leu Pro Asp Gly Ser Leu Phe Ile Ser

```
                100                 105                 110
Asn Val Val His Ser Lys His Asn Lys Pro Asp Glu Gly Tyr Tyr Gln
            115                 120                 125

Cys Val Ala Thr Val Glu Ser Leu Gly Thr Ile Ile Ser Arg Thr Ala
            130                 135             140

Lys Leu Ile Val Ala Gly Leu Pro Arg Phe Thr Ser Gln Pro Glu Pro
145                 150                 155                 160

Ser Ser Val Tyr Ala Gly Asn Asn Ala Ile Leu Asn Cys Glu Val Asn
                165                 170                 175

Ala Asp Leu Val Pro Phe Val Arg Trp Glu Gln Asn Arg Gln Pro Leu
            180                 185                 190

Leu Leu Asp Asp Arg Val Ile Lys Leu Pro Ser Gly Met Leu Val Ile
        195                 200                 205

Ser Asn Ala Thr Glu Gly Asp Gly Gly Leu Tyr Arg Cys Val Val Glu
        210                 215                 220

Ser Gly Gly Pro Pro Lys Tyr Ser Asp Glu Val Glu Leu Lys Val Leu
225                 230                 235                 240

Pro Asp Pro Glu Val Ile Ser Asp Leu Val Phe Leu Lys Gln Pro Ser
                245                 250                 255

Pro Leu Val Arg Val Ile Gly Gln Asp Val Val Leu Pro Cys Val Ala
                260                 265                 270

Ser Gly Leu Pro Thr Pro Thr Ile Lys Trp Met Lys Asn Glu Glu Ala
            275                 280                 285

Leu Asp Thr Glu Ser Ser Glu Arg Leu Val Leu Leu Ala Gly Gly Ser
        290                 295                 300

Leu Glu Ile Ser Asp Val Thr Glu Asp Asp Ala Gly Thr Tyr Phe Cys
305                 310                 315                 320

Ile Ala Asp Asn Gly Asn Glu Thr Ile Glu Ala Gln Ala Glu Leu Thr
                325                 330                 335

Val Gln Ala Gln Pro Glu Phe Leu Lys Gln Pro Thr Asn Ile Tyr Ala
            340                 345                 350

His Glu Ser Met Asp Ile Val Phe Glu Cys Glu Val Thr Gly Lys Pro
        355                 360                 365

Thr Pro Thr Val Lys Trp Val Lys Asn Gly Asp Met Val Ile Pro Ser
370                 375                 380

Asp Tyr Phe Lys Ile Val Lys Glu His Asn Leu Gln Val Leu Gly Leu
385                 390                 395                 400

Val Lys Ser Asp Glu Gly Phe Tyr Gln Cys Ile Ala Glu Asn Asp Val
                405                 410                 415

Gly Asn Ala Gln Ala Gly Ala Gln Leu Ile Ile Leu Glu His Ala Pro
            420                 425                 430

Ala Thr Thr Gly Pro Leu Pro Ser Ala Pro Arg Asp Val Val Ala Ser
        435                 440                 445

Leu Val Ser Thr Arg Phe Ile Lys Leu Thr Trp Arg Thr Pro Ala Ser
450                 455                 460

Asp Pro His Gly Asp Asn Leu Thr Tyr Ser Val Phe Tyr Thr Lys Glu
465                 470                 475                 480

Gly Ile Ala Arg Glu Arg Val Glu Asn Thr Ser His Pro Gly Glu Met
                485                 490                 495

Gln Val Thr Ile Gln Asn Leu Met Pro Ala Thr Val Tyr Ile Phe Arg
            500                 505                 510

Val Met Ala Gln Asn Lys His Gly Ser Gly Glu Ser Ser Ala Pro Leu
        515                 520                 525
```

-continued

```
Arg Val Glu Thr Gln Pro Glu Val Gln Leu Pro Gly Pro Ala Pro Asn
    530                 535                 540

Leu Arg Ala Tyr Ala Ala Ser Pro Thr Ser Ile Thr Val Thr Trp Glu
545                 550                 555                 560

Thr Pro Val Ser Gly Asn Gly Glu Ile Gln Asn Tyr Lys Leu Tyr Tyr
                565                 570                 575

Met Glu Lys Gly Thr Asp Lys Glu Gln Asp Val Asp Val Ser Ser His
            580                 585                 590

Ser Tyr Thr Ile Asn Gly Leu Lys Lys Tyr Thr Glu Tyr Ser Phe Arg
        595                 600                 605

Val Val Ala Tyr Asn Lys His Gly Pro Gly Val Ser Thr Pro Asp Val
    610                 615                 620

Ala Val Arg Thr Leu Ser Asp Val Pro Ser Ala Ala Pro Gln Asn Leu
625                 630                 635                 640

Ser Leu Glu Val Arg Asn Ser Lys Ser Ile Met Ile His Trp Gln Pro
                645                 650                 655

Pro Ala Pro Ala Thr Gln Asn Gly Gln Ile Thr Gly Tyr Lys Ile Arg
            660                 665                 670

Tyr Arg Lys Ala Ser Arg Lys Ser Asp Val Thr Glu Thr Leu Val Ser
        675                 680                 685

Gly Thr Gln Leu Ser Gln Leu Ile Glu Gly Leu Asp Arg Gly Thr Glu
    690                 695                 700

Tyr Asn Phe Arg Val Ala Ala Leu Thr Ile Asn Gly Thr Gly Pro Ala
705                 710                 715                 720

Thr Asp Trp Leu Ser Ala Glu Thr Phe Glu Ser Asp Leu Asp Glu Thr
                725                 730                 735

Arg Val Pro Glu Val Pro Ser Ser Leu His Val Arg Pro Leu Val Thr
            740                 745                 750

Ser Ile Val Val Ser Trp Thr Pro Pro Glu Asn Gln Asn Ile Val Val
        755                 760                 765

Arg Gly Tyr Ala Ile Gly Tyr Gly Ile Gly Ser Pro His Ala Gln Thr
    770                 775                 780

Ile Lys Val Asp Tyr Lys Gln Arg Tyr Tyr Thr Ile Glu Asn Leu Asp
785                 790                 795                 800

Pro Ser Ser His Tyr Val Ile Thr Leu Lys Ala Phe Asn Asn Val Gly
                805                 810                 815

Glu Gly Ile Pro Leu Tyr Glu Ser Ala Val Thr Arg Pro His Thr Asp
            820                 825                 830

Thr Ser Glu Val Asp Leu Phe Val Ile Asn Ala Pro Tyr Thr Pro Val
        835                 840                 845

Pro Asp Pro Thr Pro Met Met Pro Pro Val Gly Val Gln Ala Ser Ile
    850                 855                 860

Leu Ser His Asp Thr Ile Arg Ile Thr Trp Ala Asp Asn Ser Leu Pro
865                 870                 875                 880

Lys His Gln Lys Ile Thr Asp Ser Arg Tyr Tyr Thr Val Arg Trp Lys
                885                 890                 895

Thr Asn Ile Pro Ala Asn Thr Lys Tyr Lys Asn Ala Asn Ala Thr Thr
            900                 905                 910

Leu Ser Tyr Leu Val Thr Gly Leu Lys Pro Asn Thr Leu Tyr Glu Phe
        915                 920                 925

Ser Val Met Val Thr Lys Gly Arg Arg Ser Ser Thr Trp Ser Met Thr
    930                 935                 940
```

```
Ala His Gly Thr Thr Phe Glu Leu Val Pro Thr Ser Pro Pro Lys Asp
945                 950                 955                 960

Val Thr Val Val Ser Lys Glu Gly Lys Pro Lys Thr Ile Ile Val Asn
                965                 970                 975

Trp Gln Pro Pro Ser Glu Ala Asn Gly Lys Ile Thr Gly Tyr Ile Ile
            980                 985                 990

Tyr Tyr Ser Thr Asp Val Asn Ala Glu Ile His Asp Trp Val Ile Glu
        995                 1000                1005

Pro Val Val Gly Asn Arg Leu Thr His Gln Ile Gln Glu Leu Thr
    1010                1015                1020

Leu Asp Thr Pro Tyr Tyr Phe Lys Ile Gln Ala Arg Asn Ser Lys
    1025                1030                1035

Gly Met Gly Pro Met Ser Glu Ala Val Gln Phe Arg Thr Pro Lys
    1040                1045                1050

Ala Ser Gly Ser Gly Gly Lys Gly Ser Arg Leu Pro Asp Leu Gly
    1055                1060                1065

Ser Asp Tyr Lys Pro Pro Met Ser Gly Ser Asn Ser Pro His Gly
    1070                1075                1080

Ser Pro Thr Ser Pro Leu Asp Ser Asn Met Leu Leu Val Ile Ile
    1085                1090                1095

Val Ser Val Gly Val Ile Thr Ile Val Val Val Ile Ile Ala
    1100                1105                1110

Val Phe Cys Thr Arg Arg Thr Thr Ser His Gln Lys Lys Lys Arg
    1115                1120                1125

Ala Ala Cys Lys Ser Val Asn Gly Ser His Lys Tyr Lys Gly Asn
    1130                1135                1140

Ser Lys Asp Val Lys Pro Pro Asp Leu Trp Ile His His Glu Arg
    1145                1150                1155

Leu Glu Leu Lys Pro Ile Asp Lys Ser Pro Asp Pro Asn Pro Ile
    1160                1165                1170

Met Thr Asp Thr Pro Ile Pro Arg Asn Ser Gln Asp Ile Thr Pro
    1175                1180                1185

Val Asp Asn Ser Met Asp Ser Asn Ile His Gln Arg Arg Asn Ser
    1190                1195                1200

Tyr Arg Gly His Glu Ser Glu Asp Ser Met Ser Thr Leu Ala Gly
    1205                1210                1215

Arg Arg Gly Met Arg Pro Lys Met Met Met Pro Phe Asp Ser Gln
    1220                1225                1230

Pro Pro Gln Pro Val Ile Ser Ala His Pro Ile His Ser Leu Asp
    1235                1240                1245

Asn Pro His His His Phe His Ser Ser Ser Leu Ala Ser Pro Ala
    1250                1255                1260

Arg Ser His Leu Tyr His Pro Gly Ser Pro Trp Pro Ile Gly Thr
    1265                1270                1275

Ser Met Ser Leu Ser Asp Arg Ala Asn Ser Thr Glu Ser Val Arg
    1280                1285                1290

Asn Thr Pro Ser Thr Asp Thr Met Pro Ala Ser Ser Ser Gln Thr
    1295                1300                1305

Cys Cys Thr Asp His Gln Asp Pro Glu Gly Ala Thr Ser Ser Ser
    1310                1315                1320

Tyr Leu Ala Ser Ser Gln Glu Glu Asp Ser Gly Gln Ser Leu Pro
    1325                1330                1335

Thr Ala His Val Arg Pro Ser His Pro Leu Lys Ser Phe Ala Val
```

-continued

```
                   1340                    1345                    1350
Pro Ala Ile Pro Pro Gly Pro Pro Thr Tyr Asp Pro Ala Leu
    1355                    1360                    1365

Pro Ser Thr Pro Leu Leu Ser Gln Gln Ala Leu Asn His His Ile
    1370                    1375                    1380

His Ser Val Lys Thr Ala Ser Ile Gly Thr Leu Gly Arg Ser Arg
    1385                    1390                    1395

Pro Pro Met Pro Val Val Val Pro Ser Ala Pro Glu Val Gln Glu
    1400                    1405                    1410

Thr Thr Arg Met Leu Glu Asp Ser Glu Ser Ser Tyr Glu Pro Asp
    1415                    1420                    1425

Glu Leu Thr Lys Glu Met Ala His Leu Glu Gly Leu Met Lys Asp
    1430                    1435                    1440

Leu Asn Ala Ile Thr Thr Ala
    1445                    1450
```